United States Patent [19]
Saito

[11] Patent Number: 5,968,020
[45] Date of Patent: *Oct. 19, 1999

[54] SYRINGE ASSEMBLY

[76] Inventor: Yoshikuni Saito, Ooaza Kitanogami 1930, Kurobanemachi, Nasu-gun,Tochigi-Ken, Japan

[*] Notice: This patent is subject to a terminal disclaimer.

[21] Appl. No.: 08/616,830

[22] Filed: Mar. 15, 1996

Related U.S. Application Data

[63] Continuation-in-part of application No. 08/531,670, Sep. 21, 1995, Pat. No. 5,772,687, which is a continuation of application No. 08/213,434, Mar. 14, 1994, abandoned.

[30] Foreign Application Priority Data

Mar. 12, 1993 [JP] Japan ...................................... 5-79184
Apr. 6, 1993 [JP] Japan .................................... 5-103527
Dec. 6, 1995 [JP] Japan .................................... 7-344861

[51] Int. Cl.$^6$ .............................. A61M 5/00; A61M 5/31
[52] U.S. Cl. ...................... 604/243; 604/110; 604/195; 604/228; 604/240
[58] Field of Search ..................... 604/110, 195, 604/240–243, 197, 228, 227, 229, 181, 187, 196, 218

[56] References Cited

U.S. PATENT DOCUMENTS 5,047,016  9/1991  Dolgin et al. ............................ 604/240
5,205,824  4/1993  Mazur ..................................... 604/195
5,205,827  4/1993  Novacek et al. ........................ 604/195
5,256,151  10/1993  Chul ........................................ 604/195
5,489,272  2/1996  Wirtz ...................................... 604/195
5,531,705  7/1996  Alter et al. .............................. 604/240
5,634,903  6/1997  Kurose et al. .......................... 604/195
5,658,257  8/1997  Ryles ...................................... 604/195

FOREIGN PATENT DOCUMENTS

S56149633  4/1983  Japan .
S57-24143  8/1983  Japan .
S5932266  9/1986  Japan .

Primary Examiner—Ronald Stright
Attorney, Agent, or Firm—Eckert Seamans Cherin & Mellott, LLC

[57] ABSTRACT

A syringe assembly has a cylindrical hole extending between the inside and outside of the syringe body for attachably and detachably carrying a holding member that in turn carries a liquid flow tube (e.g., a needle or similar tube). The holding member seals with the syringe body and permits the flow tube to communicate between the inside and outside of the syringe body. The holding member has a main body that is axially insertable into the installing hole and can be axially pulled from the installing hole into the syringe body after the plunger is advanced to engage the holding member. An annular groove or a projection on the outside of the holding member fits with a corresponding projection or groove on the inner wall of the installing hole to seal the holding member to the syringe body along a plane perpendicular to the axis. The groove is narrower in the axial direction than the projection, producing an effective seal with a predetermined contact pressure which can be overcome when the holding member is drawn into the syringe body.

19 Claims, 24 Drawing Sheets

FIG. 1

SYRINGE ASSEMBLY

CROSS REFERENCE TO RELATED APPLICATIONS

This is a continuation-in-part of application Ser. No. 08/531,670, filed Sep. 21, 1995, now U.S. Pat. No. 5,772, 687, which is a continuation of application Ser. No. 08/213, 434, filed Mar. 14, 1994, now abandoned.

CLAIM OF PRIORITY

Certified copies of Japanese applications H05-103527 and H05-79184 were filed in parent application Ser. No. 08/531, 670. A claim of foreign priority under 35 U.S.C. § 119 appears in the original Declaration for Patent Application and is hereby reiterated. The filing of priority documents in the parent application is sufficient to perfect the claim of priority made in this application. MPEP 201.14(b).

BACKGROUND OF THE INVENTION

This invention relates to a syringe assembly, suitable for applying to a throwaway syringe assembly.

Since a patient's blood included pathogenic bacteria may adhere to a needle of a syringe assembly used, many throwaway syringe assemblies which are not reused, have been used for preventing secondary infection. As one of these throwaway syringe assemblies, various kinds of the syringe assembly of the needle pulling type, capable of dispose of in such a state that it is impossible to contact a needle from the outside by inserting the needle to which bloods or the like adhere after use into a syringe of the syringe assembly, have been proposed and used.

In this syringe assembly of the needle pulling type, generally, a predetermined needle holding member is attachably and detachably provided at the top end of a syringe body, and the needle can be connected with the needle holding member. That is, when the needle is pulled out into the syringe body, the needle holding member connected the needle therewith can be pulled out into the syringe body together with the needle. Therefore, the desire to this syringe assembly of this needle pulling type is that the installment and the releasement of the needle holding member to the syringe body is easily executed with small force, then the pulling operation of the needle is easily executed. On the other hand, as is basic functions that needle assemblies should fulfill, the needle holding member should be certainly fixed with the syringe body, and the portion between the syringe body and the needle holding member should be sealed when the needle holding member is installed in the syringe body.

As mentioned before, the desire to the syringe assembly of the needle pulling type is that the installment between the syringe body and the needle holding member is realized in such a manner that the needle holding member is certainly fixed with the syringe body, the sealing efficiency between the syringe body and the needle holding member is extremely improved, and the installment and the releasement of the needle holding member to the syringe body is extremely easily executed with small force.

In addition, the need to the syringe assembly of the needle pulling type is that the structure is extremely easy, then its assembly and operation is extremely easy.

An object of the present invention is to provide a syringe assembly to be applied to the syringe assembly of the needle pulling type, in which the installment between the syringe body and the needle holing member can be realized in such a state that the needle holding member is certainly fixed with the syringe body, the sealing efficiency between the syringe body and the needle holding member can be extremely improved, and the installment and the releasement of the needle holding member to the syringe body can be extremely easily executed with small force, and the whole structure of the syringe assembly is extremely easy, then its assembly and operation is extremely easy, taking the above-mentioned circumstances into consideration.

SUMMARY OF THE INVENTION

Of the present invention, the 1st invention is a syringe assembly, comprising:

a syringe body;

a piston installed in said syringe body, slidably in an axis center direction of said syringe body;

a holding member installing hole in the shape of a cylinder formed on a top end of said syringe body;

a penetrating hole provided with a top end of said holding member installing hole, communicating said holding member installing hole and an outside of said syringe body with each other; and a liquid flow tube holding member capable of connecting a liquid flow tube member therewith, attachably and detachably connected with said holding member installing hole through a predetermined sealing structure, said syringe assembly further comprising:

said liquid flow tube holding member having a member main body, capable of being linearly inserted into said holding member installing hole in said axis center direction of said syringe body and capable of being linearly pulled out of said holding member installing hole into said syringe body in said axis center direction of said syringe body;

a groove or a projection comprising said sealing structure between an outer peripheral portion of said member main body and an inner peripheral portion of said holding member installing hole, annularly formed along a plane perpendicular to said axis center direction of said member main body at an outer peripheral portion of said member main body, said groove having a first width in said axis center direction of said syringe body and said projection having a second width broader than said first width in said axis center direction of said syringe body;

a holding member side engagement means capable of engaging with said piston, provided with said member main body;

said projection or said groove comprising said sealing structure annularly formed along a plane perpendicular to said axis center direction of said syringe body at an inner peripheral portion of said holding member installing hole; and said member main body located such that when it is installed in said holding member installing hole, said groove is contacted and engaged with said projection with a predetermined contact pressure.

That is, the member main body and the holding member installing hole are contacted and engaged with each other through the sealing structure, thereby the liquid flow tube holding member is certainly fixed with the syringe body, and the portion between the liquid flow tube holding member and the syringe body is certainly sealed. In particular, the second width of the projection comprising the sealing structure is broader than the first width of the groove comprising the sealing structure. Therefore, when the groove and the projection are engaged with each other, its contact portion is in the point contact state in the section in the axis direction of the liquid flow tube holding member, then high sealing efficiency can be exercised in comparison with face contact. Besides, the engagement and installment of the liquid flow tube holding member to the syringe body is realized by the contact and engagement by the point contact state in the sealing structure. Therefore, when the liquid flow tube holding member is pulled out of the holding member installing hole, the frictional force acting between the liquid flow tube holding member and the syringe body, in the point-contact-state case said above, could be smaller than one in the case where the engagement and installment of the liquid flow tube holding member to the syringe body would be realized by the face contact. That is, the installment and the releasement of the liquid flow tube holding member to the syringe body can be extremely easily executed with small force. Furthermore, in the syringe assembly according to the present invention, the sealing structure for realizing the installation of the liquid flow tube holding member to the holding member installing hole is comprised of a groove and a projection, and the whole structure of the syringe assembly is extremely easy in comparison with a conventional syringe assembly, such as the screwing type of syringe assembly. Then, when the liquid flow tube holding member is installed in the holding member installing hole of the top end of the syringe body, the liquid flow tube holding member needs just to be linearly inserted into the holding member installing hole in the axis center direction of the syringe body so as to contact and engage the portion between the liquid flow tube holding member and the holding member installing hole with the sealing structure. When the liquid flow tube holding member is detached from the holding member installing hole, the piston needs to be linearly operated in the axis center direction of the syringe body so as to engage the liquid flow tube holding member with the piston itself each other through the holding member side engagement means, furthermore, the piston needs to be linearly operated in the axis center direction of the syringe body so as to pull the liquid flow tube holding member into the syringe body together with the piston itself, therefore it is easy.

In the syringe assembly according to the 1st invention, as explained heretofore, the installation between the syringe body and the liquid flow tube holding member can be realized in such a manner that the liquid flow tube holding member is certainly fixed with syringe body, the sealing efficiency between the syringe body and the liquid flow tube holding member is extremely improved, and the installment of the liquid flow tube holding member can be extremely easily released from the syringe body with small force, and besides, the whole structure of the syringe assembly is extremely simple, then its assembly and operation is extremely easy.

In addition to the effects above-mentioned, when the liquid flow tube holding member is installed in the syringe body, the groove or the projection of the holding member installing hole, comprising the sealing structure, annularly formed along a plane perpendicular to the axis center direction of the syringe body, is immediately engaged with the projection or the groove comprising the sealing structure, annularlay formed along the plane perpendicular to the axis center direction, of the liquid flow tube holding member linearly inserted in the axis center direction into the holding member installing hole, then the liquid flow tube holding member is positioned at a predetermined position. Therefore, the positioning of the liquid flow tube holding member in the holding member installing hole finishes by only inserting the liquid flow tube holding member without a special operation, and the sealing between the liquid flow tube holding member and the syringe body simultaneously finishes, then extremely speedy assembly is possible.

Of the present invention, the 2nd invention is the syringe assembly in the 1st invention, wherein the outside of the portion excluding said groove or said projection comprising said sealing structure of said member main body is smaller than the inner diameter of the portion corresponding to it of said holding member installing hole.

Therefore, the liquid flow tube holding member and the holding member installing hole can be contacted with each other only through the sealing structure. Then, in addition to the effects of the 1st invention, the liquid flow tube holding member is easily attached to and detached from the holding member installing hole, and the installing the liquid flow tube holding member at the time of assembly and the pulling the liquid flow tube member after use, such as the needle, into the syringe assembly can be smoothly and easily executed.

Of the present invention, the 3rd invention is the syringe assembly in the 1st invention, wherein said liquid flow tube holding member can be inserted into said holding member installing hole through said penetrating hole.

With this invention, in addition to the effects of the 1st invention, the liquid flow tube holding member can be installed in the holding member installing hole in such a state that the piston has been installed on the syringe body, then the possibility of entering dust or the like into the syringe body at the time of installation can be reduced, so it is sanitary.

Of the present invention, the 4th invention is the syringe assembly in the 3rd invention, wherein one or more than one slits are formed at a periphery of said penetrating hole.

With this invention, in addition to the effects of the 3rd invention, the liquid flow tube holding member can be easily inserted and installed in the holding member installing hole through the penetrating hole side, making use of the elastic deformation of the slits.

Of the present invention, the 5th invention is the syringe assembly in the 1st invention, wherein a needle body is directly connected with said member main body.

With this invention, in addition to the effects of the 1st invention, the member main body becomes to be so-called the hub for connecting needle, thereby the number of parts of the whole syringe assembly is extremely small, and the syringe assembly which whole structure is extremely simple is provided, and its assembly is further simple.

Of the present invention, the 6th invention is the syringe assembly in the 5th invention, wherein said holding member side engagement means and said needle body are communicated with each other.

With this invention, when the top end portion of the piston and the liquid flow tube holding member are engaged with each other through the holding member side engagement means by pressing the piston, the liquid, such as the medical injection, remaining near the holding member side engagement means is to be compressed between the top end portion of the piston and the liquid flow tube holding member. However, the liquid, which is to be oppressed, adequately flows and escapes to the needle body side communicating with the holding member side engagement member. That is, the liquid is extremely prevented from being compressed between the top end portion of the piston and the liquid flow tube holding member, thereby the top end portion of the piston and the liquid flow tube holding member can be engaged with each other with extremely small force, preferably.

Of the present invention, the 7th invention is the syringe assembly in the 1st invention, wherein a taper portion for connecting liquid flow tube member is formed on a top end side of said member main body, projecting in said axis center direction of said member main body.

With this invention, in the syringe assembly according to the 7th invention, a so-called hub comprising a member having a cone shape, for contacting the liquid flow tube member such as a needle, a tube for blood transfusion, a tube for intravenous drip can be installed in the taper for connecting liquid flow tube member. That is, the liquid flow tube member can be attached to and detached from the taper for connecting liquid flow tube member through the hub. Therefore, the change of the liquid flow tube member in the syringe assembly can be easily executed at the site by attachment or detachment of the taper for connecting liquid flow tube member and the hub while the liquid flow tube holding member is installed in the holding member installing hole, thereby the assembly and operation of the syringe assembly is further easy, in addition to the effects of the 1st invention.

Of the present invention, the 8th invention is the syringe assembly in the 7th invention, wherein a liquid flow tube member engagement portion surrounding a periphery of said taper portion for connecting liquid flow tube member of said member main body is provided.

With this invention, in addition to the effects of the 7th invention, when a so-called hub comprising a member having a cone shape, for contacting the liquid flow tube member such as a needle, a tube for blood transfusion, a tube for intravenous drip, is installed in the taper for connecting liquid flow tube member, the hub is engaged with the liquid flow tube member engagement portion, thereby the liquid flow tube member is certainly installed on the liquid flow tube holding member through the hub, preferably.

Of the present invention, the 9th invention is the syringe assembly in the 8th invention, wherein said liquid flow tube member engagement portion is a tapped hole for installation formed in the shape of a cylinder, open in said axis center direction of said member main body.

With this invention, in addition to the effects of the 8th invention, the liquid flow tube member is certainly installed on the liquid flow tube holding member through the hub by the screwed engagement between the hub and the tapped hole for installation, preferably.

Of the present invention, the 10th invention is the syringe assembly in the 4th invention, wherein said taper portion for connecting liquid flow tube member is formed on a top end side of said member main body, projecting in said axis center direction of said member main body.

With this invention, in the syringe assembly according to the 10th invention, a so-called hub comprising a member having a cone shape, for contacting the liquid flow tube member such as a needle, a tube for blood transfusion, a tube for intravenous drip can be installed in the taper for connecting liquid flow tube member. That is, the liquid flow tube member can be attached to and detached from the taper for connecting liquid flow tube member through the hub. Therefore, the change of the liquid flow tube member in the syringe assembly can be easily executed at the site by attachment or detachment of the taper for connecting liquid flow tube member and the hub while the liquid flow tube holding member is installed in the holding member installing hole, thereby the assembly and operation of the syringe assembly is further easy, in addition to the effects of the 4th invention.

Of the present invention, the 11th invention is the syringe assembly in the 7th invention, wherein a stopper portion comprised of projecting bodies is formed at an inner peripheral portion of said holding member installing hole, and an abutting portion in peripheral direction is provided at an outer peripheral portion of said member main body, projecting in a direction perpendicular to said axis center direction of said member main body such that when said member main body is installed in said holding member installing hole, an oscillation movement of said member main body in a peripheral direction with said axis center of said syringe body as its center can be prevented by the abutting in the peripheral direction between said abutting portion in peripheral direction and said stopper portion.

With this invention, in the syringe assembly according to the 11th invention, when a predetermined hub is installed on the liquid flow tube holding member installed in the syringe body through the taper for connecting liquid flow tube member, the member main body of the liquid flow tube holding member does not ocsillate in the peripheral direction of the member main body uniting with the hub by abutting the abutting portion in peripheral direction on the stopper portion in the peripheral direction even if it tries to do so. That is, the installation of the hub on the liquid flow tube holding member becomes to be easy.

Of the present invention, the 12th invention is the syringe assembly in the 8th invention, wherein a stopper portion comprised of projecting bodies is formed at an inner peripheral portion of said holding member installing hole, and an abutting portion in peripheral direction is provided at an outer peripheral portion of said member main body, projecting in a direction perpendicular to said axis center direction of said member main body such that when said member main body is installed in said holding member installing hole, an oscillation movement of said member main body in a peripheral direction with said axis center of said syringe body as its center can be prevented by the abutting in the peripheral direction between said abutting portion in peripheral direction and said stopper portion.

With this invention, in the syringe assembly according to the 12th invention, when a predetermined hub is installed on the liquid flow tube holding member installed on the syringe body through the taper for connecting liquid flow tube member and the liquid flow tube member engagement portion, the member main body of the liquid flow tube holding member is to oscillate in the peripheral direction to the syringe body, uniting with the hub when the hub and the liquid flow tube member engagement portion are engaged with each other. However, by abutting the abutting portion in peripheral direction on the stopper portion in the peripheral direction, the oscillation of the member main body in the peripheral direction is prevented. That is, the installation of the hub on the liquid flow tube holding member becomes to be easy.

Of the present invention, the 13th invention is the syringe assembly in the 1st invention, wherein said holding member side engagement means includes a groove formed penetrating said member main body in a direction perpendicular to said axis center direction of said member main body.

With this invention, in addition to the effects of the 1st invention, machining and forming the holding member side engagement means on the member main body is executed in such a manner that a groove is formed by penetrating the member main body, so it is easy. Besides, when the top end portion of the piston and the member main body are engaged with each other through the holding member side engagement means by pressing the piston, the liquid, such as a medical injection, remaining in the holding member side engagement means is to be compressed between the top end portion of the piston and the member main body. However, since the holding member side engagement means is the groove formed penetrating the member main body in the direction perpendicular to the axis center direction of the member main body, the liquid adequately flows in the direction perpendicular to the axis center direction of the member main body, in the direction far from the axis center through the holding member side engagement means which is a groove, and escapes to the side of the member main body. That is, the liquid remaining in the holding member side engagement means is prevented from being compressed between the top end portion of the piston and the member main body, thereby the engagement between the top end portion of the piston and the member main body can be executed with extremely small force, preferably.

Of the present invention, the 14th invention is the syringe assembly in the 1st invention, wherein a deformation expediting groove is provided with said member main body beside said holding member side engagement means at a direction perpendicular to said axis center direction of said member main body.

Therefore, the deformation near the holding member side engagement means of the member main body is extremely easy by the deformation expediting grooves. Then, in addition to the effects of the 1st invention, the engagement between the top end portion of the piston and the member main body through the holding member side engagement means to be executed by deforming the holding member side engagement means can be easily executed with extremely small force.

Of the present invention, the 15th invention is the syringe assembly in the 1st invention, wherein a piston side engagement means capable of engaging with said holding member side engagement means of said liquid flow tube holding member is provided with said piston, facing said holding member side engagement means.

With this invention, in addition to the effects of the 1st invention, the liquid flow tube holding member can be engaged with the piston side engagement means of the piston after use so as to be pulled out into the syringe body together with the liquid flow tube member, such as a needle. Therefore, only by pressing and pulling the piston, by the same operation as one of an usual syringe assembly, the needle or the like after use can be easily pulled in the syringe body, its operation is easy for everyone, there is no danger of error operation, and high safety is secured.

Of the present invention, the 16th invention is the syringe assembly in the 1st invention, wherein said piston is comprised such that a piston body can be bent and taken between an operation portion and liquid medicine press portion.

With this invention, in addition to the effects of the 1st invention, the liquid flow tube member, such as a needle, can remain in the inside of the syringe body being held with the top end portion of the piston by bending and taking the piston, thereby it is not operable from the outside. High safety is secured in case of disposal operation after that.

Of the present invention, the 17th invention is the syringe assembly in the 16th invention, wherein a piston stopper is provided with said syringe body so as not to pull said liquid medicine press portion of said piston out of said syringe body.

With this invention, in addition to the effects of the 16th invention, it is possible to prevent an operator from hurting with the used needle by inadvertently pulling the piston out of the syringe body when the piston is moved together with the needle. Therefore, high safety is secured.

Of the present invention, the 18th invention is the syringe assembly in the 16th invention, wherein a notch for bending and taking is formed at said piston body of said piston.

With this invention, the operation of bending and taking of the piston can be executed by making use of the notches.

Of the present invention, the 19th invention is the syringe assembly in the 18th invention, wherein said notch is formed so as to position at the end portion of said syringe body when said piston abuts on said piston stopper.

With this invention, the piston is pulled till it abuts on the piston stopper, and after that, the piston can be immediately bent and taken by making use of its end portion, and the operation of storing and remaining the needle in the syringe body can be successively executed. Therefore, the operations of injection and disposal can be effectively executed.

BRIEF DESCRIPTION OF THE DRAWINGS

FIG. 1 is a typical sectional view showing an example of a syringe assembly according to the present invention;

DESCRIPTION OF THE PREFERRED EMBODIMENT

Figure 2:
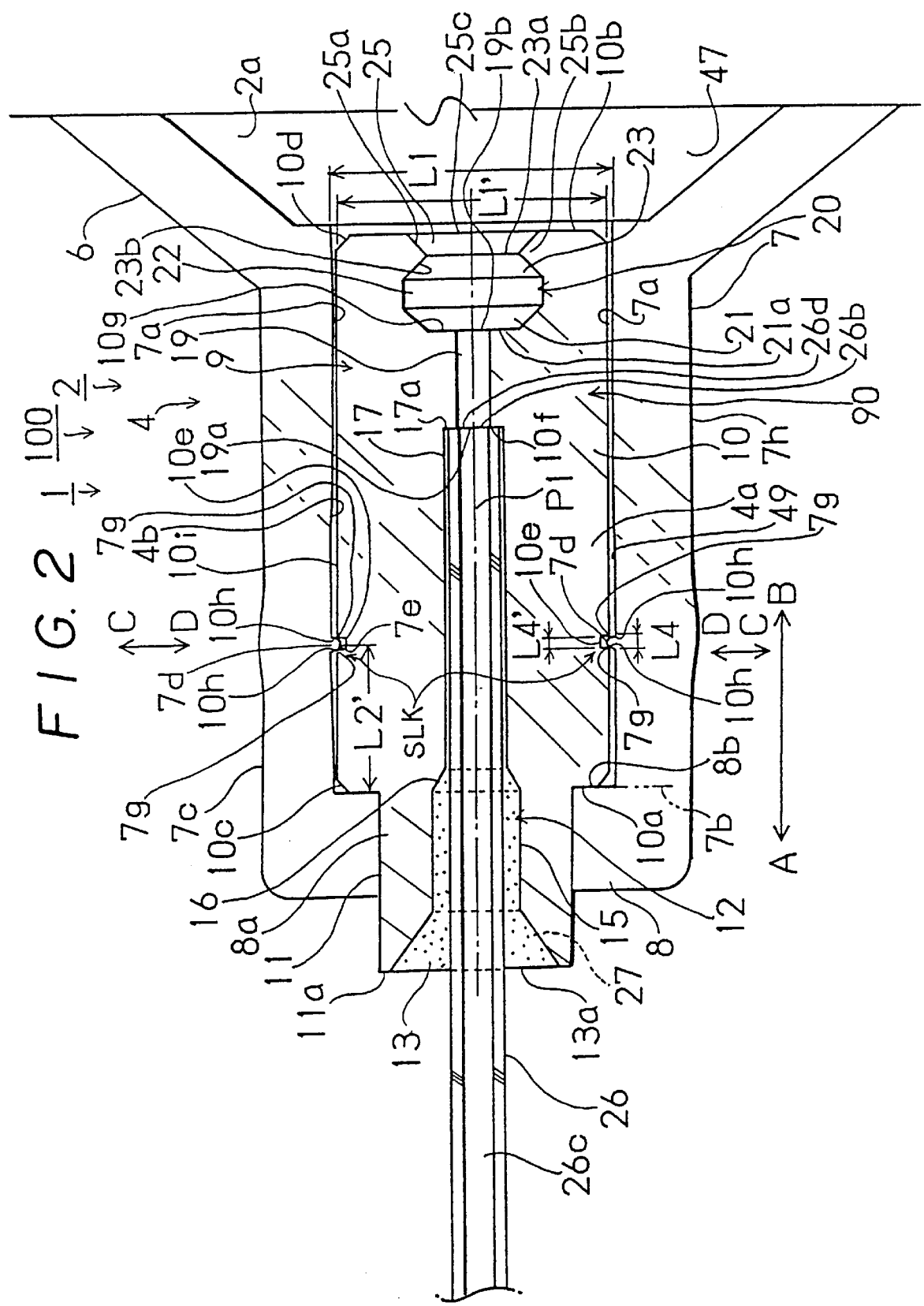
FIG. 2 is an enlarged sectional view in a portion near a hub of the syringe assembly as shown in FIG. 1.

Embodiments of the present invention will now be described hereinafter with respect to the accompanying drawings.

Figure 1:
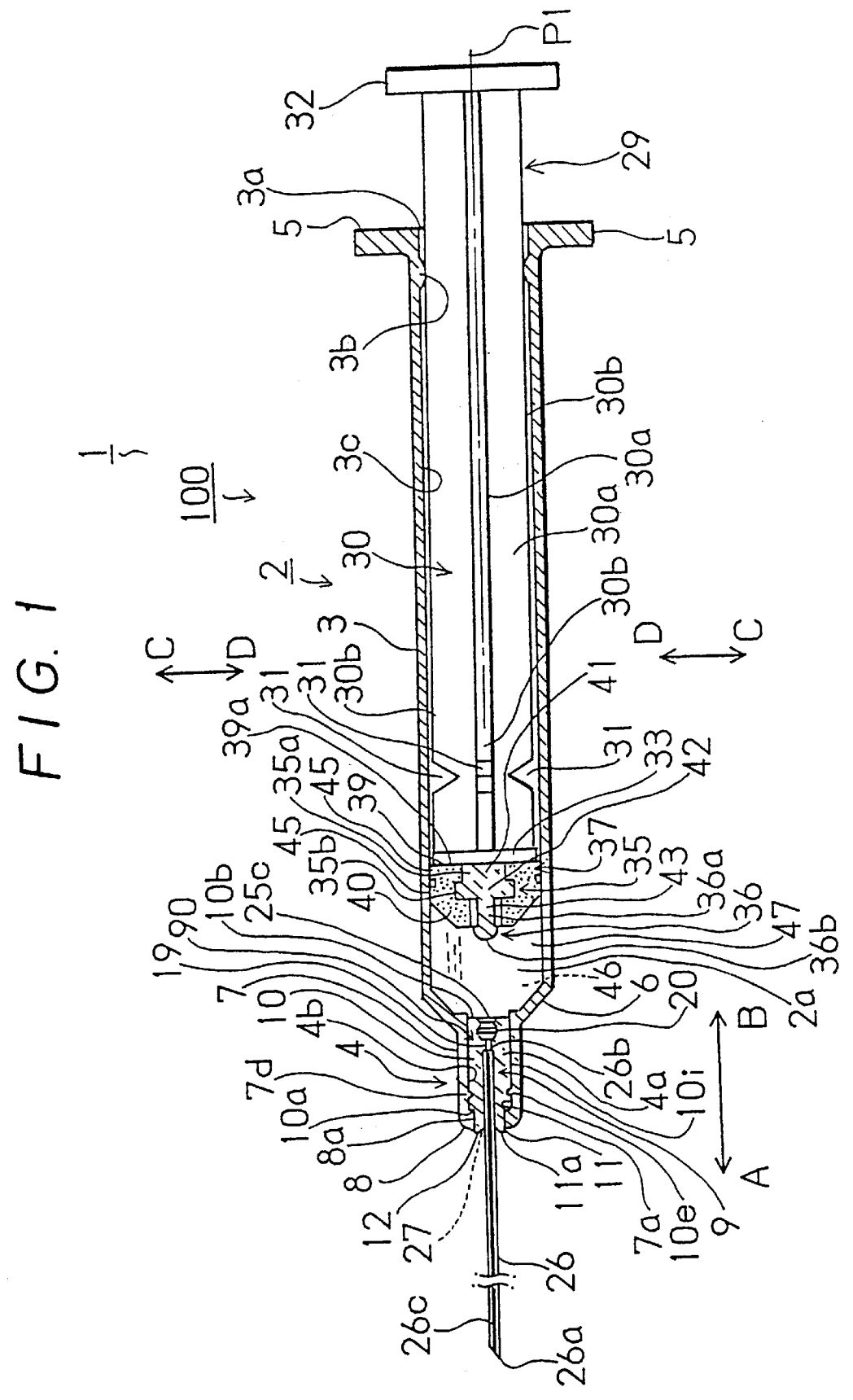

A syringe assembly 1 according to the present invention has a syringe 100 made of resin, as shown in FIG. 1. A syringe body 2 is provided with the syringe 100 (FIG. 1 is a typical cross section of the syringe assembly 1, but in a part of a piston 29, described hereinafter, its side, not the section, is shown for convenience.). A main cylindrical portion 3, cylindrically formed, is provided with the syringe body 2. A direction of an axis center of the main cylindrical portion 3, that is, the reciprocating directions parallel to an axis center P1 are an arrow A direction in the figure (or the left direction of the paper of FIG. 1) and an arrow B direction (or the right direction of the paper of FIG. 1).

At the outer periphery side of the main cylindrical portion 3, a syringe support 5, being in the shape of a plate, is provided near an opening end 3a of the arrow B side of the main cylindrical portion 3 (the right side of the paper of FIG. 1), forming a flange of the main cylindrical portion 3. Both plate faces of the syringe support 5 are perpendicular to the directions as shown by the arrows A and B. At an inner peripheral face 3c side of the main cylindrical portion 3, an engagement rib 3b, projecting in the direction for the axis center P1 of the main cylindrical portion 3, that is, the direction as shown by an arrow D of the figure, is annularly formed near the opening end 3a along the inner peripheral face 3c.

At the arrow A side of the main cylindrical portion 3 (the left side of the paper of FIG. 1) a taper 6 in the shape of a funnel is formed unitedly connecting with the main cylindrical portion 3. The inside diameter in the section perpendicular to the directions as shown by the arrows A and B of the taper 6 (that is, the circular section) is made narrower for the direction as shown by the arrow A.

The inside of the main cylindrical portion 3 and the inside of the taper 6 communicate with each other in the directions as shown by the arrows A and B, and the space combined both insides is an inside space 2a of the syringe body 2.

At the side of the arrow A of the taper 6, that is, at the side of the top of the syringe body 2, as shown in FIGS. 1 and 2, a hub insertion portion 4 is formed unitedly connecting with the taper 6, and is elastically deformed. A hub 9 made of resin, which is harder than the syringe 100, is provided with a hub insertion hole 4b of the hub insertion portion 4 elastically deformed as a liquid flow tube holding member.

Prior to the explanation of the hub insertion portion 4 elastically deformed, the hub insertion portion 4 in its natural form, which is not elastically deformed, and the hub 9 will now be respectively explained.

Figure 3:
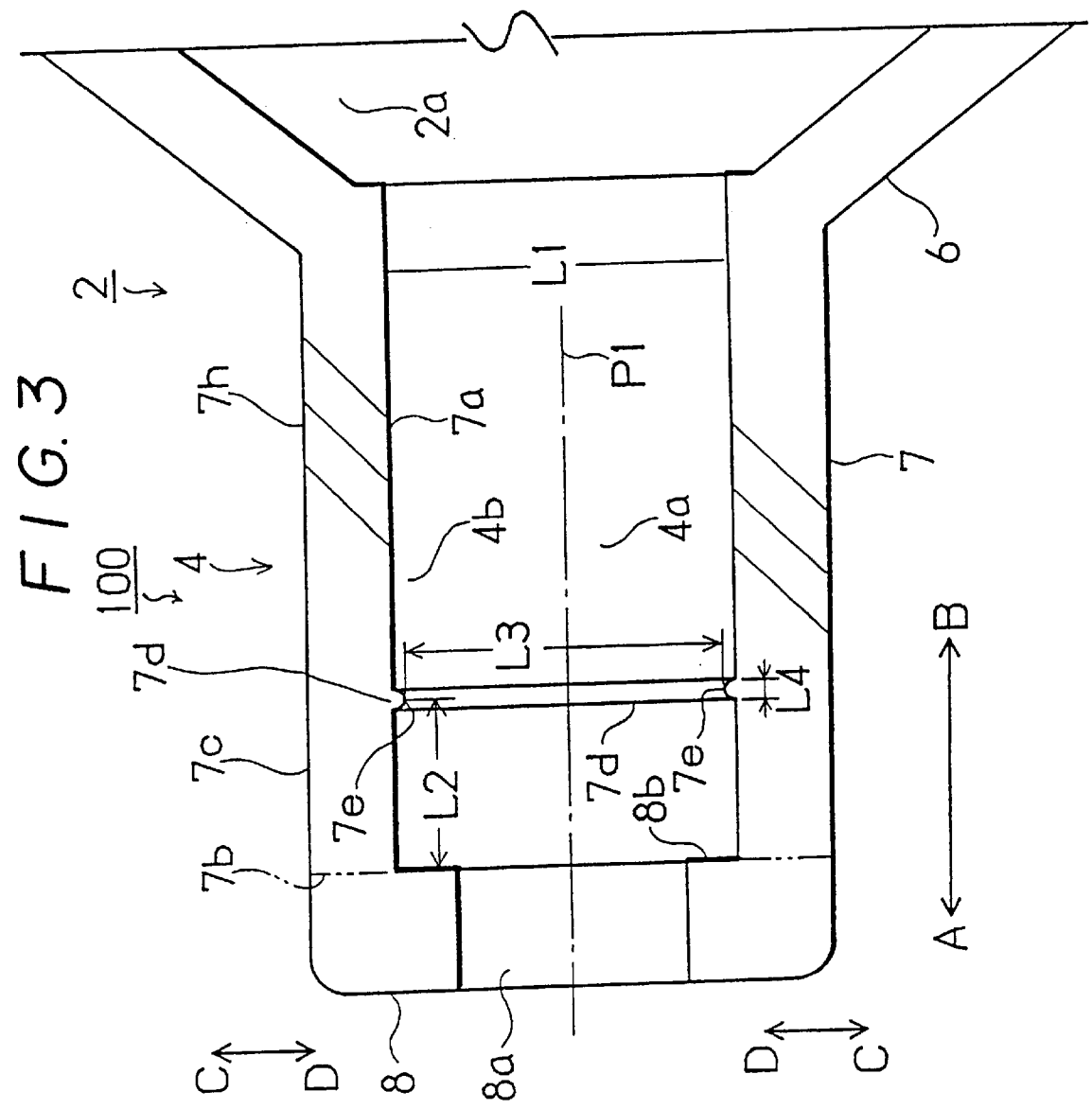
FIG. 3 is a view showing a portion near a hub insertion portion as shown in FIG. 2 in a natural state.

The hub insertion portion 4, which is not elastically deformed, as shown in FIG. 3, has a small cylindrical portion 7. The small cylindrical portion 7 is formed unitedly connecting with the taper 6. That is, the hub insertion portion 4 is formed unitedly connecting with the taper 6 in the small cylindrical portion 7. The small cylindrical portion 7 is formed coaxially with the main cylindrical portion 3. An inside diameter L1 of the small cylindrical portion 7 is smaller than one of the main cylindrical portion 3 (The inside diameter L1 of the small cylindrical portion 7 means one in the part where a hub stop rib 7d described hereinafter is not formed, of the inside diameter of the small cylindrical portion 7).

An inner peripheral face 7a side of the small cylindrical portion 7 is the hub insertion hole 4b. The hub stop rib 7d is formed in the hub insertion hole 4b, projecting for the axis center P1. The hub stop rib 7d is formed along the inner peripheral face 7a of the small cylindrical portion 7, along the circumference which center is the axis center P1, that is, annularly. Of the inside diameter of the small cylindrical portion 7, the inside diameter in a top end 7e of the hub stop rib 7d is inside diameter L3, and the width of the hub stop rib 7d in the directions as shown by the arrows A and B is width L4. The section of a flat surface including the axis center P1 of the hub stop rib 7d (that is, the section as shown in FIG. 3) is circular arc.

An end wall 8, being in the shape of a circular plate, is formed at the small cylindrical portion 7 such that the outside diameter of the end wall 8 is equal to one of the small cylindrical portion 7 and both front and back wall surfaces thereof are perpendicular to the directions as shown by the arrows A and B. The end wall 8 is provided being united with the small cylindrical portion 7 in such a manner that a wall face 8b of the end wall 8 at the arrow B side and an end portion 7b of the small cylindrical portion 7 at the arrow A side are in contact with each other. A circular hole 8a, which center is the axis center P1, is provided with the end wall 8 penetrating both front and back wall faces of the end wall 8 in the directions as shown by the arrows A and B.

Of the small cylindrical portion 7, the distance between the end portion 7b and the hub stop rib 7d in the directions as shown by the arrows A and B is L2. The portion corresponding to the distance L2 of the small cylindrical portion 7 (that is, the cylindrical portion) is an extendable portion 7c. The inside of the small cylindrical portion 7, that is, the inside of the hub insertion hole 4b is a hub insertion space 4a.

The hub insertion portion 4 in a natural state which is not elastically deformed is comprised as explained hereinbefore. The syringe 100 is comprised such that the syringe body 2 and the syringe support 5 are unitedly formed with each other. The syringe body 2 is comprised such that the main cylindrical portion 3, the taper 6, the hub insertion portion 4 are unitedly formed with one another.

On the other hand, the hub 9 has a hub body 90 as shown in FIG. 2. A main pillar portion 10, which longitudinal direction is parallel to the directions as shown by the arrows A and B, being in the shape of a cylinder which axis center is the axis center P1, is provided with the hub body 90. An outside diameter L1' of the main pillar portion 10 is smaller than the inside diameter L1 of the small cylindrical portion 7 in a natural state in the portion where no hub stop rib 7d exists, and is bigger than the inside diameter L3 in the top end 7e of the hub stop rib 7d of the small cylindrical portion 7. Chamfer portions 10c, 10d, in the shape of a taper, are respectively formed at the corner of the outer peripheral end side in an end face 10a of the main pillar portion 10 at the arrow A side (the left side of the paper of FIG. 2) and the corner of the outer peripheral end side in an end face 10b of the main pillar portion 10 at the arrow B side (the right side of the paper of FIG. 2).

A hub stop groove 10e is formed at the side of an outer peripheral face 10i of the main pillar portion 10. The hub stop groove 10e is annularly formed along the outer periphery side of the main pillar portion 10. The hub stop groove 10e is positioned at the position apart from the end face 10a of the main pillar portion 10 by a distance L2' in the direction as shown by the arrow B, and the distance L2' is slightly longer than the distance L2. Annular opening ends 10h, 10h are formed on the outer peripheral face 10i at the arrows A and B sides by provision of the hub stop groove 10e. A width L4' between the opening ends 10h and 10h in the directions as shown by the arrows A and B is narrower than the width L4 of the hub stop rib 7d of the small cylindrical portion 7.

A small pillar portion 11 is provided at the side of the end face 10a of the main pillar portion 10 extending in the directions as shown by the arrows A and B, being united with the main pillar portion 10, coaxial with the main pillar portion 10. The outside diameter of the small pillar portion 11 is smaller than the outside diameter L1' of the main pillar portion 10, and is slightly smaller than the inside diameter of the hole 8a provided on the end wall 8 of the small cylindrical portion 7 of the syringe body 2.

A needle insertion hole 12 is provided with the hub 9 as shown in FIG. 2. The needle insertion hole 12 is comprised of a first taper hole 13, a first cylindrical hole 15, a second taper hole 16 and a second cylindrical hole 17.

In the first taper hole 13, a circular opening 13a, which center is the axis center P1, is formed at an end face 11a of the small pillar portion 11 of the hub 9 at the arrow A side (the left side of the paper of FIG. 2), and the first taper hole 13 is formed orienting to the direction as shown by the arrow B from the end face 11a. The diameter of the section of the first taper hole 13 perpendicular to the directions as shown by the arrows A and B (that is, circular section which center is the axis center P1) is made narrower for the direction as shown by the arrow B.

The first cylindrical hole 15, in the shape of a cylinder, which center is the axis center P1, is provided with the hub 9 at the arrow B side of the first taper hole 13 (the right side of the paper of FIG. 2) connecting with the first taper hole 13.

The second taper hole 16 is provided with the hub 9 in the direction as shown by the arrow B at the arrow B side of the first cylindrical hole 15 connecting with the first cylindrical hole 15. The diameter of the section of the second taper hole 16 perpendicular to the directions as shown by the arrows A and B (the circular section which center is the axis center P1) is made narrower for the direction as shown by the arrow B.

The second cylindrical hole 17, in the shape of a cylinder, which center is the axis center P1, is provided with the hub 9 at the side of the arrow B of the second taper hole 16 connecting with the second taper hole 16. An end portion 17a at the side of the arrow B of the second cylindrical hole 17 reaches the inside of the main pillar portion 10. The end portion 17a of the second cylindrical hole 17 is in contact with a wall face 10f perpendicular to the directions as shown by the arrows A and B.

On the other hand, a flow hole 19 is provided with the main pillar portion 10 of the hub 9, adjacent to the second cylindrical hole 17 of the needle insertion hole 12 at the side of the arrow B (the right side of the paper of FIG. 2). The flow hole 19 is cylindrically provided such that the center is the axis center P1 and the diameter thereof is smaller than one of the second cylindrical hole 17. The flow hole 19 is provided connecting with the second cylindrical hole 17 of the needle insertion hole 12 such that an opening 19a, in the shape of a circular, is formed at the wall face 10f of the main pillar portion 10 (The needle insertion hole 12 may be formed in any forms in the hub body 90 as long as it is possible to connect with a medium holding space 47 described hereinafter.).

A piston engagement hole 20 is provided with the main pillar portion 10 of the hub 9, adjacent to the flow hole 19 at the side of the arrow B (the right side of the paper of FIG. 2.). The piston engagement hole 20 is comprised of a first taper hole 21, a cylindrical hole 22, a second taper hole 23 and a third taper hole 25.

The first taper hole 21 is provided adjacent to the flow hole 19 at the side of the arrow B (the right side of the paper of FIG. 2) in the main pillar portion 10 of the hub 9. The section of the first taper hole 21 perpendicular to the directions as shown by the arrows A and B is a circular section which center is the axis center P1. The diameter of the section of the first taper hole 21 is made bigger for the direction as shown by the arrow B. The diameter of an end portion 21a, being in the shape of a circular, of the first taper hole 21 at the side of the arrow A is bigger than one of the flow hole 19, that is, the end portion 21a is in contact with a wall face 10g perpendicular to the directions as shown by the arrows A and B. A circular opening 19b is formed at the wall face 10g by the flow hole 19, and the first taper hole 21 and the flow hole 19 communicate with each other through the opening 19b.

The cylindrical hole 22 being in the shape of a cylinder, which center is the axis center P1, is provided at the arrow B side of the first taper hole 21, connecting with the first taper hole 21. The second taper hole 23 is provided in the direction as shown by the arrow B at the side of the arrow B of the cylindrical hole 22, contacting with the cylindrical hole 22 such that the diameter of the section perpendicular to the directions as shown by the arrows A and B (that is, the circular section which center is the axis center P1) is made narrower for the direction as shown by the arrow B. The third taper hole 25 is provided in the direction as shown by the arrow B at the side of the arrow B of the second taper hole 23, contacting with the second taper hole 23, and the diameter of the section perpendicular to the directions as shown by the arrows A and B of the third taper hole 25 (the circular section which center is an axis center P2) is made bigger for the direction as shown by the arrow B. Then, a projection 25b is formed such that the part sandwitched between a wall face 23b facing the second taper hole 23 and a wall face 25a facing the third taper hole 25 of the main pillar portion 10 projects for the axis center P1 with a boundary portion 23a between the second taper hole 23 and the third taper hole 25 as an apex.

The arrow B side of the third taper hole 25 is open to the outside such that a circular opening 25c is formed at the end face 10b of the main pillar portion 10 of the hub 9.

The hub insertion portion 4 in a natural state, and the hub 9 are respectively comprised as shown before. The hub insertion portion 4 is elastically deformed as follows and the hub 9 is provided in the hub insertion hole 4b of the hub insertion portion 4 as follows.

Figure 4:
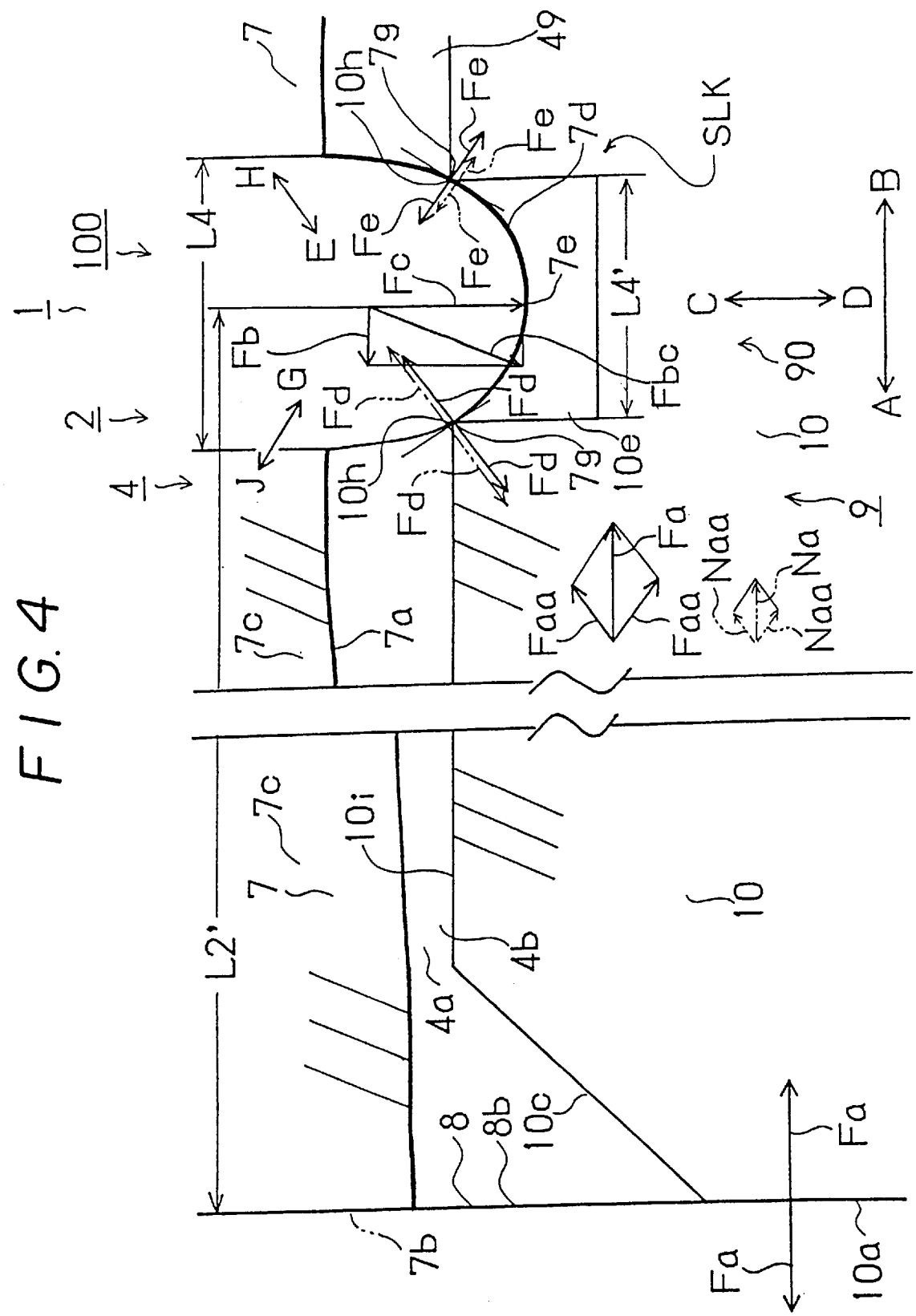
FIG. 4 is a view showing dynamical relation between the hub insertion portion and the hub as shown in FIG. 2.

That is, the hub insertion portion 4, as shown in FIG. 2 or FIG. 4, is elastically deformed in the hub stop rib 7d and near the hub stop rib 7d in the small cylindrical portion 7, expanding in the direction as shown by the arrow C in the figure, that is, for a direction centrifugal with respect to the axis center P1 and extending the extendable portion 7c of the small cylindrical portion 7 in the directions as shown by the arrows A and B (On this occasion, its deformed state is exaggeratedly expressed in the figure for easy understanding.).

On the other hand, the hub 9 is provided in such a manner that the main pillar portion 10 of the hub 9 is inserted into the hub insertion space 4a of the hub insertion portion 4 and the small pillar portion 11 of the hub 9 is inserted into the hole 8a of the end wall 8 so as to penetrate the hole 8a. The hub 9 is provided in such a manner that the end face 10a of the main pillar portion 10 of the hub 9 is closely contacted with the wall face 8b at the side of the arrow B of the end wall 8 (the right side of the paper of FIG. 2) (It is not necessary that the end face 10a and wall face 8b are always closely contacted with each other as the present embodiment, and a little gap may be formed therebetween.).

In addition, the hub 9 is provided such that the position of the hub stop rib 7d of the small cylindrical portion 7 and the position of the hub stop groove 10e of the hub 9 are matched in the directions as shown by the arrows A and B. In other words, the extendable portion 7c of the small cylindrical portion 7 extends in the directions as shown by the arrows A and B in such a manner that the distance between the end portion 7b of the small cylindrical portion 7 and the center of the hub stop rib 7d becomes to be the distance L2' (that is, the distance equal to the distance L2' between the end wall 10a in the hub 9 and the center of the hub stop groove 10e) by extending rather than the distance L2 in a natural state.

Furthermore, the hub 9 is provided such that the hub stop rib 7d abuts on the hub 9, and such that the top end 7e side of the hub stop rib 7d is inserted into the hub stop groove 10e which exists at the position corresponding and matching to the hub stop rib 7d in the direction as shown by the arrow D in the figure, that is, in the direction directing to the axis center P1 (that is, the opposite direction of one as shown by the arrow C). Since the width L4 of the hub stop rib 7d is wider than the width L4' of the hub stop groove 10e, as described before, the hub stop rib 7d abuts on the opening ends 10h, 10h at both sides of the arrows A and B of the hub stop groove 10e in seal portions 7g, 7g at the sides of the arrows A and B of the top end 7e as shown in FIG. 4.

That is, the hub insertion portion 4 expands in such a manner that the inside diameter in the seal portion 7g of the inside diameter of the small cylindrical portion 7 is almost equal to the outside diameter L1' of the hub 9.

The end face 10b of the main pillar portion 10 of the hub 9 is positioned near a boundary between the hub insertion space 4a and the inside space 2a (that is, near a boundary between the inside of the small cylindrical portion 7 and the inside of the taper 6).

The inside diameter excluding the hub stop rib 7d of the small cylindrical portion 7 which expands in the direction as shown by the arrow C is at least bigger than the inside diameter L1 in a natural state, and is bigger than the outside diameter L1' of the main pillar portion 10 of the hub 9. Therefore, the inner peripheral face 7a of the small cylindrical portion 7 is not in contact with the outer peripheral face 10i of the hub 9 in the part excluding the hub stop rib 7d, and a gap space 49 is formed between the inner peripheral face 7a and the outer peripheral face 10i.

Since the hub 9 is made of material harder than the syringe 100, it is hard to be elastically deformed, in comparison with the syringe 100. And, the hub 9 is hard to elastically deform in comparison with the syringe body 2 which is cylindrically formed since the hub 9 is in the shape of a circular cylinder. Therefore, the degree of elastic deformation of the hub 9 is smaller than the syringe 100.

Since the extendable portion 7c of the small cylindrical portion 7 extends in the directions as shown by the arrows A and B by elastic deformation, the extendable portion 7c gives the main pillar portion 10 of the hub 9 a restoring force Fa in the direction as shown by the arrow B from the end face 10a through the end wall 8 unitedly provided with the extendable portion 7c as shown in FIG. 4. Therefore, the main pillar portion 10 of the hub 9 gives the end wall 8 a reaction Fa' in the direction as shown by the arrow A against the restoring force Fa in the end face 10a. And, the extendable portion 7c gives the hub stop rib 7d which is unitedly provided with the extendable portion 7c a restoring force Fb in the direction as shown by the arrow A. The restoring force Fa is equal to the restoring force Fb.

Since the hub stop rib 7d and the part near the hub stop rib 7d expand by elastic deformation in the direction as shown by the arrow C, a restoring force Fc in the direction as shown by the arrow D is added to the hub stop rib 7d.

That is, a predetermined restoring force Fbc by the restoring forces Fb, Fc acts on the hub stop rib 7d in the direction for the axis center P1 and in the direction near one as shown by the arrow A, and the portions where the hub 9 and the hub stop rib 7d abut on each other at the sides of the arrow A and the arrow B (that is, each opening end 10h and each seal portion 7g at the sides of the arrow A and arrow B) match with each other by the restoring force Fbc such that seal pressure Fd, Fd and seal pressure Fe, Fe are added, that is, the abutting portions are sealed.

Then, the portion between the wall face 8b of the end wall 8 of the small cylindrical portion 7 and the end face 10a of the hub 9 and the portions between the seal portions 7g, 7g at the sides of the arrows A and B of the hub stop rib 7d and the opening ends 10h, 10h at the sides of the arrows A and B of the hub 9 are sealed, the portions are in a water-tight state (or an airtight state) (If a gap exists between the wall face 8b and the end face 10a of the hub 9, no restoring force Fa, Fb exist, and then only the portion between the hub stop rib 7d and the opening ends 10h, 10h are sealed.).

On this occasion, the restoring forces Fa, Fb, Fc or the restoring force Fbc by these restoring forces Fa, Fb, Fc can be preset in advance as a desired size according to the material of the hub insertion portion 4, the wall thickness of the small cylindrical portion 7 or the position of the hub stop rib 7d and the hub stop groove 10e.

The hub insertion portion 4 is elastically deformed as described before, and the hub 9 is provided with the hub insertion portion 4 as explained hereinbefore. And, the hub 9 is engaged with the hub insertion portion 4 by the engagement between the hub stop rib 7d and the hub stop groove 10e. That is, the hub stop rib 7d and the hub stop groove 10e comprise a predetermined sealing structure SLK.

On the other hand, a needle 26, which is the main body of the needle, is inserted into the needle insertion hole 12 of the hub 9, as shown in FIG. 1 or 2. A top end 26a side of the needle 26 is positioned at the outside of the syringe body 2, and the needle 26 is inserted into the needle insertion hole 12 from a rear end portion 26b side. That is, the main body of the needle is directly connected with the hub 9. The rear end portion 26b of the needle 26 abuts on the wall face 10f formed at the side of the arrow B of the needle insertion hole 12, and an opening 26d in the rear end 26b of a medium flow hole 26c which penetrates from the top end 26a of the needle 26 to the rear end 26b side is adjusted to the opening 19a of the flow hole 19 formed at the wall face 10f. That is, the medium flow hole 26c and the flow hole 19 communicates with each other through the openings 26d, 19a in the directions as shown by the arrows A and B.

Of the needle insertion hole 12, the space between the needle 26 and the hub 9 is filled with an adhesive 27, and is hardened.

The piston 29 is provided with the syringe assembly 1, as shown in FIG. 1 (FIG. 1 is a typical sectional view of the syringe assembly 1, and with respect to a piston body 30, an outer press plate 32, an inner press plate 33, which are described hereinafter, of the piston 29, their sides are shown, not their sections, for convenience.).

The piston 29 has the bar-shaped piston body 30 which extends in the directions as shown by the arrows A and B, the piston body 30 is comprised such that two congruent plate portions 30a, each which is a plate shaped rectangle especially long in the directions as shown by the arrows A and B, are unitedly cross provided with each other such that the sections thereof form the shape of a cross. The width perpendicular to the directions as shown by the arrows A and B of the plate face of the plate portion 30a is almost equal to the inside diameter in the engagement rib 3b of the main cylindrical portion 3, and the piston body 30 is inserted into the main cylindrical portion 3 through the opening end 3a from the arrow A side of the piston body 30.

On each plate portion 30a of the piston body 30, notches 31 are formed from both side portions 30b, 30b of respective plate portions 30a, 30a in the direction of the axis center (that is, the axis center P1) of the piston body in the shape of a wedge near the direction by the arrow A. Four notches 31 are provided at the positions adjusted one another in the directions as shown by the arrows A and B.

The outer press plate 32, which plate face is a circular plate perpendicular to the directions as shown by the arrows A and B, is provided at the end portion side of the arrow B side of the piston body 30, being united with the piston body 30, and coaxial with the piston body 30. The diameter of the outer press plate 32 is fully bigger than the inside diameter of the main cylindrical portion 3.

Figure 5:
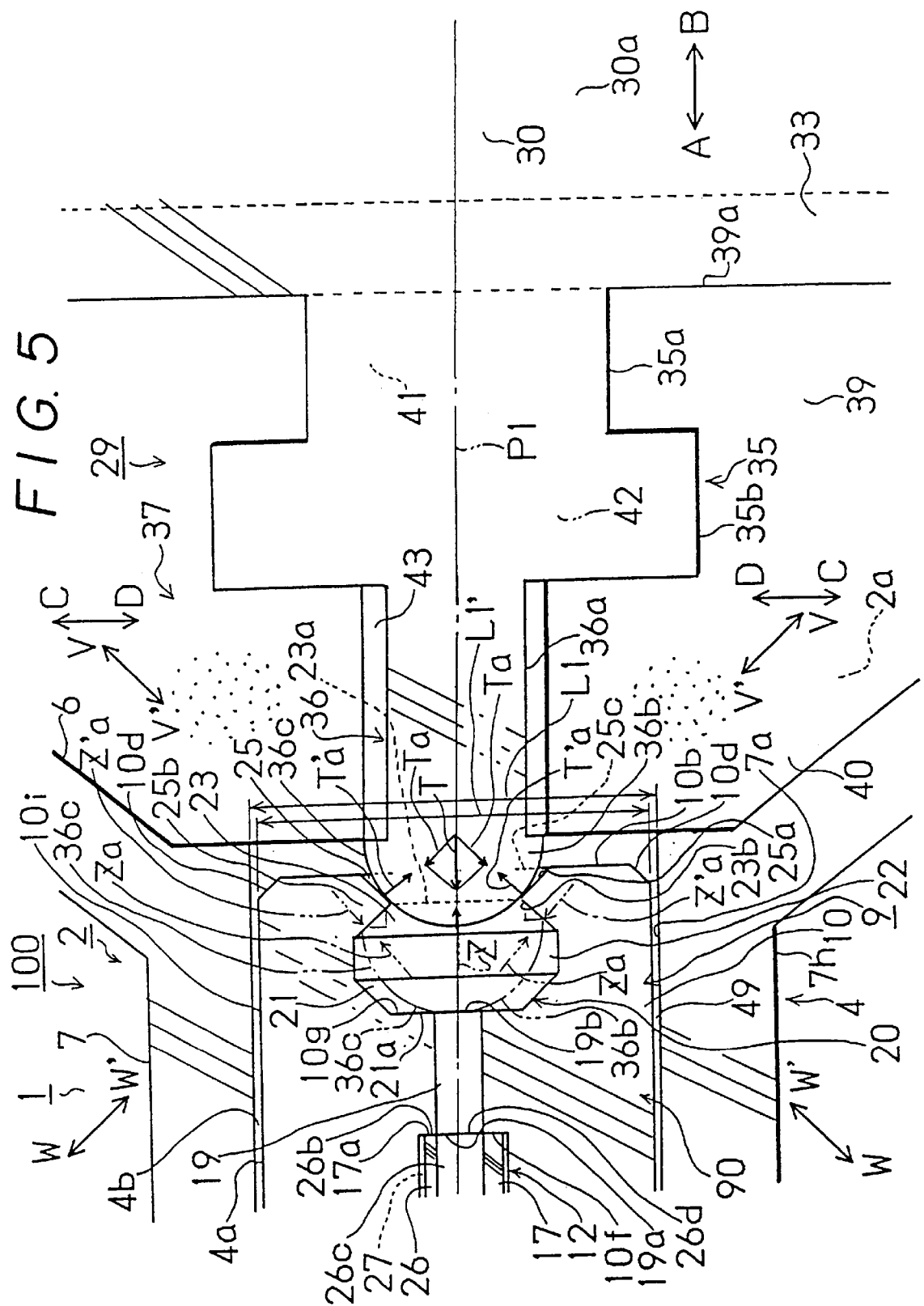
FIG. 5 is a view showing position relation between the hub and a piston as shown in FIG. 1.

As shown in FIG. 1 or 5, the inner press plate 33, which plate face is a circular plate perpendicular to the directions as shown by the arrows A and B, is provided at the end portion side of the arrow A side of the piston body 30 being united with the piston body 30 and coaxial with the piston body 30 (Therefore, the inner press plate 33 is positioned inside the main cylindrical portion 3.). The diameter of the inner press plate 33 is almost equal to the inside diameter of the main cylindrical portion 3 (Therefore, the diameter of the inner press plate 33 is bigger than the inside diameter in the engagement rib 3b of the main cylindrical portion 3.).

As shown in FIG. 1 or 5, a packing support 35 is provided with the inner press plate 33 at the arrow A side. A circular cylindrical portion 35a in the shape of a circular cylinder, which extends in the directions as shown by the arrows A and B, is provided with the packing support 35, coaxial with the inner press plate 33. The diameter of the circular cylindrical portion 35a is smaller than one of the inner press plate 33, and the circular cylindrical portion 35a is provided at the arrow A side of the inner press plate 33, being united with the inner press plate 33. A circular plate portion 35b, which plate face is a circular plate perpendicular to the directions as shown by the arrows A and B, is provided at the arrow A side of the circular cylindrical protion 35a, coaxial with the circular cylindrical portion 35a, united with the circular cylindrical portion 35a. The diameter of the circular plate portion 35b is bigger than one of the circular cylindrical portion 35a, and is smaller than one of the inner press plate 33.

A hub engagement portion 36 is provided at the arrow A side of the circular plate portion 35b, and a circular cylindrical portion 36a in the shape of a circular cylinder, which extends in the directions as shown by the arrows A and B, is provided with the hub engagement portion 36, coaxial with the circular plate portion 35b. The diameter of the circular cylindrical portion 36a is smaller than one of the circular plate portion 35b. The circular cylindrical portion 36a is provided at the arrow A side of the circular plate portion 35b, being united with the circular plate portion 35b. A semi-spherical insertion portion 36b, which diameter is bigger than one of the circular cylindrical portion 36a is provided at the arrow A side of the circular cylindrical portion 36a, united with the circular cylindrical portion 36a, directing a spherical surface 36c to the arrow A side.

The diameter of the circular cylindrical portion 36a is almost equal to the inside diameter of the boundary portion 23a between the second taper hole 23 and the third taper hole 25 of the piston engagement hole 20 provided at the hub 9, and the diameter of the insertion portion 36b is smaller than the inside diameter of the cylindrical hole 22 of the piston engagement hole 20.

On the other hand, a packing 37 made of flexible resin is supportingly provided with the packing support 35. The packing 37 is comprised of a circular cylindrical portion 39, which extends in the directions as shown by the arrows A and B, and a taper 40, connecting the arrow A side of the circular cylindrical portion 39, being united with the circular cylindrical portion 39. The outside diameter of the taper 40 is made narrower for the direction as shown by the arrow A. The form of the taper 40 allows the taper 40 to be inserted into the inside of the taper 6 of the syringe body 2 in a natural state so as to adjust to the inside of the taper 6.

A first hole 41, which diameter is the same as one of the circular cylindrical portion 35a of the packing support 35, and which length in the directions as shown by the arrows A and B is the same as one of the circular cylindrical portion 35a, is provided with the packing 37 in the direction as shown by the arrow A from an end face 39a side of the arrow B side of the circular cylindrical portion 39, coaxial with the circular cylindrical portion 39. Furthermore, a second hole 42, which diameter is the same as one of the circular plate portion 35b of the packing support 35, and which length in the directions as shown by the arrows A and B is the same as one of the circular plate portion 35b, is provided with the packing 37, connecting with the arrow A side of the first hole 41, coaxial with the circular cylindrical portion 39. And, a third hole 43, which diameter is the same as the outside diameter of the section perpendicular to the directions as shown by the arrows A and B of the insertion portion 36b of the hub engagement portion 36, and which length in the directions as shown by the arrows A and B is the same as one of the circular cylindrical portion 36a of the hub engagement portion 36 is provided with the packing 37, connecting with the arrow A side of the second hole 42, coaxial with the circular cylindrical portion 39. The third hole 43 is open at the taper 40 side of the packing 37 in the direction as shown by the arrow A.

In other words, the packing 37 is provided so as to engage with the packing support 35 such that the circular cylindrical portion 36a of the hub engagement portion 36 penetrates the third hole 43, the circular plate portion 35b of the packing support 35 is inserted into the second hole 42, and the circular cylindrical portion 35a of the packing support 35 penetrates the first hole 41.

In such a state that the taper 40 of the packing 37 is inserted into the inside of the taper 6 of the syringe body 2 in a natural state so as to adjust, as shown in FIG. 5, the form of the packing 37 is set in such a manner that the spherical surface 36c of the insertion portion 36b of the hub engagement portion 36 of the arrow A side of the packing support 35 which is engaged with the packing 37 is in contact with the wall face 25a facing the third taper hole 25 of the piston engagement hole 20.

The diameter of the circular cylindrical portion 39 of the packing 37 is almost equal to one of the inner press plate 33. However, at the outer periphery side of the circular cylindrical portion 39 of the packing 37, annular folds 45 are double formed, being arranged in the directions as shown by the arrows A and B along the outer periphery of the circular cylindrical portion 39. Then, the circular cylindrical portion 39 and the fold 45 of the packing 37 are inserted into the main cylindrical portion 3 of the syringe body 2, reducing their sizes by elastic deformation in the direction for the axis center P1 (that is, in the direction as shown by the arrow D.). That is, the circular cylindrical portion 39 of the packing 37 and the fold 45 press the inner peripheral face 3c of the main cylindrical portion 3 with a force in the direction away from the axis center (that is, the direction as shown by the arrow C), and the part between the packing 37 and the main cylindrical portion 3 is sealed with water seal (or air seal). Since the circular cylindrical portion 39 of the packing 37 applies a force to reduce the diameter of the first hole 41 and the second hole 42 to the first hole 41 side and the second hole 42 side of the packing 37, the packing support 35 inserted into the first hole 41 and the second hole 42 and the packing 37 closely contact with each other so as to be pressed. The part between the packing 37 and the packing support 35 is sealed with water seal (or air seal).

The inner peripheral face 3c of the main cylindrical portion 3 of the syringe body 2 is smoothly formed, and then, the piston 29, into which the packing 37 is inserted, is slidable in the directions as shown by the arrows A and B in the inside space 2a of the main cylindrical portion 3.

The syringe assembly 1 is comprised as described hereinbefore. In order to assemble the syringe assembly 1, the following steps are executed.

That is, the syringe 100, the hub 9, the needle 26, the piston 29 and the packing 37, which are the comprising parts of the syringe assembly 1, are prepared. At first, the hub 9 is inserted into the syringe 100.

Figure 6:
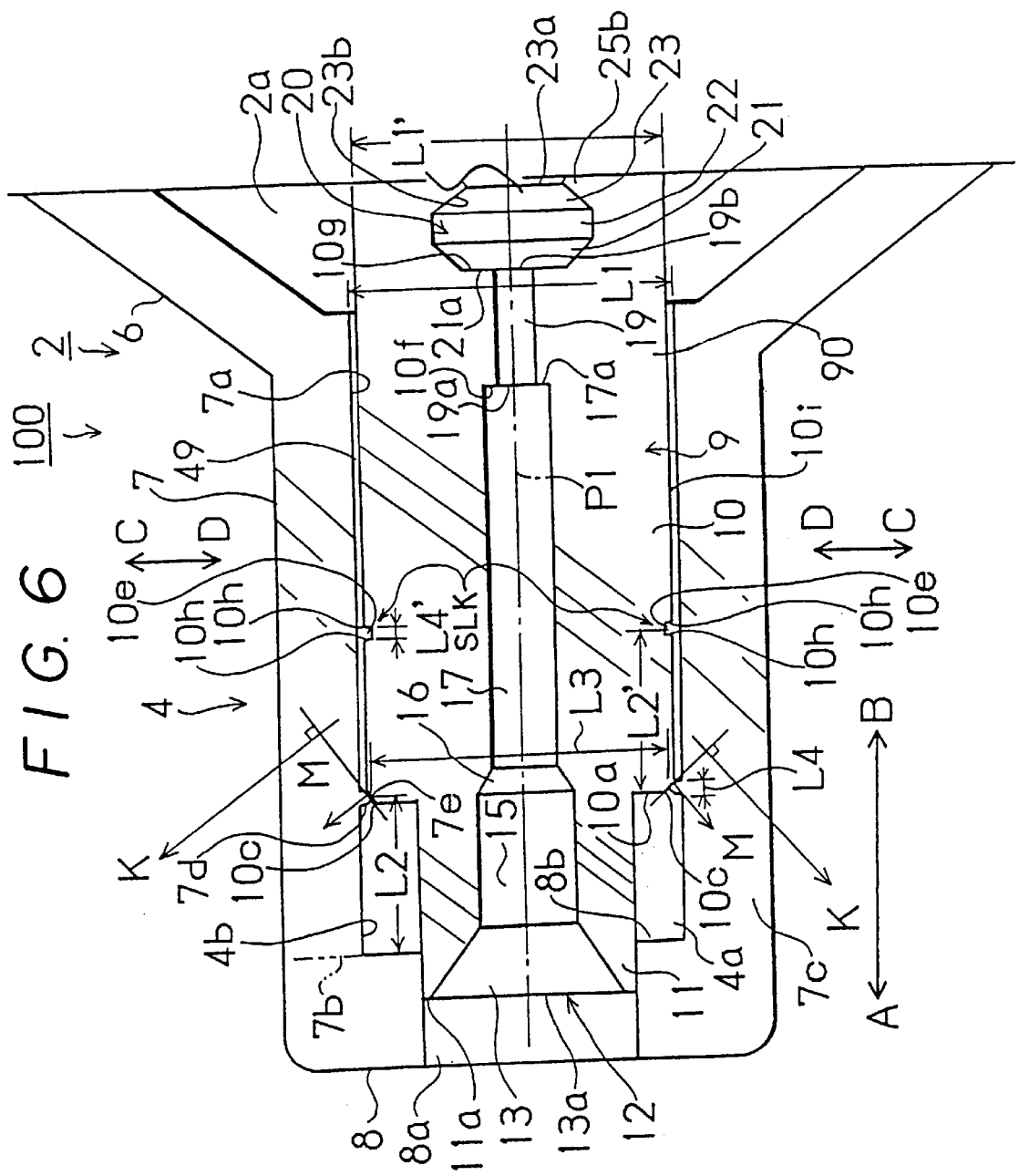
FIG. 6 is a view showing a routine of inserting the hub into the hub insertion portion as shown in FIG. 2.

That is, the hub 9 is inserted into the inside space 2a of the syringe body 2 from the opening end 3a of the syringe body 2. The insertion is executed so as to face the small pillar portion 11 side of the hub 9 to the small cylindrical portion 7 side of the syringe body 2 (the side of the arrow A of the figure). Subsequently, the hub 9 is further inserted into the side of the arrow A of the figure as shown in FIG. 6, and the hub 9 is inserted into the inside of the small cylindrical portion 7 of the syringe body 2, that is, into the hub insertion space 4a to the position at which the chamfer portion 10c of the hub 9 abuts on the hub stop rib 7d having the inside diameter smaller than the outside diameter L1' of the main pillar portion 10 of the hub 9. On this occasion, since the outside diameter L1' of the main pillar portion 10 of the hub 9 and the outside diameter of the small pillar portion 11 (that is, the outside diameter smaller than the outside diameter L1') are smaller than the inside diameter L1 of the part in which the hub stop rib 7d is not formed of the small cylindrical portion 7, the hub 9 is smoothly inserted into the hub insertion space 4a of the small cylindrical portion 7 to the position at which the chamfer portion 10c of the hub 9 abuts on the hub stop rib 7d having the inside diameter L3 smaller than the inside diameter L1'.

While the hub 9 is inserted to the position at which the chamfer portion 10c of the hub 9 abuts on the hub stop rib 7d, the end face 11a of the arrow A side of the small pillar portion 11 of the hub 9 reaches the position of the wall face 8b of the arrow B side of the end wall 8 of the hub insertion portion 4. However, since the hole 8a of the end wall 8 is at the position corresponding to the small pillar portion 11 in the directions as shown by the arrows C and D, and its diameter is bigger than one of the small pillar portion 11, the end face 11a reaches the hole 8a so as to adjust when the end face 11a of the small pillar portion 11 reaches the wall face 8b of the end wall 8. That is, the hub 9 is inserted to the position at which the chamfer portion 10c of the hub 9 abuts on the hub stop rib 7d, thereby the small pillar portion 11 is smoothly inserted into the hole 8a of the end wall 8.

After the chamfer portion 10c abuts on the hub stop rib 7d, as shown in FIG. 6, a force in the direction as shown by the arrow A is added to the hub 9 from the end portion 10b side of the arrow B side of the hub 9. The force in the direction as shown by the arrow A is added to the hub 9, thereby the hub 9 gives an action force M to the hub stop rib 7d at the position at which the chamfer portion 10c abuts on the hub stop rib 7d in the direction perpendicular to the tapered surface of the chamfer portion 10c, that is, in the direction as shown by the arrow K in the figure.

Of the action force M, the component force of a component of the direction as shown by the arrow A is balanced in the hub stop rib 7d and the like as shearing stress or bending stress. Of the action force M, the component force of the component in the direction as shown by the arrow C presses the small cylindrical portion 7 through the hub stop rib 7d in the direction as shown by the arrow C. The small cylindrical portion 7 is easy to be elastically deformed against the force in the direction as shown by the arrow C for its construction, and therefore, the small cylindrical portion 7 expands at the hub stop rib 7d and near the hub stop rib 7d in the direction as shown by the arrow C by the component force of the component in the direction as shown by the arrow C of the action force M.

Since the hub stop rib 7d of the small cylindrical portion 7 and the portion near the hub stop rib 7d expand in the direction as shown by the arrow C, the inside diameter in the hub stop rib 7d of the small cylindrical portion 7 is broadened, and the hub 9 receiving the force pressing in the direction as shown by the arrow A advances in the direction as shown by the arrow A as the inside diameter is broadened. At the position at which the hub 9 advances in the direction as shown by the arrow A, the hub 9 further presses the hub stop rib 7d in the chamfer portion 10c, and the hub stop rib 7d of the small cylindrical portion 7 and the part near the hub stop rib 7d further expand in the direction as shown by the arrow C by the component force of the component in the direction as shown by the arrow C of the force pressing the hub stop rib 7d. The inside diameter in the hub stop rib 7d of the small cylindrical portion 7 is further broadened, the hub 9 receiving the force pressing in the direction as shown by the arrow A further advances in the direction as shown by the arrow A as the inside diameter is broadened. Furthermore, the hub 9 is advanced in the direction as shown by the arrow A while the force in the direction as shown by the arrow A is added to the hub 9 and the hub stop rib 7d and the part near the hub stop rib 7d are further expanded in the direction as shown by the arrow C. Then, the hub 9 is advanced to the position at which the hub stop rib 7d abuts on the hub 9 at the nearest side to the arrow B of the chamfer portion 10c, that is, in the outer peripheral face 10i of the main pillar portion 10.

Figure 7:
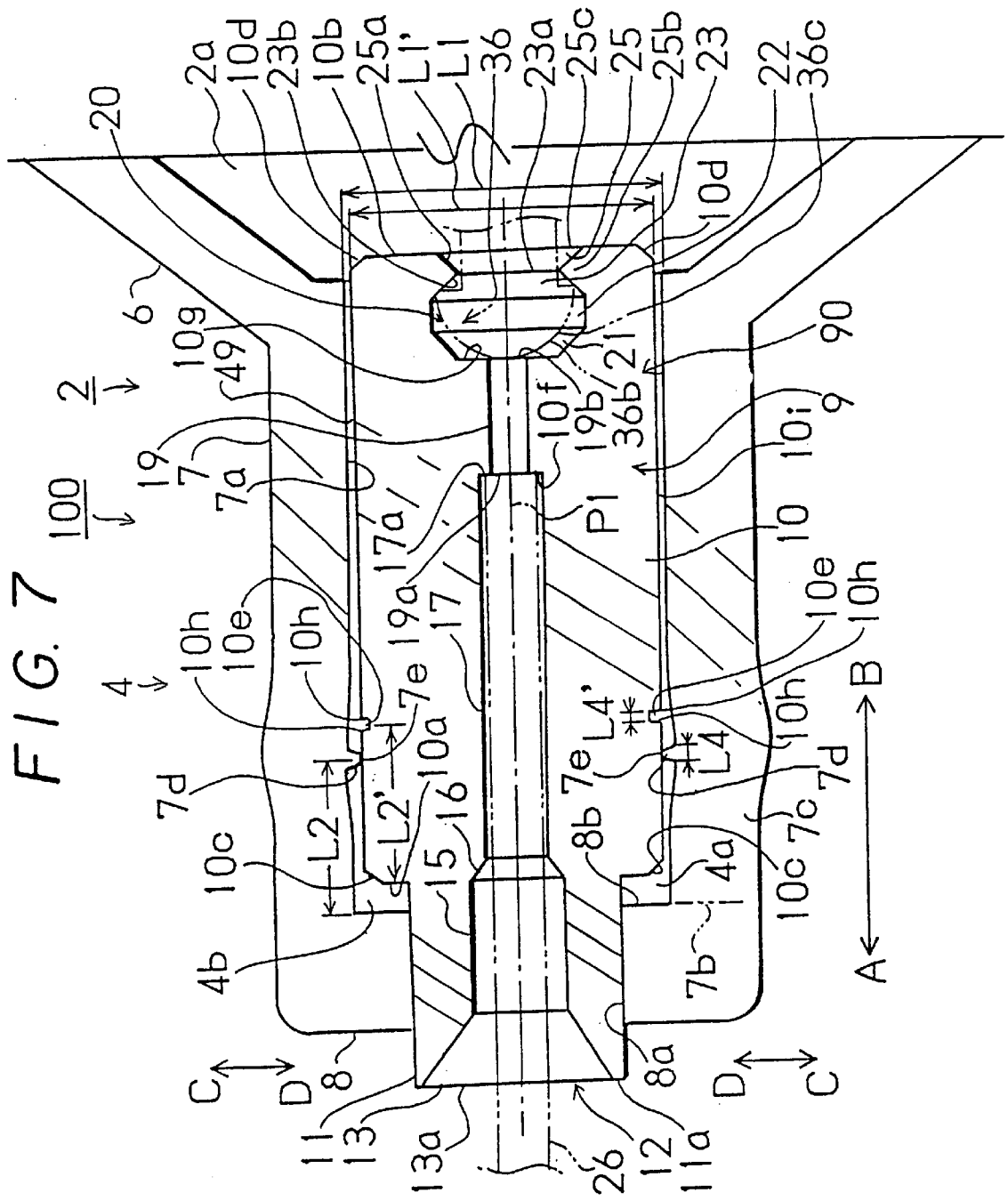
FIG. 7 is a view showing a routine of inserting the hub into the hub insertion portion as shown in FIG. 2.

The hub 9 advances to the position at which the hub stop rib 7d abuts on the outer peripheral face 10i of the main pillar portion 10, thereby the restoring force restoring the hub stop rib 7d and the portion near the hub stop rib 7d in the direction as shown by the arrow D is added to the main pillar portion 10 in the outer peripheral face 10i through the hub stop rib 7d at the portion abutting the hub stop rib 7d and the outer peripheral face 10i on each other, as shown in FIG. 7. Therefore, when the hub 9 is further advanced in the direction as shown by the arrow A adding a force in the direction as shown by the arrow A at the position at which the hub stop rib 7d abuts on the outer peripheral face 10i of the main pillar portion 10, a frictional force acts on the hub 9 in the direction as shown by the arrow B by the force acting on the hub 9 in the outer peripheral face 10i in the direction as shown by the arrow D. That is, the hub 9 is further advanced in the direction as shown by the arrow A adding a force in the direction as shown by the arrow A being capable of resisting the frictional force. The hub 9 is further advanced in the direction as shown by the arrow A until the end face 10a of the main pillar portion 10 of the hub 9 is closely contacted with the wall face 8b of the arrow B side of the end wall 8.

After the hub 9 is advanced till close contact, furthermore, the hub 9 is pressed in the direction as shown by the arrow A. By the press the hub 9 gives the end wall 8 closely contacting with the arrow A side of the hub 9 a force in a direction as shown by the arrow A, and the force is transferred to the extendable portion 7c of the small cylindrical portion 7 being unitedly provided with the end wall 8 (and each portion of the remaining syringe body 2). Therefore, the extendable portion 7c extends in its length in the directions as shown by the arrows A and B by elastic deformation. Furthermore, the press is continued so as to extend the extendable portion 7c, and the press is continued till the distance between the wall face 8b of the end wall 8 and the hub stop rib 7d in the directions as shown by the arrows A and B becomes to be the distance L2' from the distance L2.

With the extending of the extendable portion 7c, the hub stop rib 7d moves relative to the hub 9 at the arrow B side along the outer peripheral face 10i of the hub 9 and the distance between the wall face 8a of the end wall 8 and the hub stop rib 7d becomes to be the distance L2', thereby the position of the hub stop rib 7d and the position of the hub stop groove 10e of the hub 9 are adjusted to each other. Since a restoring force in the direction as shown by the arrow D is acted on the hub stop rib 7d and the portion near the hub stop rib 7d, the position of the hub stop rib 7d and the position of the hub stop groove 10e are adjusted to each other, thereby the hub stop rib 7d and the portion near the hub stop rib 7d slightly restore in the direction as shown by the arrow D, inserting the top end 7e side of the hub stop rib 7d into the hub stop groove 10e in the direction as shown by the arrow D (In this case, both can not restore to their natural state.). And, the top end 7e side of the hub stop rib 7d is inserted into the hub stop groove 10e in the direction as shown by the arrow D, thereby the hub stop rib 7d is engaged with the hub 9, abutting on the opening ends 10h, 10h of both A and B sides of the hub stop groove 10e. The portions abutting on the opening ends 10h, 10h of the hub stop rib 7d are the seal portions 7g, 7g, as described before.

Then, the insertion of the hub 9 into the syringe 100 finishes. As described before, the hub 9 is fixed by the small cylindrical portion 7 balancing respective forces between the hub 9 and the small cylindrical portion 7, as described hereinbefore.

The insertion operation of the hub 9 into the syringe 100 is executed by pressing the hub 9 so as to insert, and then, it is easy without complex assembling operations.

Subsequently, the packing 37 is inserted into the piston 29. In the first place, the first hole 41 of the packing 37 is broadened with hands or the like so as to equalize the diameter of the first hole 41 with one of the circular plate portion 35b of the packing support 35, making use of the flexibility of the packing 37. After that, the hub engagement portion 36 side of the piston 29 is inserted in the direction as shown by the arrow A from the first hole 41 side of the packing 37. Next, the piston 29 is further inserted until the insertion portion 36b of the hub engagement portion 36 passes and penetrates the third hole 43 of the packing 37 in the direction as shown by the arrow A and the insertion portion 36b projects at the side of the arrow A of the taper 40 of the packing 37, that is, the circular cylindrical portion 36a of the hub engagement portion 36 is inserted into the third hole 43 and the circular cylindrical portion 35a of the packing support 35 and the circular plate portion 35b are inserted into the first hole 41 and the second hole 42 which are respectively broadened.

After that, the hand by which the first hole 41 is broadened is left therefrom so as to return the packing 37 to its natural state, thereby the insertion of the packing 37 is finished.

Subsequently, the piston 29, into which the packing 37 is inserted, is inserted into the syringe body 2.

The insertion of the piston 29 is executed in such a manner that the side, at which the packing 37 of the piston 29 is inserted, is inserted into the inside space 2a of the syringe body 2 from the opening end 3a side of the syringe body 2.

On this occasion, the outside diameter in the fold 45 of the circular cylindrical portion 39 of the packing 37 in a natural state is bigger than the inside diameter of the main cylindrical portion 3 of the syringe body 2. However, the packing 37 can be inserted into the inside space 2a of the syringe body 2 by reducing the outside diameter of the fold 45 of the packing 37 making use of the flexibility of the packing 37.

That is, the taper 40 side of the packing 37 is adjusted to the opening end 3a, and after that, the piston 29 is pressed in the direction as shown by the arrow A, thereby the packing 37 is inserted into the inside space 2a of the syringe body 2, adjusting to the inside space 2a of the syringe body 2, that is, reducing the outside diameter of the fold 45 of the circular cylindrical portion 39 of the packing 37.

Since the outside diameter of the inner press plate 33 and the width of the plate portion 30a of the piston body 30 are almost equal to the inside diameter of the main cylindrical portion 3 of the syringe body 2 (or smaller), the inner press plate 33 and the piston body 30 are smoothly inserted into the inside space 2a of the syringe body 2.

By inserting the piston 2 into the direction as shown by the arrow A, the packing 37 and the inner press plate 33 pass the position of the engagement rib 3b of the main cylindrical portion 3.

When the packing 37 passes the position of the engagement rib 3b, the packing 37 receives the reaction against the force pressing the piston 29 in the direction as shown by the arrow A from the engagement rib 3b, and passes reducing the outside diameter of the circular cylindrical portion 39 and the fold 45 so as to equalize with the inside diameter of the engagement rib 3b of the main cylindrical portion 3 of the syringe body 2 by the reaction.

When the inner press plate 33 passes the position of the engagement rib 3b continuing the packing 37, the periphery side of the inner press plate 33, which outside diameter is bigger than the inside diameter of the engagement rib 3b, abuts on the engagement rib 3b. In case of abutting, the force pressing the piston 29 in the direction as shown by the arrow A elastically expands the portion near the engagement rib 3b of the main cylindrical portion 3 in the direction as shown by the arrow C through the inner press plate 33, and through the engagement rib 3b abutting on the inner press plate 33. Therefore, the inner press plate 33 passes the position of the engagement rib 3b, broadening the inside diameter in the engagement rib 3b. After the passing, the inner press plate 33 leaves from the engagement rib 3b, and then, no force expanding the main cylindrical portion 3 in the direction as shown by the arrow C acts, and the portion near the engagement rib 3b of the main cylindrical portion 3 restores in the direction as shown by the arrow D.

After the packing 37 and the inner press plate 33 pass the position of the engagement rib 3b of the main cylindrical portion 3, the piston 29 is further inserted in the direction as shown by the arrow A, and the piston 29 is inserted to the position, at which the taper 40 of the packing 37 is inserted into the inside of the taper 6 of the syringe body 2 so as to adjust, and then, the insertion of the piston 29 finishes.

In such a state that the taper 40 of the packing 37 is inserted into the inside of the taper 6 of the syringe body 2 so as to adjust, as described hereinbefore, the insertion portion 36b of the hub engagement portion 36 of the piston 29 exists in such a manner that the spherical surface 36c side of the insertion portion 36b is in contact with the wall face 25a facing the third taper hole 25 of the piston engagement hole 20, which is provided with the hub 9.

Subsequently, the needle 26 is inserted into the needle insertion hole 12 of the hub 9 so as to attach. That is, the needle 26 is inserted from the rear end 26b side of the needle 26 into the needle insertion hole 12 in the direction as shown by the arrow B, as shown in FIG. 2 till the rear end 26b abuts on the wall face 10f of the hub 9 of the bottom of the needle insertion hole 12. After the insertion, the space between the hub 9 in the needle insertion hole 12 and the needle 26 is filled with the adhesive 27, and then, the adhesive 27 is hardened. Then, insertion of the needle 26 in the hub 9 finishes.

When the needle insertion hole 12 is filled with the adhesive 27, the adhesive 27 can flow to the bottom side of the needle insertion hole 12 (that is, the arrow B side) without forming a space in the needle insertion hole 12 to the utmost by the first taper hole 13 and the second taper hole 16 which are provided with the needle insertion hole 12.

Assembly of the syringe assembly 1 finishes by the end of insertion of the needle 26.

As described hereinbefore, most operations in assembly of the syringe assembly 1 (that is, all operations excluding one for insertion of the needle 26) are executed by pressing, and therefore, the assembly of the syringe assembly 1 is easy without complex operations.

The syringe assembly 1 assembled as shown before, is used and, after that, the syringe assembly 1 is discarded as follows.

At first, the syringe assembly 1 assembled is filled with a liquid injection medium 46. Filling of the injection medium 46 is executed in such a manner that the main cylindrical portion 3 of the syringe body 2 of the syringe assembly 1 is grasped and supported with one hand, and the top end 26a of the needle 26 of the syringe assembly 1 is inserted into the injection medium 46 which is inside of a medicine bottle (not shown), and after that, the piston 29 is pulled out to the syringe body 2 in the direction as shown by the arrow B being grasped the outer press plate 32 of the piston 29 with the other hand.

Of the inside space 2a of the syringe body 2, the space at the side of the arrow A rather than the packing 37 or the hub engagement portion 36, that is, the medium holding space 47 communicates with the outside of the top end 26a side of the needle 26, that is, inside of a medicine bottle (not shown) through the medium flow hole 26c of the needle 26, the flow hole 19 and the piston engagement hole 20 of the hub 9 in the directions as shown by the arrows A and B. And, the medium holding space 47 is broadened by pulling the piston 29 to the syringe body 2 in the direction as shown by the arrow B, and then, the pressure of the air of the medium holding space 47 (or the injection medium 46) is lowered. Therefore, a differencial pressure arises between the medium holding space 47 and the outside of the top end 26a side of the needle 26, that is, inside of the medicine bottle (not shown), and the injection medium 46 in the medicine bottle flows in the medium holding space 47 through the medium flow hole 26c of the needle 26, and the flow hole 19 and the piston engagement hole 20 of the hub 9.

Filling of the injection medium 46 finishes in such a manner that the piston 29 is further pulled to the syringe body 2 in the direction as shown by the arrow B so as to further broaden the medium holding space 47 and so as to stream a predetermined amount of the injection medium 46 into the medium holding space 47 (The medium holding space 47 may be filled with the injection medium 46, which amount is slightly more than a predetermined amount, and after that, the air or surplus injection medium 46 and the like in the medium holding space 47 may be expelled to the outside through the needle 26 and the like by pressing the piston 29 to the syringe body 2 in the direction as shown by the arrow A with the syringe assembly 1 supported directing the needle 26 side to the upper.).

On this occasion, differencial pressure arises between the medium holding space 47 and the outside of the medium holding space 47 at the time of filling of the injection medium 46, and therefore, a differencial pressure force Na acts on the hub 9, which separates the medium holding space 47 from the outside of the medium holding space 47 in the direction as shown by the arrow B, as shown by two-dot chain line of FIG. 4.

A predetermined restoring force Fbc is set so as not to respectively disengage the seal portions 7g, 7g of both sides of the arrows A and B from the opening ends 10h, 10h so that both seal pressure Fd and Fe, as shown by the two-dot chain line in FIG. 4, which respectively act between the seal portions 7g, 7g and the opening ends 10h, 10h at both sides of the arrows A and B, may not become to be zero or minus if the most differencial pressure force Na potential acts.

Then, the injection medium 46 in the medium holding space 47 flows in the hub insertion space 4a of the hub insertion portion 4, and furthermore, to the gap space 49 between the hub 9 and the small cylindrical portion 7 from the hub insertion space 4a. However, since the portion between the seal portion 7g of the arrow B side of the hub stop rib 7d and the opening end 10h of the arrow B side of the hub 9 is sealed, the injection medium 46 passes between the seal portion 7g of the arrow B side and the opening end 10h and does not leak in the arrow A side and the like of the hub stop rib 7d. In addition, since not only one portion between the seal portion 7g of the arrow B side and the opening end 10h, the portion between the seal portion 7g of the arrow A side and the opening end 10h, and the portion between the end wall 8 and the end face 10a of the hub 9 are also sealed, thereby safety with respect to leak of the injection medium 46 is extreamly improved.

Since the seal between the hub stop rib 7d and the hub 9 is a position contact between the seal portions 7g, 7g and the opening ends 10h, 10h, the seal pressure is equally acted on each sealed portion, and therefore, its credibility is high.

On the other hand, in the packing 37, as described before, the circular cylindrical portion 39 and the fold 45 of the packing 37 are inserted into the main cylindrical portion 3 of the syringe body 2 reducing in the direction as shown by the arrow D by elastic deformation. That is, the circular cylindrical portion 39 of the packing 37 and the fold 45 press the inner peripheral face 3c of the main cylindrical portion 3 with a force in the direction as shown by the arrow C, and the portion between the packing 37 and the main cylindrical portion 3 is sealed with water seal (air seal). That is, the injection medium 46 of the medium holding space 47 does not leak in the inside space 2a of the arrow B side of the packing 37 and the like, passing between the packing 37 and the main cylindrical portion 3.

In addition, since the circular cylindrical portion 39 of the packing 37 and the fold 45 are reduced in the direction as shown by the arrow D by elastic deformation, the packing support 35 of the piston 29, which is inserted into the first hole 42 and the second hole 43 of the packing 37, is pressed by the packing 37 in the direction as shown by the arrow D. That is, the portion between the packing 37 and the packing support 35 is closely sealed. Therefore, the injection medium 46 of the medium holding space 47 can flow to the third hole 43 of the packing 37, but the injection medium 46 does not leak in the inside space 2a of the arrow B side of the packing 37 and the like, further passing between the packing 37 and the packing support 35 in the second hole 42 and the first hole 41.

After filling of the injection medium 46, the needle 26 of the syringe assembly 1 is stuck in a patient's arm with the main cylindrical portion 3 of the syringe assembly 1 supported with one hand.

Subsequently, the main cylindrical portion 3 of the syringe body 2 of the syringe assembly 1 is grasped with fingers of one hand, and the syringe support 5 is supported and fixed in the direction as shown by the arrow B from a plate face of the arrow A side of the syringe support 5 with the fingers which grasp the main cylindrical portion 3. The outer press plate 32 of the piston 29 is pressed in the direction as shown by the arrow A with other finger (the thumb) of the same hand as one of the fingers, by which the main cylindrical portion 3 is grasped so as to drive the piston 29 to the syringe body 2 in the direction as shown by the arrow A. By drive of the piston 29, the capacity of the medium holding space 47 reduces, thereby the injection medium 46 in the medium holding space 47 is pressurized. By pressure, pressure difference arises between the medium holding space 47 and the outside of the top end 26a side of the needle 26, that is, the body of a patient. Therefore, the injection medium 46 of the medium holding space 47 flows in the body in the injection part of a patient through the piston engagement hole 20 of the hub 9, the flow hole 19 and the medium flow hole 26c of the needle 26.

Figure 8:
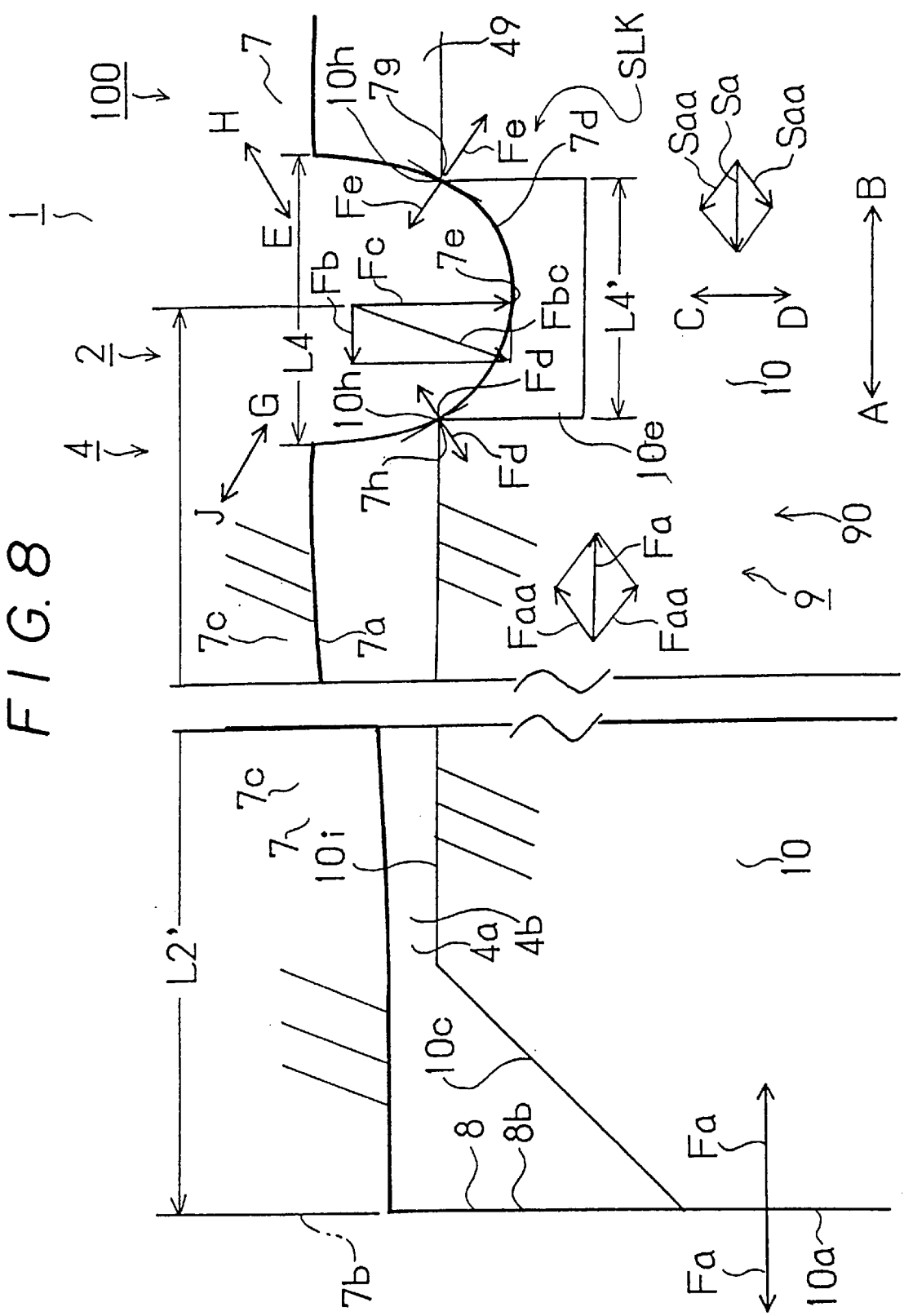
FIG. 8 is a view showing dynamical relation between the hub insertion portion and the hub as shown in FIG. 2.
Figure 9:
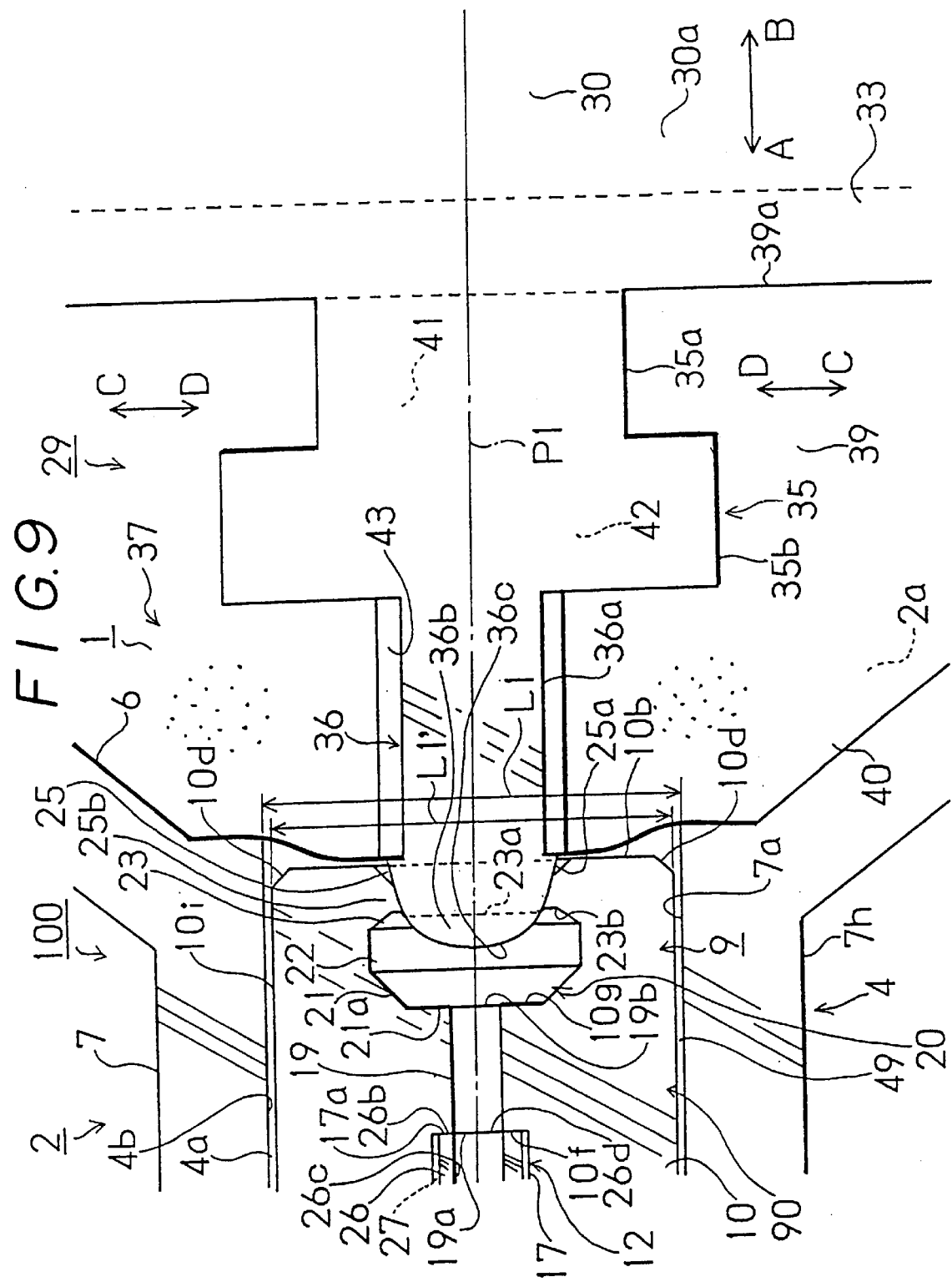
FIG. 9 is a view showing a routine of engaging the hub as shown in FIG. 2 with the piston.

As described before, the injection medium 46 in the medium holding space 47 is pressurized and an action force Sa by the pressure of the injection medium 46 is acted on the hub 9 in the direction as shown by the arrow A from the end face 10b side of the hub 9 adjacent to the injection medium 46, as shown in FIG. 8.

A predetermined restoring force Fbc is set so as not to respectively disengage the seal portions 7g, 7g at both sides of the arrows A and B from the opening ends 10h, 10h so that both seal pressure Fd and Fe, which respectively act between the seal portions 7g, 7g and the opening ends 10h, 10h at both sides of the arrows A and B, may not become to be zero or minus if the most action force Sa potential acts.

Therefore, the portion between the end wall 8 and end face 10a of the hub 9 and the portion between the seal portions 7g, 7g of both sides of the arrows A and B of the hub stop rib 7d and the opening ends 10h, 10h of both sides of the arrows A and B of the hub 9 are continuously sealed and water tight state (or air tight state) is maintained.

After the predetermined amount of the injection medium 46 is streamed in the body of a patient, that is, after the taper 40 of the packing 37 is inserted in the inside of the taper 6 of the syringe body 2 so as to adjust, and the piston 29 is driven until the insertion portion 36b of the hub engagement portion 36 of the piston 29 abuts on the third taper hole 25 of the piston engagement hole 20 of the hub 9, as shown in FIG. 5, the whole syringe assembly 1 is pulled in the direction as shown by the arrow B with respect to a patient through the hand or fingers supporting the syringe assembly 1 therewith so as to pull out the needle 26 from the injection part of a patient.

After pulling the needle 26, the piston 29 and the hub 9 are engaged with each other.

That is, the outer press plate 32 of the piston 29 is further pressed with a finger in the direction as shown by the arrow A.

Just after finish of the flow operation of the injection medium 46 into a body, the taper 40 of the packing 37 is inserted in the inside of the taper 6 of the syringe body 2 so as to adjust, the insertion portion 36b is inserted into the inside of the third taper hole 25 so as to adjust. Therefore, a force in the direction as shown by the arrow A acts on the packing 37 as the insertion portion 36b is advanced in the third taper hole 25 in the direction as shown by the arrow A by driving the piston 29. Since the packing 37 is supported by the taper 6 in the direction as shown by the arrow B, it can not move in the direction as shown by the arrow A. However, the packing 37 has flexibility, and the only insertion portion 36b moves in the direction as shown by the arrow A, and the packing 37 itself remains reducing in the directions as shown by the arrows A and B by elastic deformation.

Since a force in the direction as shown by the arrow A is added to the piston 29 by pressing pressure, a pressing force T in the direction as shown by the arrow A is added to the insertion portion 36b of the hub engagement portion 36, as shown in FIG. 5.

The pressing force T acts to the hub 9 from the insertion portion 36b at the portion, at which the insertion portion 36b and the wall face 25a abut on each other, as a component force Ta in the direction, in which the insertion portion 36b and the wall face 25a of hub 9 facing the third taper hole 25 abut on each other, that is, in the direction as shown by the arrow W in the figure perpendicular to the wall face 25a (that is, the direction away from the axis center P1 and in the direction near the direction as shown by the arrow A). In addition, a reaction Ta' of the component force Ta acts to the insertion portion 36*b* from the hub 9 at the portion, where the insertion portion 36*b* abuts on the wall face 25*a*, in the direction as shown by the arrow W', which is opposite of the direction as shown by the arrow W.

By the component Ta, the projection 25*b* of the hub 9 which abuts on the insertion portion 36*b* in the wall face 25*a*, is elastically deformed in the direction as shown by the arrow W enlarging the diameter of the projection 25*b* in an apex, that is, the diameter in the boundary portion 23*a*. In addition, by the reaction Ta', the insertion portion 36*b* is elastically deformed reducing the diameter of the section perpendicular to the axis center P1.

The piston 29 is further pressed in the direction as shown by the arrow A so as to further advance the insertion portion 36*b* in the third taper hole 25 in the direction as shown by the arrow A. That is, the insertion portion 36*b* passes the boundary portion 23*a* in the direction as shown by the arrow A, reducing the diameter of the insertion portion 36*b* and enlarging the diameter of the boundary portion 23*a* so as to correspond the diameter of the insertion portion 36*b* with one of the boundary portion 23*a*. After the whole insertion portion 36*b* completely passes the boundary portion 23*a*, the press of the piston 29 finishes.

The whole insertion portion 36*b* completely passes the boundary portion 23*a*, thereby the insertion portion 36*b* is inserted in the space formed by the first taper hole 21, the cylindrical hole 22 and the second taper hole 23 as shown by the two-dot chain line of FIG. 5 so as to adjust. The circular cylindrical portion 36*a* extending at the arrow B side of the insertion portion 36*b* exists penetrating the boundary portion 23*a* in the directions as shown by the arrows A and B. Then, the piston 29 and the hub 9 are engaged with each other.

The pressing force T in the direction as shown by the arrow A acts on the insertion portion 36*b*, thereby the pressing force T in the direction as shown by the arrow A acts on the hub 9 also (This is because the resultant force of the component force Ta of the pressing force T is the pressing force T.). However, the hub 9 is supported in the direction as shown by the arrow B with a hand supporting the syringe body 2 through the hub stop rib 7*d* of the hub insertion portion 4 or the wall face 8*b* of the end wall 8 formed meeting at right angles with respect to the axis center P1, and therefore, it receives reaction against the pressing force T in the direction as shown by the arrow B from the hub stop rib 7*d* or the end wall 8. That is, the hub 9 is not almost moved in the direction as shown by the arrow A and the like if the pressing force T is received, and the hub 9 is not pulled out of the hole 8*a* of the end wall 8 in the direction as shown by the arrow A.

After the piston 29 and the hub 9 are engaged with each other, the main cylindrical portion 3 of the syringe body 2 is supported with one hand, the outer press plate 32 is pulled to the syringe body 2 in the direction as shown by the arrow B with the other hand. By pulling the outer press plate 32, the action force Z in the direction as shown by the arrow B acts on the piston 29 and the insertion portion 36*b* of the hub engagement portion 36, as shown by the two-dot chain line in FIG. 5.

The action force Z acts to the hub 9 from the insertion portion 36*b* at the portion, at which the insertion portion 36*b* and the wall face 23*b* abut on each other, as a component force Za in the direction, in which the insertion portion 36*b* and the wall face 23*b* of hub 9 facing the second taper hole 23 abut on each other, that is, in the direction as shown by the arrow V in FIG. 5 perpendicular to the wall face 23*b* (that is, the direction away from the axis center P1 and in the direction near the direction as shown by the arrow B). In addition, the reaction Za' of the component force Za acts to the insertion portion 36*b* from the hub 9 at the portion, where the insertion portion 36*b* abuts on the wall face 23*b*, in the direction as shown by the arrow V', which is opposite of the direction as shown by the arrow V.

As described heretofore, the reaction Za' becomes to be a force reducing the insertion portion 36*b* in the direction as shown by the arrow V'. However, the reaction Za' is smaller than the force relatively reducing the insertion portion 36*b* till the insertion portion 36*b* passes the diameter of the boundary portion 23*a*.

In addition, the action force Z in the direction as shown by the arrow B acts on the insertion portion 36*b*, thereby the action force Z in the direction as shown by the arrow B acts on the hub 9 also (This is because the resultant force of the component force Za of the action force Z is the action force Z.). Even in case where the hub 9 is moved to the syringe body 2 in the direction as shown by the arrow A and then the hub 9 is disengaged from the hub stop rib 7*d* when the piston 29 is engaged with the hub 9, the hub 9 moves to the syringe body 2 in the direction as shown by the arrow B by the action force Z, thereby the hub 9 and the hub stop rib 7*d* are once returned to the position similar to the position where both are engaged with each other again. Dynamical relation between the hub insertion portion 4 and the hub 9 when the action force Z acts is not illustrated. However, the action force Z acts in the same direction as one of the differential pressure force Na. And, the action force Z acts in the same direction as one of the differential pressure force Na generating at the time of filling of the injection medium 46, but the action force Z is bigger than the most differential pressure force Na potential.

On this occasion, a predetermined restoring force Fbc is set so as to sufficiently emulate the most differential pressure force Na potential, but so as not to emulate the action force Z bigger than the most differential pressure force Na potential. That is, by the action force Z, the hub 9 presses and moves the hub stop rib 7*d* in the opening end 10*h* of the arrow A side in the direction as shown by the arrow C. That is, the hub stop rib 7*d* of the small cylindrical portion 7 and the portion near the hub stop rib 7*d* further expand and deform in the direction as shown by the arrow C. The seal between the hub stop rib 7*d* and the hub 9 (especially, at the arrow B side) is of course disengaged since the hub stop rib 7*d* moves in the direction as shown by the arrow C.

In this way, the hub stop rib 7*d* of the small cylindrical portion 7 and the portion near the hub stop rib 7*d* are further expanded in the direction as shown by the arrow C further adding the action force Z. On the other hand, the inside diameter in the hub stop rib 7*d* of the small cylindrical portion 7 broadens by expansion, the hub 9 receiving the force pulling in the direction as shown by the arrow B advances in the direction as shown by the arrow B as the inside diameter broadens. Continuously further adding the action force Z, the hub 9 is advanced to the position where the top end 7*e* of the hub stop rib 7*d* abuts on the opening end 10*h* of the arrow A side, that is, the hub 9 in the outer peripheral face 10*i* of the main pillar portion 10.

After the hub 9 is advanced to the position where the hub stop rib 7*d* abuts on the outer peripheral face 10*i* of the main pillar portion 10, the piston 29 is pulled with the force emulating frictional force in the direction as shown by the arrow A generating at the position where the hub stop rib 7d abuts on the outer peripheral face 10i so as to further advance the hub 9 in the direction as shown by the arrow B, and the hub 9 is pulled until it is completely pulled out of the small cylindrical portion 7 in the direction as shown by the arrow B.

On this occasion, since the outside diameter L1' of the main pillar portion 10 of the hub 9 is smaller than the inside diameter L1 of the hub insertion hole 4b, the contact between the hub 9 and the small cylindrical portion 7 is executed only through the hub stop rib 7d portion, and its pulling operation can be easily executed with a small force after the hub stop rib 7d is disengaged from the hub stop groove 10e.

The piston 29 is further pulled and the needle 26, which is inserted and fixed at the arrow A side of the hub 9, inserts into the hub insertion space 4a from the hole 8a of the end wall 8 in the direction as shown by the arrow B, and further inserts in the inside space 2a of the main cylindrical portion 3 in the direction as shown by the arrow B, and the piston 29 is pulled in the direction as shown by the arrow B such that the top end 26a of the needle 26 is completely inserted into the inside space 2a.

Figure 10:
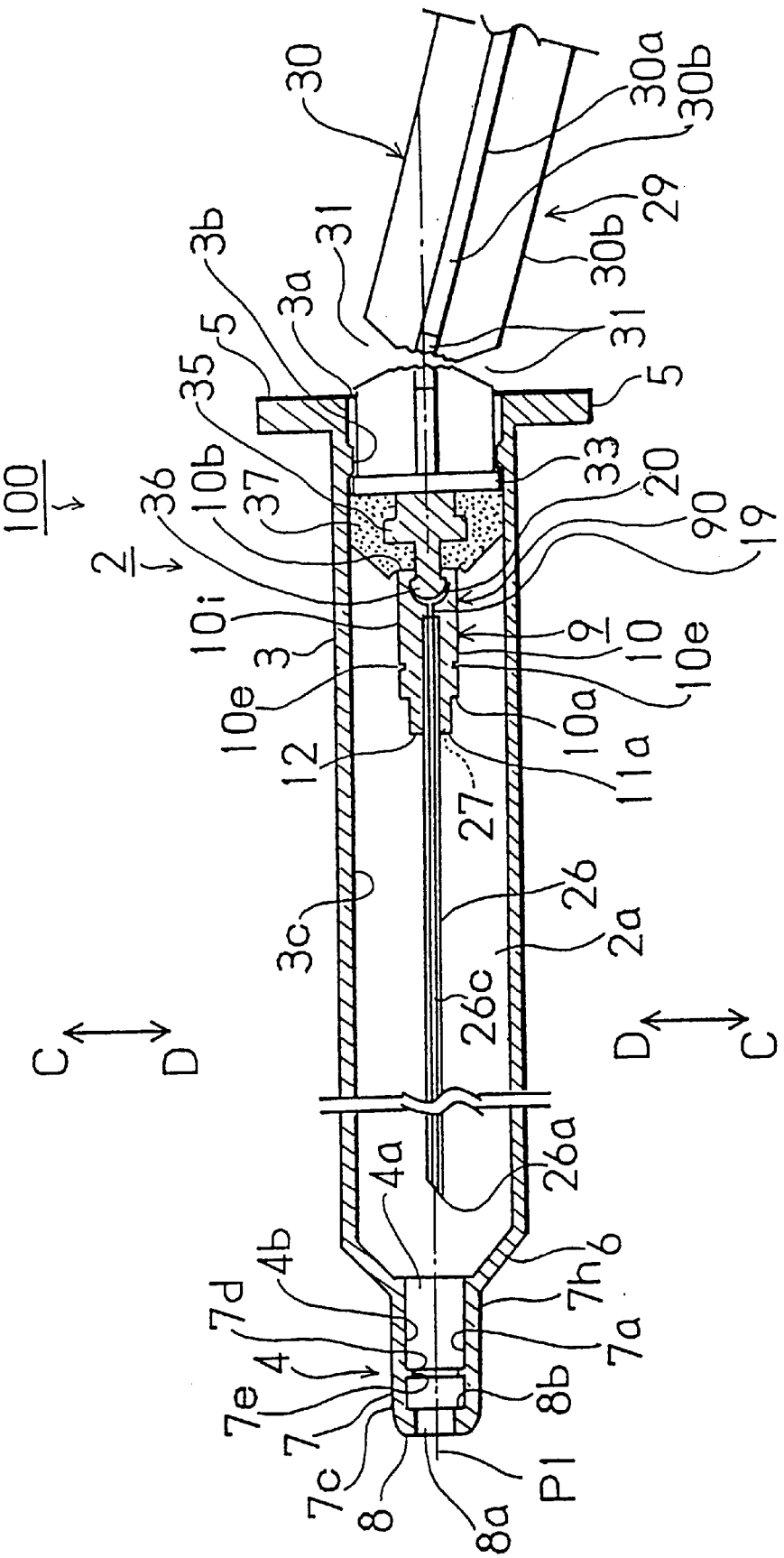
FIG. 10 is a view showing bending and taking of the piston in the syringe assembly as shown in FIG. 1.

The piston 29 is further pulled till the inner press plate 33 abuts on the engagement rib 3b of the main cylindrical portion 3 of the syringe body 2, as shown in FIG. 10, and the piston 29 is stopped.

On this occasion, the inner press plate 33 of the piston 29 is engaged with and stopped by the engagement rib 3b so as to prevent the needle 26 inserted into the hub 9 engaged with the piston 29 from springing to the outside the syringe body 2, by excessively pulling the piston 29 by mistake. In addition, the accident of secondary infection and the like generating from the hurt of hands and the like by the needle 26 can be prevented.

And, in such a state that the inner press plate 33 of the piston 29 is engaged with and stopped by the engagement rib 3b, the position of the notch 31 formed on the piston body 30 of the piston 29 is adjusted to the position of the opening end 3a of the syringe body 2 in the directions as shown by the arrows A and B, as shown in FIG. 10.

Subsequently, while the syringe body 2 is fixed with one hand, the piston 29 is grasped with the other hand, and as shown in FIG. 10, a force in the direction as shown by the arrow C is added to the piston 29. By adding a force in the direction as shown by the arrow C to the piston 29 with respect to the syringe body 2, bending stress is added to the piston body 30 with the engagement rib 3b and the opening end 3a of the syringe body 2 as a supporting point, and then the piston body 30 is broken in the notch 31, which structure is relatively weak with respect to bending stress, of the piston body 30 and the piston body 30 is separated into the arrow A side portion and the arrow B side portion forming a boundary with the notch 31.

By making the engagement rib 3b and the opening end 3a of the syringe body 2 a supporting point, bending stress can be effectively added to the piston body 30 using a principle of a lever. In addition, since the position of the notch 31 is at the position of the opening end 3a, that is, the position of the supporting point, the bending stress adding to the piston body 30 is effectively added to the portion of the notch 31. Therefore, the piston body 30 can be easily bent so as to separete, that is, easily folded and taken.

Subsequently, the portion of the syringe body 2 side folded and taken and the portion of the outer press plate 32 of the piston 29 are disposed of so as to be discarded.

Since the needle 26 is completely inserted and stored in the inside space 2a of the syringe body 2 being held with the top end portion of the piston 29 remaining in the inside space 2a, there is no fear of hurting hands or the like and being secondarily infected from wound by the needle 26. Therefore, waste disposal can be safely executed. And, the piston 29 is folded and taken, thereby the syringe assembly 1 folded and taken is not bulky, and then waste disposal can be smoothly executed. As described before, the use of the syringe assembly 1 and waste disposal after use all finish.

As described heretofore, the hub 9 of the syringe assembly 1 is inserted into the hub insertion hole 4b, and has a cylindrical hub body 90 through which the hub 9 is pulled from the hub insertion hole 4b to the inside space 2a of the syringe body 2. At the outer periphery portion of the hub body 90, the hub stop groove 10e is annularly formed so as to engage with the inner face of the hub insertion hole 4b. The outside diameter L1' of the portions excluding the hub stop groove 10e of the hub body 90 is smaller than the inside diameter L1 of the portion corresponding to the hub insertion hole 4b. The needle insertion hole 12 in which the needle 26 can be inserted is provided with the end portion 11a of the hub body 90 in the direction of the axis center P1 of the hub body 90. The flow hole 19 is provided with the hub body 90 communicating the needle insertion hole 12 and the inside space 2a of the syringe body 2 with each other in the direction of the axis center P1. At the end portion of the hub body 90, the piston engagement hole 20 is provided capable of engaging with the piston 29.

The connecting structure between the hub 9 and the syringe body 2 is that the hub body 90 of the hub 9 is inserted into the hub insertion hole 4b, and is attachably and detachably inserted so as to be able to be pulled out of the hub insertion hole 4b to the inside space 2a of the syringe body 2. At the inner peripheral face 7a of the hub insertion hole 4b, the hub stop rib 7d is annularly provided, and the hub stop groove 10e of the hub body 90 is provided contacting and engaging with the hub stop rib 7d with a predetermined restoring force Fbc. The gap space 49 is provided between the inner periperal face 7a of the hub insertion hole 4b excluding the hub stop rib 7d and the outer peripheral face 10i of the hub body 90. The gap allows the hub 9 to be extremely easily pulled to the inside space 2a.

In addition, the connecting structure between the hub 9 and the syringe body 2 is comprised such that the width L4' of the hub stop groove 10e is different from the width L4 of the hub stop rib 7d.

And, the syringe assembly 1 has the syringe body 2 and the hub 9 comprising the connecting structure, the piston 29 is movably provided in the main cylindrical portion 3 of the syringe body 2 in the direction of the axis center P1 with respect to the main cylindrical portion 3 occupying the inside space 2a of the main cylindrical portion 3 in the direction of the axis center P1, the hub engagement portion 36 is provided with the piston 29 so as to engage with the piston engagement hole 20 of the hub 9 facing the piston engagement hole 20. The needle 26 is provided with the needle insertion hole 12 of the hub 9.

In addition, the piston 29 of the syringe assembly 1 is comprised in such a manner that the piston body 30 can be bent and taken between the outer press plate 32 and the inner press plate 33.

In addition, the engagement rib 3b is provided with the main cylindrical portion 3 of the syringe assembly 1 so as not to pull the inner press plate 33 of the piston 29 out of the main cylindrical portion 3.

The notch 31 is formed at the piston body 30 of the piston 29 of the syringe assembly 1.

In addition, the notch 31 is formed so as to position at the opening end 3a of the main cylindrical portion 3 when the piston 29 abuts on the engagement rib 3b.

Furthermore, when the syringe assembly 1 is assembled, the hub 9 is disposed elastically engaging the hub stop groove 10e of the hub 9 with the hub stop rib 7d of the hub insertion portion 4, the piston 29 is inserted into the syringe body 2, and the needle 26 is inserted into and contacted with the needle insertion hole 12 of the hub 9. The hub 9 and the needle 26 can be of course together inserted into and attached to the hub insertion portion 4 in such a state that the needle 26 is attached to the hub 9 in advance.

After use of the syringe assembly 1, the hub 9 and the piston 29 are engaged with each other by the operation of the piston 29 in the direction of the axis center P1 in the piston engagement hole 20 and the hub engagement portion 36, and furthermore, the hub 9 and the needle 26 attached to the hub 9 are inserted into the inside space 2a of the syringe body 2 by the operation of the piston 29 in the direction of the axis center P1.

After the hub 9 and the needle 26 attached to the hub 9 are inserted into the inside space 2a of the syringe body 2, the piston 29 is supported with the syringe body 2 in the engagement rib 3b and the opening end 3a when the piston 29 is folded so as to be taken, and therefore, a principle of a lever can be applied.

Furthermore, in case of assembly of the syringe assembly 1, the hub 9 of the syringe assembly 1 is pressed in the direction of the axis center P1 so as to insert into and attach to the hub insertion hole 4b.

Accordingly, in the hub 9, the connecting structure of the hub 9 and the syringe assembly 1 using the hub 9, by setting a predetermined restoring force Fbc as a desired size, the state of inserting the hub 9 into the hub insertion hole 4b can be maintained while the syringe assembly 1 is used, and the insertion state is by two sealing points such that the hub stop groove 10e and the hub stop rib 7d are contacted in two points. That is, water tight or air tight between the hub 9 and the syringe body 2 is extremely increased while the syringe assembly 1 is used.

The syringe assembly 1 may be comprised in such a manner that a plurality of slits 50 are formed in the hub insertion portion 4 of the syringe assembly 1.

Figure 11:
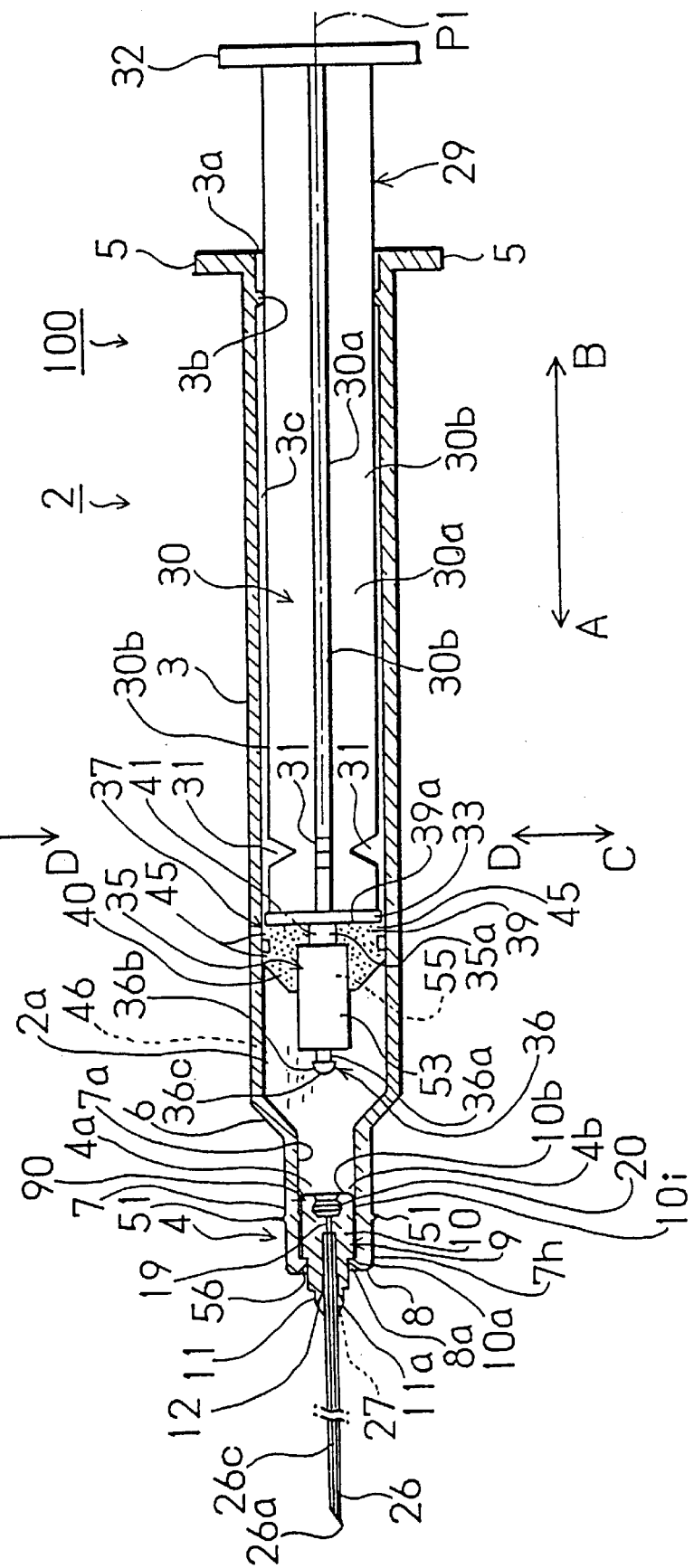
FIG. 11 is a typical sectional view showing an example of the syringe assembly having slits in the syringe of the syringe assembly according to the present invention.

That is, the syringe assembly 1 in which the slits 50 are formed, has the syringe 100 comprising the syringe body 2 and the syringe support 5, and in the syringe body 2, the main cylindrical portion 3, in which the engagement rib 3b is provided at the inner peripheral face 3c side, taper 6 and the hub insertion portion 4 are unitedly provided, similar to the syringe assembly 1 in which no slit 50 is provided in the first embodiment above mentioned, as shown in FIG. 11.

In the syringe assembly 1 in which the slits 50 are provided, the hub insertion portion 4 is comprised as follows.

Figure 13:
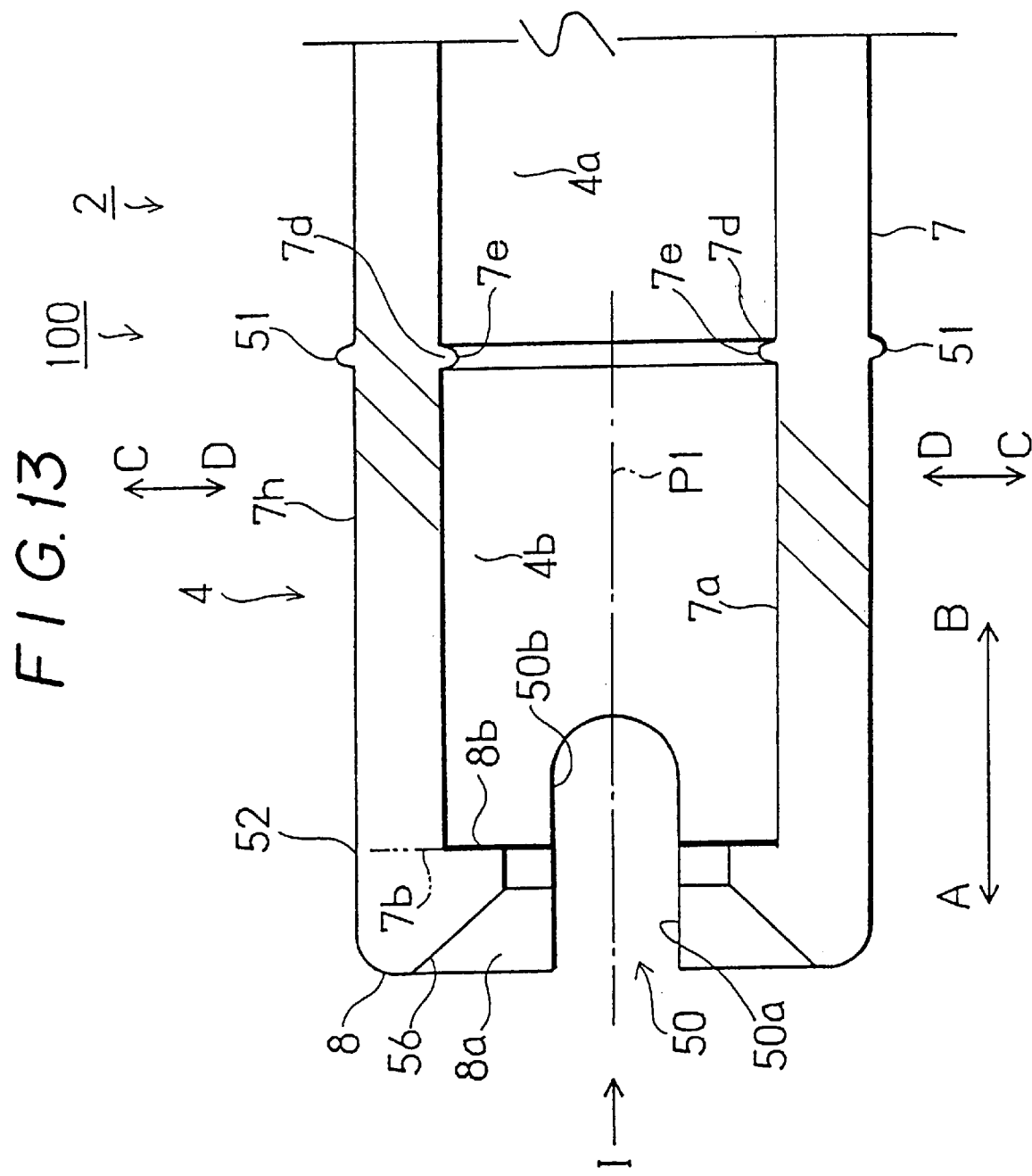
FIG. 13 is a view showing the portion near the hub insertion portion as shown in FIG. 11 in a natural state.
Figure 16:
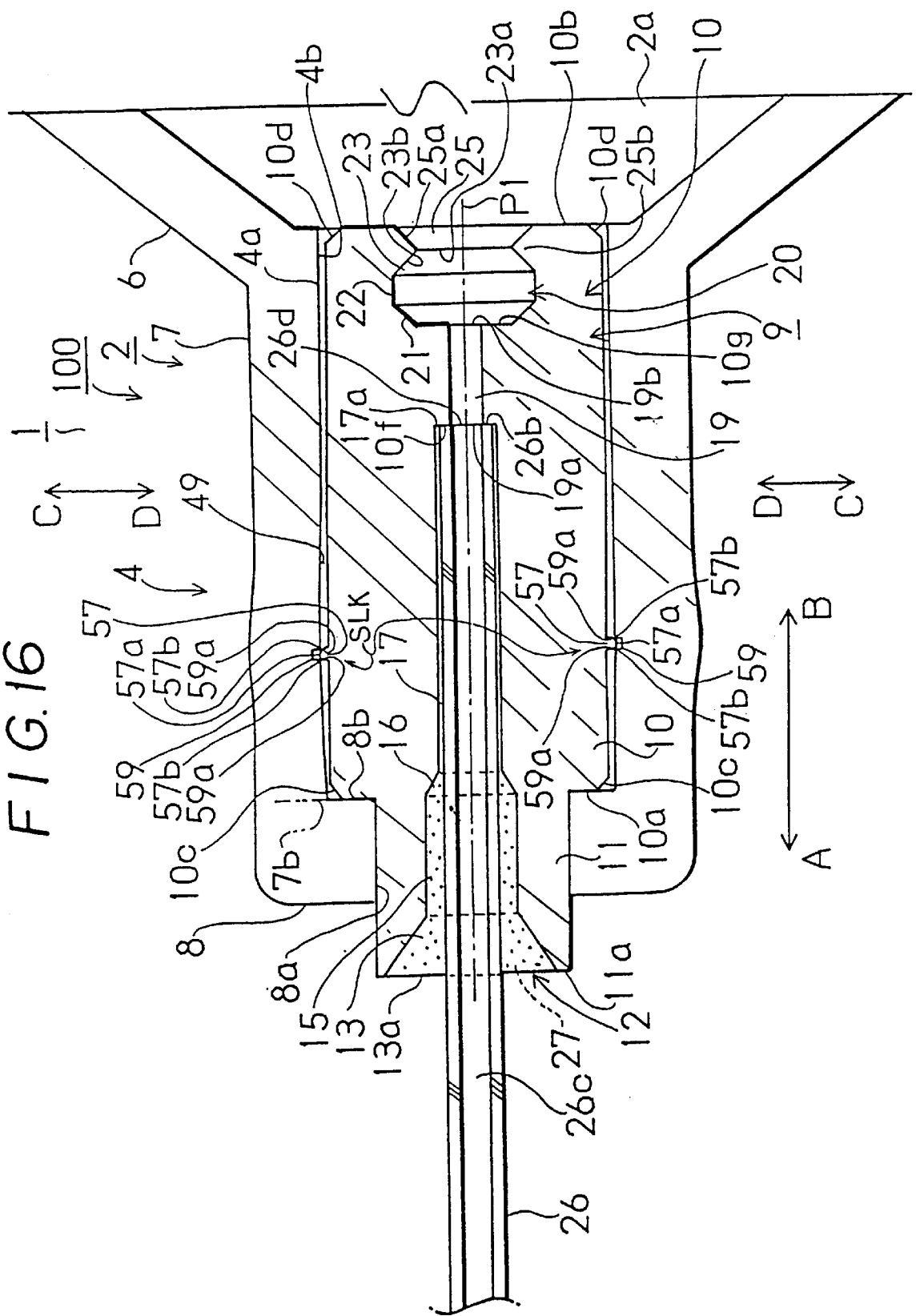
FIG. 16 is an enlarged sectional view of the portion near the hub in an example of the syringe assembly in which a seal rib is formed at the hub side and a seal groove is formed at a hub insertion hole side, of the syringe assembly according to the present invention.

That is, the hub insertion portion 4 has the small cylindrical portion 7 which is provided being united with the taper 6 and the end wall 8 which is provided being united with the small cylindrical portion 7 at the end portion 7b side of the small cylindrical portion 7, as shown in FIG. 13 or 16. The inside of the small cylindrical portion 7 is the hub insertion hole 4b. The hub stop rib 7d comprising a sealing structure SKL is annularly provided at the inner peripheral face 7a side of the small cylindrical portion 7, that is, at the inner peripheral face 7a side of the hub insertion hole 4b, and the section of the hub stop rib 7d is formed in the shape of a circular arc. A stiffening rib 51 is annularly provided at the outer peripheral face 7h side of the small cylindrical portion 7 at the position corresponding to the hub stop rib 7d putting the small cylindrical portion 7 therebetween (No stiffening rib 51 may be formed.)

The hole 8a is provided with the end wall 8 penetrating the end wall 8 in the directions as shown by the arrows A and B, and the hole 8a is taperingly formed in such a manner that its inside diameter is made bigger for the direction as shown by the arrow A.

Figure 14:
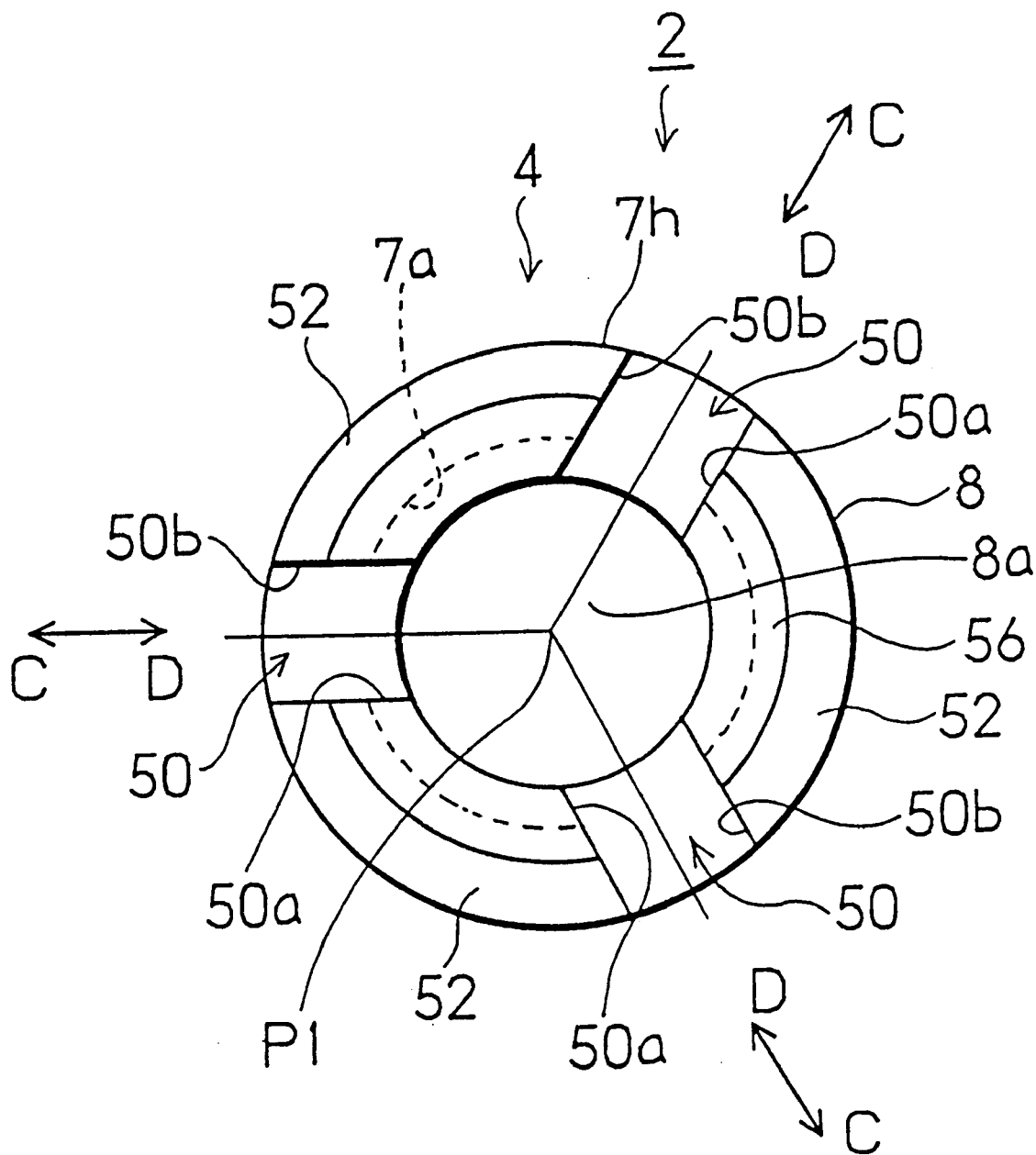
FIG. 14 is a view in the direction of the arrow I of FIG. 13.

Three first slits 50a are formed at the end wall 8 extending in a radial direction with respect to the axis center P1, that is, in the directions as shown by the arrows C and D in FIG. 14. These three first slits 50a are formed at 120 degrees pitch being equivalent to each other with the axis center P1 as its center. The three first slits 50a respectively communicate with the hole 8a focusing toward the hole 8a provided with the end wall 8.

On the other hand, three second slits 50b are formed at the small cylindrical portion 7 paralel to the directions as shown by the arrows A and B. The second slits 50b are formed at the arrow A side rather than the hub stop rib 7d and the stiffening rib 51 such that they don't reach the hub stop rib 7d and the stiffening rib 51. In addition, the three second slits 50b are formed corresponding to the three first slits 50a. The three second slits 50b and the three first slits 50a are united at the boundary portion between the small cylindrical portion 7 and the end wall 8 such that the corresponding two are communicated with each other and contacted with each other. The first slit 50a and the second slit 50b which are communicated and contacted with each other are the slit 50, and the hub insertion portion 4, in which three slits 50 are formed, is divided into three hub insertion portion pieces 52 at the arrow A side of the end wall 8 and the small cylindrical portion 7.

Figure 12:
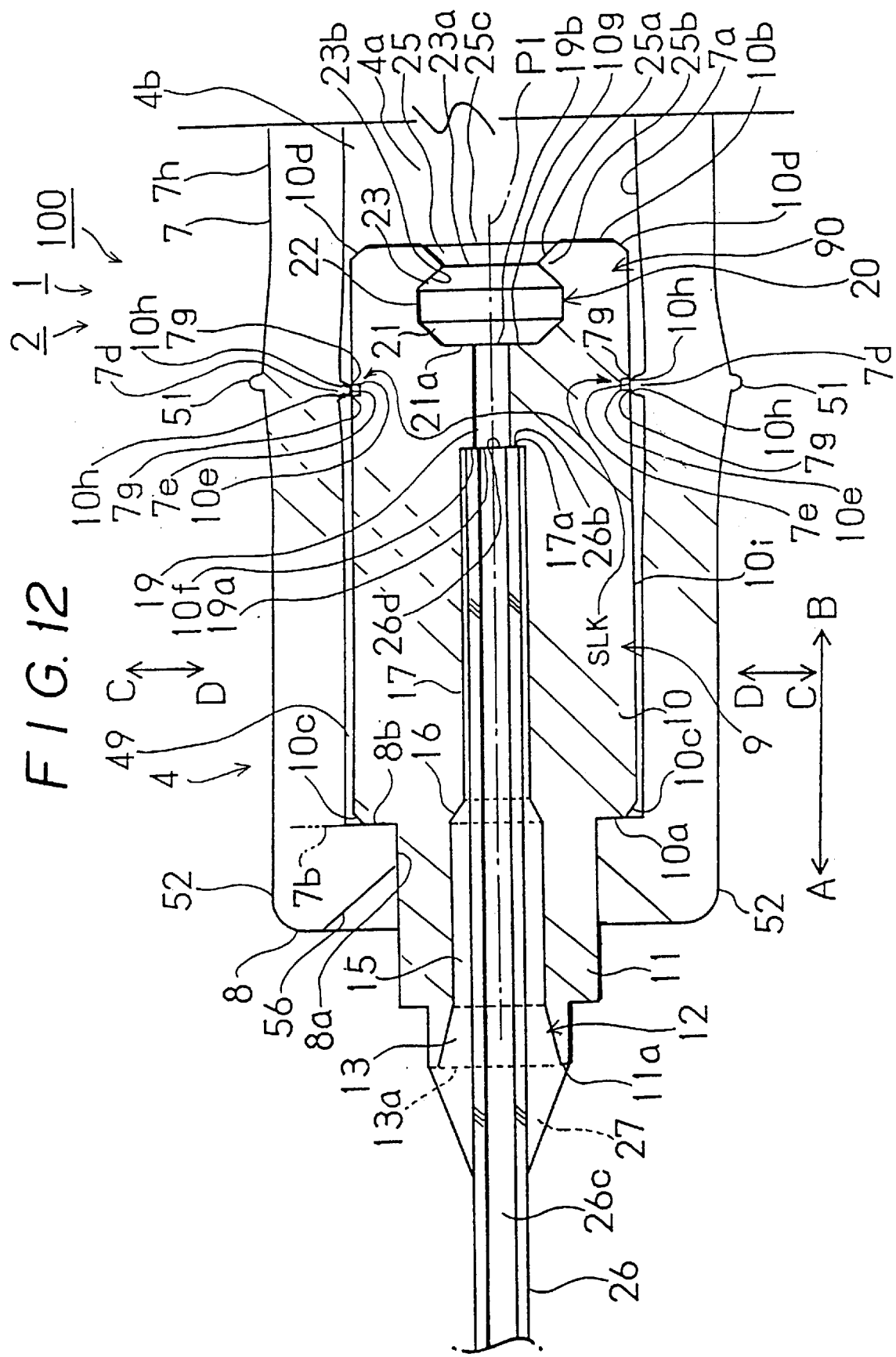
FIG. 12 is an enlarged sectional view in the portion near the hub of the syringe assembly as shown in FIG. 11.

As shown in FIG. 12, the hub 9 of the syringe assembly 1, in which the slits 50 are provided, has a hub body 90. The main pillar portion 10, which outside diameter is smaller than the inside diameter of the small cylindrical portion 7, is provided with the hub body 90. The hub stop groove 10e comprising a sealing structure is annularly formed at the outer peripheral face 10i side of the main pillar portion 10. The width of the hub stop groove 10e in the directions as shown by the arrows A and B is narrower than one of the hub stop rib 7d in the directions as shown by the arrows A and B.

The small pillar portion 11 is provided at the arrow A side of the main pillar portion 10. The needle insertion hole 12, which is comprised of the first taper hole 13, the first cylindrical hole 15, the second taper hole 16 and the second cylindrical hole 17 in the direction as shown by the arrow B from the end face 11a of the arrow A side of the small pillar portion 11, is provided with the hub 9.

The flow hole 19 is provided with the hub 9 at the arrow B side of the needle insertion hole 12, communicating with the needle insertion hole 12 in the directions as shown by the arrows A and B. At the arrow B side of the flow hole 19, the piston engagement hole 20 is provided communicating with the flow hole 19 in the directions as shown by the arrows A and B. The piston engagement hole 20 is comprised of the first taper hole 21, the cylindrical hole 22 and the second taper hole 23, and the piston engagement hole 20 is formed such that the flow hole 19 communicates with the inside of the hub insertion hole 4b, that is, the hub insertion space 4a in the directions as shown by the arrows A and B.

As shown in FIG. 12, in the hub insertion portion 4 of the syringe assembly 1, in which the slits 50 are provided, the small cylindrical portion 7 of the hub insertion portion 4 elastically expands in the hub stop rib 7d and the near portion thereof in the direction as shown by the arrow C, and the hub 9 is inserted into the hub insertion hole 4b of the hub insertion portion 4 elastically expanded. The hub 9 is inserted such that the main pillar portion 10 is inserted into the hub insertion hole 4b and the small pillar portion 11 is inserted into the hole 8a of the end wall 8. The end face 10a of the arrow A side of the main pillar portion 10 and the wall face 8b of the arrow B side of the end wall 8 closely contact with each other. The hub stop rib 7d of the small cylindrical portion 7 and the hub stop groove 10e of the main pillar portion 10 are at the positions which adjust and correspond to each other. Therefore, the hub stop rib 7d engages with the hub 9 in such a manner that the top end 7e of the hub stop rib 7d is inserted into the hub stop groove 10e in the direction as shown by the arrow D and the hub seal portions 7g, 7g of both sides of the top end 7e of the hub stop rib 7d and the opening ends 10h, 10h of both sides of the hub stop groove 10e respectively linearly abut on each other along the outer periphery of the hub 9.

On this occasion, the position of the end face 10b of the arrow B side of the hub 9 inserted into the hub insertion hole 4b is near the middle portion of the small cylindrical portion 7 in the directions as shown by the arrows A and B, as shown in FIG. 11.

Figure 15:
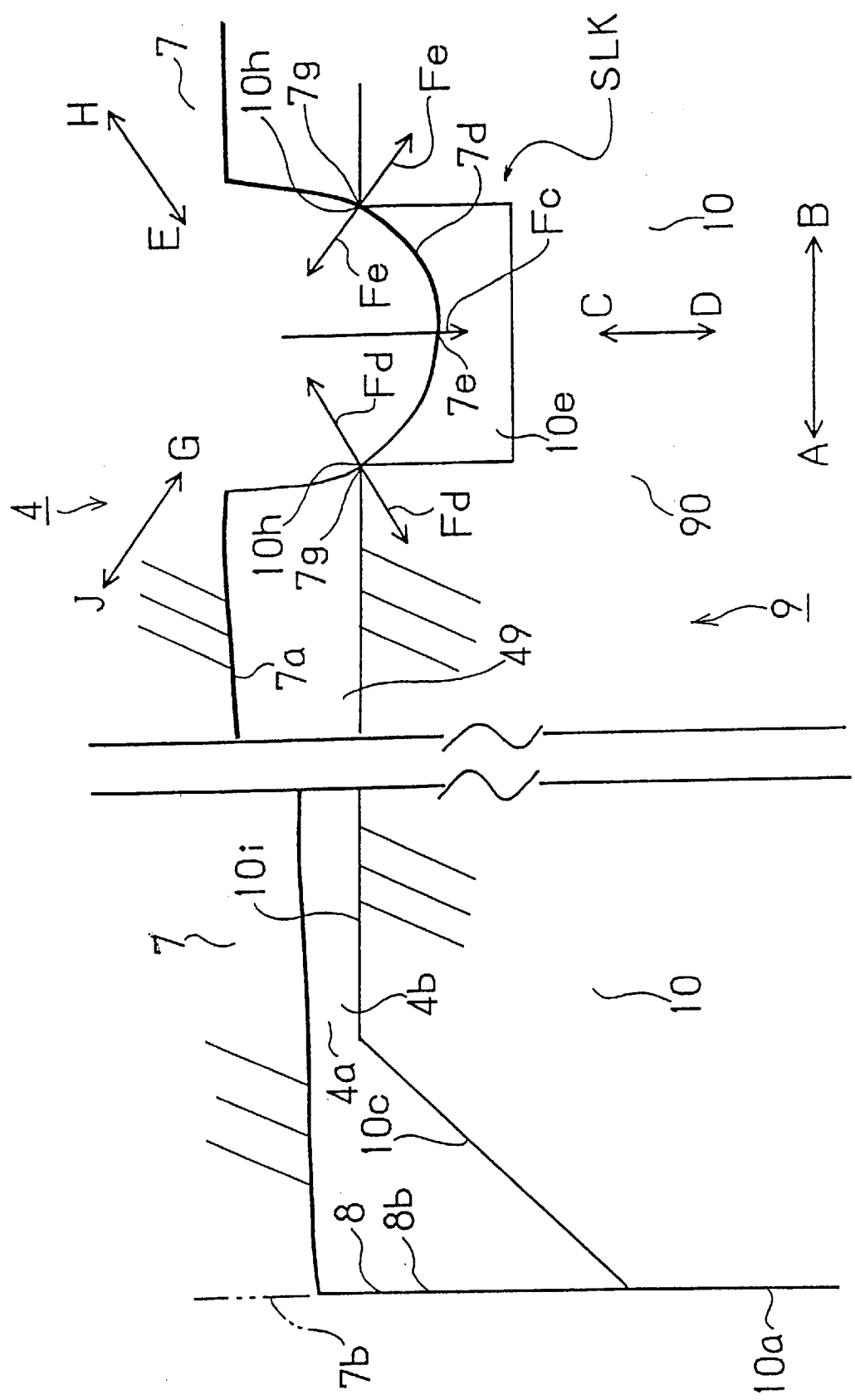
FIG. 15 is a view showing dynamical relation between the hub insertion portion and the hub as shown in FIG. 12.

Since the hub stop rib 7d and the near portion thereof are expanded in the direction as shown by the arrow C due to elastic deformation, a predetermined restoring force Fc in the direction as shown by the arrow D is added on the hub stop rib 7d, as shown in FIG. 15 (Since the small cylindrical portion 7 doesn't deform in the directions as shown by the arrows A and B, the restoring forces Fa, Fb and the like, which were explained in the first embodiment, are not applied between the end wall 8 and the hub 9 or between the hub stop rib 7d and the hub 9.).

That is, by the restoring force Fc, the portions which the hub 9 abuts on the hub stop rib 7d at the arrows A and B sides (that is, respective opening ends 10h, 10h and the respective seal portions 7g, 7g at the arrows A and B sides) balance in the abutting portions such that the seal pressures Fd, Fd and the seal pressures Fe, Fe are respectively added, that is, such that the abutting portions are sealed.

Then, the portion between the respective seal portions 7g, 7g of the arrows A and B sides of the hub stop rib 7d and the respective opening ends 10h, 10h of the arrows A and B sides of the hub 9 is sealed in the section of FIG. 15 with point contact, and the portion is in high water tight state (or air tight state) similar to FIG. 4.

On this occasion, the restoring force Fc can be preset as a desired size one according to the material of the hub insertion portion 4, the wall thickness of the small cylindrical portion 7 and the positions of the hub stop rib 7d and the hub stop groove 10e.

The rigidity of the hub stop rib 7d and the near portion thereof is increased in the small cylindrical portion 7 by the stiffening rib 51 which is at the position corresponding to the hub stop rib 7d putting the small cylindrical portion 7 therebetween, and therefore, a predetermined restoring force Fc can be effectively obtained.

On the other hand, in the hub 9 of the syringe assembly 1, in which the slits 50 are provided, as shown in FIG. 11 or 12, the needle 26 is inserted into the needle insertion hole 12, and the adhesive 27 is filled between the hub 9 and the needle 26 in the needle insertion hole 12 such that both are firmly bonded to each other.

As shown in FIG. 11, the piston 29 of the syringe assembly 1, in which the slits 50 are provided, has the bar-shaped piston body 30 extending in the directions as shown by the arrows A and B formed crossing the plate portions 30a and 30a. The four notches 31 are formed at the plate portions 30a, 30a of the piston body 30 from the respective both sides portions. The outer press plate 32 is provided with the piston body 30 at the arrow B side, and the inner press plate 33 is provided at the arrow A side. At the arrow A side of the inner press plate 33, the packing support 35 is provided. The circular cylindrical portion 35a, which is provided being united with the inner press plate 33, is provided with the packing support 35. At the arrow A side of the circular cylindrical portion 35a, an insertion cylindrical portion 53, which outside diameter is equal to one of the hub insertion hole 4b, is provided. At the arrow A side of the insertion cylindrical portion 53, the hub engagement portion 36 is provided. The circular cylindrical portion 36a, which is provided united with the insertion cylindrical portion 53, is provided with the hub engagement portion 36. At the arrow A side of the circular cylindrical portion 36a, the insertion portion 36b in a semi-spherical shape is provided.

The packing 37 is provided with the piston 29, and the packing 37 has the circular cylindrical portion 39 at which outer periphery portion the folds 45 are formed, and at the top end side of the circular cylindrical portion 39 (the arrow A side), the taper 40 is formed. The first hole 41, which inside diameter is equal to the outside diameter of the circular cylindrical portion 35a of the packing support 35, is provided with the packing 37 for the taper 40 from the end face 39a of the circular cylindrical portion 39 side. A second hole 55, which inside diameter is equal to the outside diameter of the insertion cylindrical portion 53 of the packing support 35, is provided with the packing 37 communicating with the first hole 41 at the arrow A side. The second hole 55 is open at the taper 40 side. The length of the first hole 41 in the directions as shown by the arrows A and B is equal to one of the circular cylindrical portion 35a in the directions as shown by the arrows A and B, and the length of the second hole 55 in the directions as shown by the arrows A and B is shorter than one of the insertion cylindrical portion 53 in the directions as shown by the arrows A and B.

The packing 37, which is comprised as described heretofore, is attached to the packing support 35 such that the circular cylindrical portion 35a of the packing support 35 is inserted into the first hole 41 and the insertion cylindrical portion 53 of the packing support 35 is inserted into the second hole 55.

The piston 29 attached the packing 37 thereto is inserted into the main cylindrical portion 3 of the syringe body 2 facing the packing 37 to the arrow A side. And, the folds 45 of the packing 37 and the circular cylindrical portion 39 are inserted into the main cylindrical portion 3 in such a manner that they are elastically reduced in the direction as shown by the arrow D. The inner peripheral face 3c of the main cylindrical portion 3 is smooth, and then the piston 29 is slidably inserted into the syringe body 2.

The syringe assembly 1, in which the slits 50 are provied, is comprised as described heretofore, and then, the assembly of the syringe assembly 1 is executed as follows.

At first, the first hole 41 of the packing 37 is broadened making use of flexibility of the packing 37, and after that, the hub engagement portion 36 side of the piston 29 is inserted from the first hole 41 side of the packing 37 for the direction as shown by the arrow A till the circular cylindrical portion 35a of the packing support 35 is inserted into the first hole 41 and the insertion cylindrical portion 53 of the packing support 35 is inserted into the second hole 55, as shown in FIG. 11 (The insertion cylindrical portion 53 is inserted into the second hole 55 in only a part of the arrow B side.).

Thereafter, the insertion of the packing 37 finishes after a hand or the like with which the first hole 41 is broadened is left therefrom so as to return the packing 37 to a natural state.

Subsequently, the piston 29 attaching the packing 37 thereto is inserted into the syringe body 2.

The insertion of the piston 29 is executed in such a manner that the side attached the packing 37 of the piston 29 is inserted into the inside space 2a of the syringe body 2 from the opening end 3a side of the syringe body 2 and the circular cylindrical portion 39 of the packing 37 and the outside diameter of the folds 45 are reduced by pressing the piston 29 in the direction as shown by the arrow A.

That is, the piston 29 is inserted into the main cylindrical portion 3 while the packing 37 is reduced and deformed by pressing the piston 29 in the direction as shown by the arrow A, and the piston 29 is inserted to the position, where the taper 40 of the packing 37 is inserted into the inside of the taper 6 of the syringe body 2 so as to adjust to each other, and then the insertion of the piston 29 finishes.

In such a state that the taper 40 of the packing 37 is inserted into the inside of the taper 6 of the syringe body 2 so as to adjust to each other, the insertion cylindrical portion 53 of the packing support 35 of the piston 29 is inserted in the hub insertion hole 4b of the hub insertion portion 4.

Subsequently, the hub 9 is inserted into the hub insertion hole 4b from the hole 8a side of the end wall 8 of the hub insertion portion 4.

That is, the end face 10b of the arrow B side of the hub 9 is adjusted to the hole 8a of the end wall 8, and in the afore-mentioned state, the hub 9 is pressed in the direction as shown by the arrow B. At the end wall 8 side of the hub insertion portion 4, the three slits 50 are provided as described heretofore, and the end wall 8 side of the hub insertion portion 4 is divided into the three hub insertion portion pieces 52. In addition, by pressing, the chamfer portion 10d of the hub 9 abuts on a tapered wall face 56 facing the hole 8a of the end wall 8, and then the action force for elastically bending and deforming the hub insertion portion pieces 52 in the direction as shown by the arrow C is applied to the three hub insertion portion pieces 52. The hub insertion portion piece 52 is easy to be elastically bent and deformed in the direction as shown by the arrow C against the action force in the direction as shown by the arrow C for its construction in comparison with the cylindrical portions and the like not divided of the small cylindrical portion 7. Therefore, as the hub 9 is pressed, the hub insertion portion piece 52 is elastically bent and deformed in the direction as shown by the arrow C and the diameter of the hole 8a is broadened.

The hub 9 is further pressed so as to be elastically bend and deformed the hub insertion portion piece 52 and the diameter of the hole 8a is broadened to the outside diameter of the main pillar portion 10 of the hub 9 so as to insert the hub 9 into the hub insertion hole 4b from the main pillar portion 10. The hub 9 is further pressed so as to completely insert the main pillar portion 10 into the hub insertion hole 4b, and the insertion of the hub 9 by pressing is stopped at the position where the end face 10a of the main pillar portion 10 of the hub 9 is closely contacted with the wall face 8b of the arrow B side of the end wall 8.

At the position where the end face 10a of the main pillar portion 10 is closely contacted with the wall face 10a of the end wall 8, the small pillar portion 11 is penetratingly inserted into the hole 8a, which smallest diameter is slightly bigger rather than the outside diameter of the small pillar portion 11.

On this occasion, the hub stop rib 7d of the hub insertion portion 4 and the hub stop groove 10e of the hub 9 are at the positions which correspond to and ajust to each other, as described heretofore, and engage with each other so as to abut on each other by the seal portions 7g, 7g of the hub stop rib 7d and the opening ends 10h, 10h of the hub stop groove 10e.

As described heretofore, the insertion of the hub 9 into the syringe body 2 finishes. On this occasion, the hub 9 is fixed by the hub insertion portion 4 balancing respective forces between the hub stop groove 10e of the hub 9 and the hub stop rib 7d of the small cylindrical portion 7, as described heretofore.

In addition, the hub 9 exists such that the spherical surface 36c side of the insertion portion 36b of the engagement portion 36 of the piston 29 contacts with the wall face 25a facing the third taper hole 25 of the piston engagement hole 20 provided with the hub 9.

The insertion operation of the hub 9 into the syringe body 2 can be executed only by pressing the hub 9, and therefore, it is easy with no complex assembly operation.

Subsequently, the needle 26 is inserted into the needle insertion hole 12 of the hub 9 so as to be bonded. That is, the needle 26 is inserted into the needle insertion hole 12 from the rear end 26b side of the needle 26 in the direction as shown by the arrow B, as shown in FIG. 12 till the rear end 26b abuts on the innermost wall face 10f of the hub 9 of the needle insertion hole 12. After insertion, the space between the hub 9 and the needle 26 in the needle insertion hole 12 is filled with the adhesive 27 so as to harden the adhesive 27, the insertion of the needle 26 to the hub 9 finishes.

The end of the insertion of the needle 26 means the end of assembly of the syringe assembly 1, in which the slits 50 are provided. The needle 26 is in advance attached to the hub 9, and in this state the hub 9 attached the needle 26 thereto may be attached to the syringe body 2.

As described heretofore, the assembly of the syringe assembly 1, in which the slits 50 are provided, is easy with no complex operation since the most operations (that is, all the operations excluding the operation of the inserting and fixing the needle 26) are executed by pressing.

Furthermore, since the hub 9 is inserted after the piston 29 is inserted into the syringe body 2, dust entry into the inside space 2a is extremely saved while the hub 9 is inserted.

The syringe assembly 1, in which the slits 50 are provided, is comprised as described heretofore, and is assembled as explained before. The method of disposal after using the syringe assembly 1 is almost similar to one of the syringe assembly 1 having no slits 50 in the first embodiment.

As described heretofore, the connecting structure between the hub 9 and the syringe body 2 in the syringe assembly 1 having the slits 50 is comprised in such a manner that the hub body 90 of the hub 9 can be inserted into the hub insertion hole 4b from the hole 8a side of the end wall 8.

In addition, the connecting structure between the hub 9 and the syringe body 2 is comprised in such a manner that three slits 50 are formed at the periphery of the hole 8*a* of the hub insertion portion 4.

In addition, in case of the assembly of the syringe assembly 1, the piston 29 is inserted into the syringe body 2, the hub 9 is inserted into the hub insertion hole 4*b* from the hole 8*a* side of the end wall 8, and then, the hub 9 is positioned such that the hub stop groove 10*e* of the hub 9 elastically engages with the hub stop rib 7*d* of the hub insertion portion 4 each other, and the needle 26 is inserted into and contacted with the needle insertion hole 12 of the hub 9 (or the hub 9 attached the needle 26 thereto is inserted into the hub insertion hole 4*b*).

Therefore, in case of assembly of the syringe assembly 1, the hub 9 of the syringe assembly 1 is inserted into the hub insertion hole 4*b* pressing and inserting from the hole 8*a* side for the direction of the axis center P1, and is inserted without passing the inside space 2*a* of the syringe body 2.

Therefore, the main cylindrical portion 3 of the syringe body 2 and the like do not extremely electrify static electricity and dust entry into the inside space 2*a* is extremely saved.

The hub 9 as explained in the above-mentioned first and second embodiments is comprised in such a manner that the sealing structure SLK of the hub 9 side is a groove, that is, the hub stop groove 10*e*.

However, the sealing structure SLK of the hub 9 side may be the projection annularly formed at the outer peripheral face 10*i* side of the hub body 90 of the hub 9. Therefore, the seal portion of the hub 9, which is formed in the shape of a projection may be allowable, as shown in FIG. 16.

That is, in the embodiment as shown in FIG. 16, the hub 9 to be inserted into the hub insertion hole 4*b*, in which an annular seal groove 59 comprising the sealing structure SLK is provided at the inner face of the hub insertion hole 4*b*, is comprised in such a manner that a seal rib 57 comprising the sealing structure SLK, which is annularly formed at the outer peripheral face 10*i* side of the main pillar portion 10 of the hub 9, and which has the width broader than one of the seal groove 59, is provided (The slits 50 may be provided in the hub insertion hole 4*b*.).

Therefore, the connecting structure of the hub 9 to the syringe body 2 is that the main pillar portion 10 of the hub 9 is inserted into the hub insertion hole 4*b*, and is attachably and detachably inserted so as to pull out the hub insertion hole 4*b* into the main cylindrical portion 3, and the seal rib 57 of the main pillar portion 10 contacts and engages with the seal groove 59 of the hub insertion hole 4*b* with a predetermined seal pressure maintaining the sealing state with a point contact in the section of FIG. 16 above-mentioned. In addition, the gap space 49 is formed between the inner peripheral face 7*a* of the hub insertion hole 4*b* excluding the seal groove 59 and the main pillar portion 10.

In the method of assembling the syringe assembly 1 which is comprised in such a manner that the hub body 90 is inserted into the hub insertion hole 4*b* from the hole 8*a* side of the end wall 8, of the above-mentioned embodiments, the piston 29 is inserted into the syringe body 2, the hub 9 is inserted into the syringe body 2, and the needle 26 is inserted into and contacted with the hub 9. However, in the method of assembling the piston 29 is inserted into the syringe body 2, and after that, the hub 9 inserted the needle 26 therein in advance may be inserted into the syringe body 2. In this case, the syringe body 2 and the hub 9 attached the needle 26 thereto can be independently stored till just before using, and in use, a doctor and the like can use as a syringe assembly by inserting the hub 9 into the syringe 2, and various kinds of needles can be selectedly used for one syringe. As a result, the syringe body 2 and the hub 9 can be used for various purposes.

Figure 17:
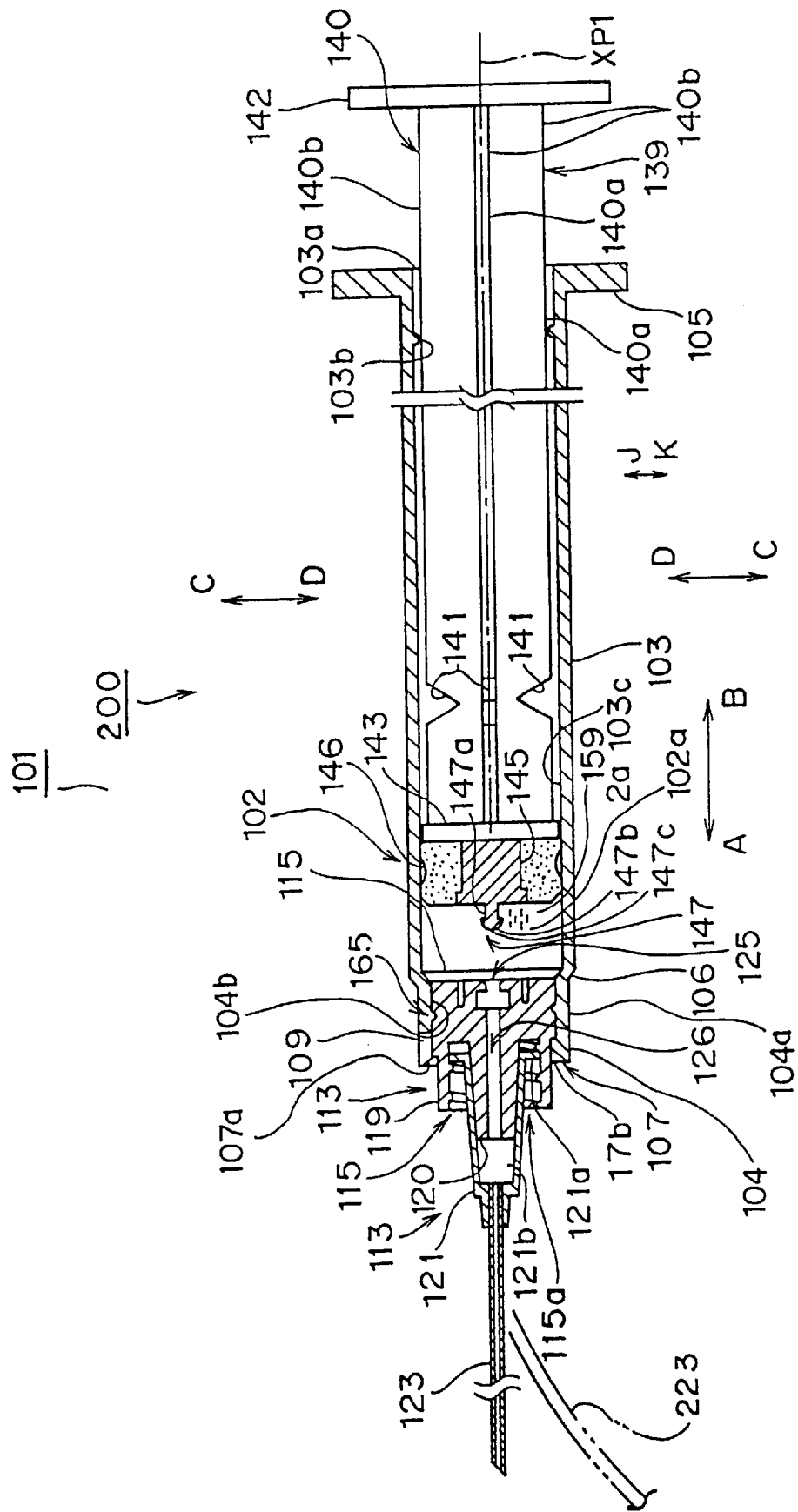
FIG. 17 is a typical sectional view showing an another example of the syringe assembly according to the present invention.

Subsequently, an another embodiment will now be explained. A syringe assembly 101, which is an another example of the syringe assembly according to the present invention, has a syringe 200 as shown in FIG. 17, and a syringe body 102 is provided with the syringe 200 (FIG. 17 is a typical cross section of the syringe assembly 101, but its side is shown in a part of a piston 139, described hereinafter, not the section, for convenience). A main cylindrical portion 103, cylindrically formed, is provided with the syringe body 102. A direction of an axis center of the main cylindrical portion 103, that is, the reciprocating directions parallel to an axis center XP1 are the arrow A direction in the figure (or the left direction of the paper of FIG. 17) and the arrow B direction (or the right direction of the paper of FIG. 17). Therefore, the directions as shown by the arrows A and B are the axis center direction of the syringe body 102.

At the outer periphery side of the main cylindrical portion 103, a syringe assembly supporting portion 105, being in the shape of a plate, is provided near an opening end 103*a* of the arrow B side of the main cylindrical portion 103 (the right side of the paper of FIG. 17), forming a flange of the main cylindrical portion 103. At an inner peripheral face 103*c* side of the main cylindrical portion 103, an engagement rib 103*b*, projecting in the direction for the axis center XP1 of the main cylindrical portion 103, that is, the direction as shown by an arrow D of the figure, is annularly formed near the opening end 103*a* along the inner peripheral face 103*c*.

Figure 18:
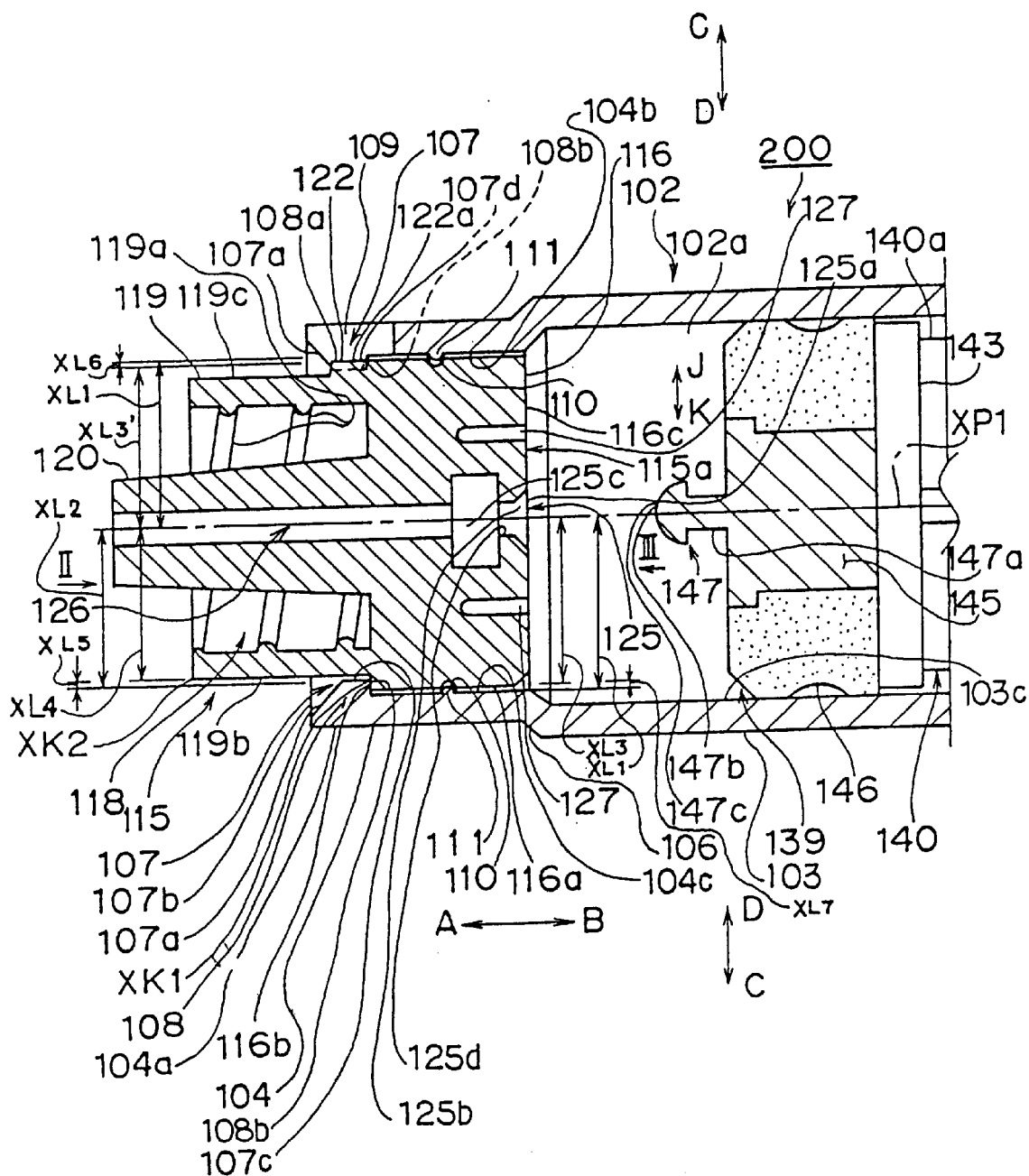
FIG. 18 is an enlarged sectional view near an installation hole of the syringe assembly as shown in FIG. 17.

At the arrow A side of the main cylindrical portion 103 (the left side of the paper of FIG. 17), as shown in FIGS. 17 and 18, a taper 106 in the shape of a funnel is formed unitedly connecting with the main cylindrical portion 103. The inside diameter in the section perpendicular to the directions as shown by the arrows A and B of the taper 106 (that is, the circular section) is made narrower for the direction as shown by the arrow A. The inside of the main cylindrical portion 103 and the inside of the taper 106 communicate with each other in the directions as shown by the arrows A and B, and the space combined both insides is an inside space 102*a* of the syringe body 102.

At the side of the arrow A of the taper 106, that is, at the side of the top of the syringe body 102, as shown in FIGS. 17, 18, 20 and 22, an installation portion 104 in the shape of a cylinder, which center is said axis center XP1 basically, is formed unitedly connecting with the taper 106, and extends in the direction as shown by the arrow A. Then, the installation portion 104 has an installation hole 104*b* in the shape of a cylinder in its inside. At the top end of the arrow A side of the installation hole 104*b*, an introducing hole 107*b*, which is open in the shape of almost circle, is provided, communicating the installation hole 104*b* and the outside of the syringe body 102 with each other in the directions as shown by the arrows A and B. Near the introducing hole 107*b* of the inner peripheral portion of the installation hole 104*b*, that is, at the position of the arrow B side of the introducing hole 107*b*, a stopper portion 107 is formed. That is, the stopper portion 107 is formed in the shape of a rib projecting from the inner peripheral portion of the installation hole 104*b* in the direction as shown by the arrow D of the figure, and is formed in the shape of a basically anular stripe along the plane perpendicular to the directions as shown by the arrows A and B, along the inner peripheral portion of the installation hole 104*b*. And, the stopper portion 107 is comprised of three projecting bodies 108 extending around a circular arc at a predetermined pitch XPT1 (for instance, 105 degrees in FIG. 20) with the axis center XP1 as its center, and between two projecting bodies 108 and 108, a chipped portion 108a, extending around a circular arc at a predetermined pitch XPT2 (for instance, 15 degrees in FIG. 20) with the axis center XP1 as its center, is formed. That is, three projecting bodies 108 are located in the directions as shown by the arrows E and F of the figure, the peripheral direction which center is the axis center XP1. The part between an apical portion 107c of the stopper portion 107 and the introducing hole 107b is taperingly formed in such a manner that the sectional area of the installation hole 104b gradually enlarges for the direction of the arrow A. Then, an open top end face 107a is taperingly formed between the apical portion 107c of these stopper portions 107 and the introducing hole 107b. The cross section of the apical portion 107c of the stopper portion 107, that is, the cross section of the apical portion 107c of each projecting body 108 is formed in the shape of an annular face almost parallel to the directions as shown by the arrows A and B as shown in FIG. 18.

As shown in FIGS. 17, 18, 20 or 22, three slits 109 are provided with the installation portion 104, dividing the arrow A side of the installation portion 104 into three installation portion pieces 104a with the axis center XP1 as its center. Each slit 109 is provided, forming the chipped portion in the installation portion 104 extending around the circular arc at the predetermined pitch XPT2 with the axis center XP1 as its center (the same pitch as the pitch XPT2 of the chipped portion 108a above-mentioned). In addition, each slit 109 is formed at the position corresponding to and matching with each chipped portion 108a of the stopper portion 107 above-mentioned, then each slit 109 is located between respective projecting bodies 108 and 108 of the stopper portion 107.

Figure 19:
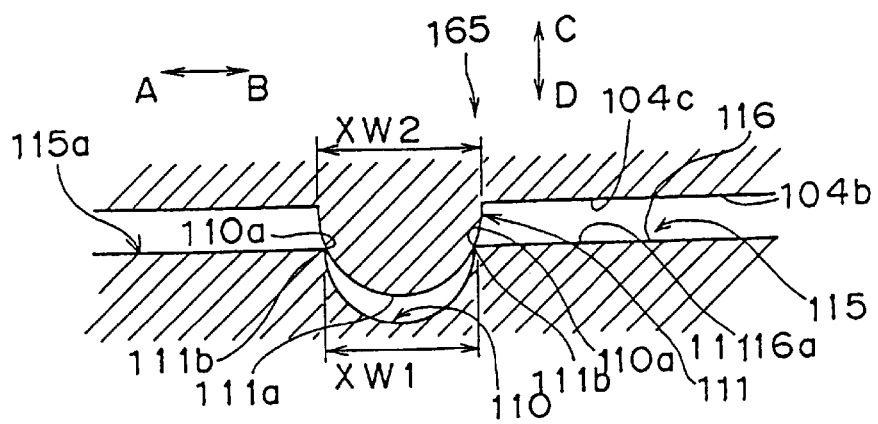
FIG. 19 is an enlarged sectional view of a sealing structure as shown in FIG. 18.
Figure 20:
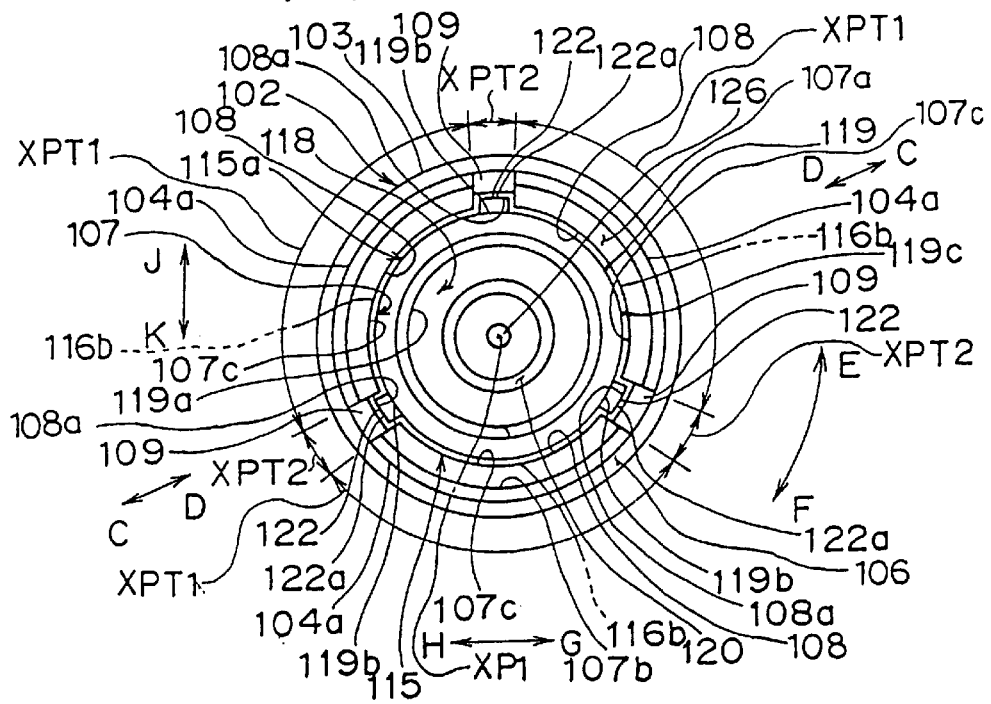
FIG. 20 is a view in the direction of the arrow II of FIG. 18.

On the other hand, on an inner peripheral face 104c side of the installation hole 104b, as shown in FIG. 18 or 19, a rib for holding 111 is formed in the shape of an annular stripe along the plane perpendicular to the directions as shown by the arrows A and B, at the position of the arrow B side rather than the three slits 109 above-mentioned of the inner peripheral face 104c.

The above-mentioned syringe 200 is comprised by unitedly combining the syringe body 102 and the syringe assembly supporting portion 105, and the syringe body 102 is comprised by unitedly combining the main cylindrical portion 103, taper 106 and the installation portion 104.

On the other hand, a needle installing unit 113 is installed on the installation hole 104b, as shown in FIG. 17 or 18 (In FIG. 18, a hub 121 and a needle 123, both described hereinafter, are omitted from the needle installing unit 113, for the convenience of explanation). The needle installing unit 113 has a needle installing body 115 in such a state that it is inserted in and installed on the installation hole 104b. The needle installing body 115 has a main body 115a basically formed in the shape of a cylinder, which can be linearly inserted into the installation hole 104b in the direction as shown by the arrow B through the introducing hole 107b and can be linearly pulled out the installation hole 104b into the syringe body 102 in the direction as shown by the arrow B. Furthermore, the main body 115a has a cylindrical portion 116 in the shape of a cylinder. On an outside peripheral face 116a side of the cylindrical portion 116, a groove for holding 110, annularly formed in the shape of a stripe along the plane perpendicular to the direction of the axis center of the cylindrical portion 116, that is, in the direction of the axis center of the main body 115a (which corresponds with the axis center XP1 in the case of the present embodiment), that is, in the directions as shown by the arrows A and B in the figure, is formed along the outside peripheral face 116a. On this occasion, this groove for holding 110 is attachably and detachably contacted and engaged with the rib for holding 111 of the installation hole 104b with a predetermined contact pressure, and by this engagement the needle installing unit 115 is attachably and detachably engaged and connected with the installation hole 104b.

The cross section of the plane including the axis center XP1 of the rib for holding 111 is almost circular as shown in FIG. 19, then the closer the width of the rib for holding 111 in the directions as shown by the arrows A and B is to a top end portion 111a, the narrower, and the farer it is from the top end portion 111a, that is, the closer in the direction as shown by the arrow C in the figure, the centrifugal direction from the axis center XP1, the wider. On this occasion, the maximum width of the rib for holding 111 in the directions as shown by the arrows A and B (the width of the rib for holding 111 near its bottom) is a width XW2. In the present embodiment, the width XW2 of the rib for holding 111 is wider than the width XW1 in an opening portion 110a of the groove for holding 110 in the directions as shown by the arrows A and B, thereby the engagement between the rib for holding 111 and the groove for holding 110 realizes in such a manner that a part of the top end portion 111a side of the rib for holding 111 is inserted into the groove for holding 110. In other words, the engagement between the rib for holding 111 and the groove for holding 110 realizes by annularly contacting predetermined contact portions 111b, 111b of the surface of the rib for holding 111 and the opening portion 110a of the groove for holding 111 with a line along the plane perpendicular to the axis center XP1 (FIG. 19 is a sectional view, so the point contate state is shown.). The groove for holding 110 and the rib for holding 111 above-mentioned comprises a sealing structure 165 for engaging the needle installing body 115 with the installation hole 104b and for sealing the portion between the needle installing body 115 and the installing hole 104b.

Concerning the cylindrical portion 116, as shown in FIG. 18, the distance XL3 from the axis center XP1 to the outside peripheral face 116a in the directions as shown by the arrows C and D (that is, the half size of the outside diameter) is slightly smaller than the distance XL1 from the axis center XP1 to the inner peripheral face 104c in the directions as shown by the arrows C and D in the installation hole 104b (that is, the half size of the inner diameter), then in such a state that the main body 115a is engaged with the installation hole 104b, between the inner peripheral face 104c of the installation hole 104b and the outside peripheral face 116a of the cylindrical portion 116, a space XL7 is formed in the directions as shown by the arrows C and D as a clearance.

On the other hand, as shown in FIG. 18, on the arrow A side of the figure which is the top end side of the main body 115a, a cylindrical portion 119 in the shape of a cylinder provided being united with the cylindrical portion 116, extending in the direction as shown by the arrow A, coaxially with the cylindrical portion 116, on the arrow A side of the cylindrical portion 116, opening in the direction as shown by the arrow A, is formed. The cylindrical portion 119 extends in the direction as shown by the arrow A, passing through the inside of the installation hole 104b, the stopper portion 107 and the introducing hole 107b. And, concerning the cylindrical portion 119, the distance XL4 from the axis center XP1 to an outside peripheral face 119c of the cylindrical portion 119 in the directions as shown by the arrows C and D (that is, the half size of the outside diameter) is slightly smaller than the distance XL2 from the axis center XP1 to the apical portion 107c in the directions as shown by the arrows C and D in the stopper portion 107 of the installation hole 104b (that is, the half size of the inner diameter), then in such a state that the needle installing body 115 is engaged with the installation hole 104b, a space XL5 is formed between the stopper portion 107 and the outside peripheral face 119c of the cylindrical portion 119 in the directions as shown by the arrows C and D as a clearance.

Inside of the cylindrical portion 119, a tapped hole for hub 118 for screwing and installing the hub 121 mentioned hereinafter on the main body 115a is formed such that a thread 119a is formed on the inner peripheral face side of the cylindrical portion 119. On the arrow A side in the figure which is the top end side of the main body 115a, a taper for hub 120 in the shape of a cylinder provided being united with the cylindrical portion 116, projecting and extending in the direction as shown by the arrow A coaxially with the cylindrical portion 116 on the arrow A side of the cylindrical portion 116, is formed. The taper for hub 120 is located in the center of the inside of the cylindrical portion 119. The form of this taper for hub 120 is taper such that the closer its outside diameter is to the direction as shown by the arrow A, the smaller it is.

On the other hand, at the end portion of the arrow A side of the cylindrical portion 116, an abutting end face 116b is formed, being almost annularly located, by the difference between the space XL3 of the cylindrical portion 116 and the space XL4 of the cylindrical portion 119. The abutting end face 116b is located, corresponding to a side portion 108b of the arrow B side of each projecting body 108 of the stopper portion 107, approaching the arrow B side. That is, the abutting end face 116b is free to abut on the side portion 108b of each projecting body 108 of the stopper portion 107 in the direction as shown by the arrow B. The three projecting bodies 108 of the stopper portion 107 are formed, extending around a circular arc at the predetermined pitch XPT1 with the axis center XP1 as its center, as mentioned before, and between the projecting bodies 108 and 108, the chipped portion 108a, extending around a circular arc at the predetermined pitch XPT2 with the axis center XP1 as its center, is formed. Since the abutting end face 116b is formed corresponding to these three projecting bodies 108, the abutting end face 116b is comprised of the three portions almost annularly located, these respective portions are formed extending around a circular arc at the pitch XPT1 with the axis center XP1 as its center, and between these respective portions the portion excluding the abutting end face 116b is formed extending around a circular arc at the pitch XPT2 with the axis center XP1 as its center.

Of the outside peripheral face 119c of the cylindrical portion 119, the portion from the position XK1 adjacent to the abutting end face 116b to the top end position XK2 of the main body 115a (that is, the top end position of the arrow A side of the cylindrical portion 119) is an interference avoidance face 119b. That is, since the abutting end face 116b is comprised of three portions correponding to the three projecting bodies 108, the interference avoidance face 119b is also comprised of three portions corresponding to the three projecting bodies 108.

Of the end portion of the arrow A side of the cylindrical portion 116, at the portion excluding the abutting end face 116b, that is, at the three portions extending around a circular arc at the pitch XPT2, positioning among the three portions extending around a circular arc at the pitch XPT1, comprising the abutting end face 116b, projection portions 122 are respectively formed, projecting in the direction as shown by the arrow A rather than the position of the abutting end face 116b. Each projection portion 122 projects in the direction as shown by the arrow C rather than the outside peripheral face 119c of the cylindrical portion 119, and the distance XL3' from the axis center XP1 to an end face 122a of the arrow C side of the projection portion 122 in the directions as shown by the arrows C and D is almost equal to the distance XL3 from the axis center XP1 to the outside peripheral face 116a in the directions as shown by the arrows C and D of the cylindrical portion 116. That is, the distance XL3' is slightly smaller than the distance XL1 from the axis center XP1 to the inner peripheral face 104c in the directions as shown by the arrows C and D in the installation hole 104b, then in such a state that the needle installing body 115 is engaged with the installation hole 104b, a space XL6 is formed in the directions as shown by the arrows C and D between the end portion 122a of the projection portion 122 and the inner peripheral face 104c of the installation hole 104b as a clearance.

Each projection portion 122 is located corresponding to each chipped portion 108a of the stopper portion 107, thereby each projection portion 122 is located between the projecting bodies 108, 108 of the stopper portion 107. That is, if the peripheral direction which center is the axis center XP1 is the directions as shown by the arrows E and F in the figure and the end faces of the arrows E and F sides in each projecting body 108 are abutting faces in peripheral direction 107d, 107d, each projection portion 122 is located between the abutting faces in peripheral direction 107d, 107d of the projecting bodies 108, 108. Then, the oscillation of each projection portion 122 in the directions as shown by the arrows E and F to the installation hole 104b, that is, the oscillation of the needle installing body 115 in the directions as shown by the arrows E and F to the installation hole 104b is obstructed by abutting these projection portions 122 on the abutting face in peripheral direction 107d of each projecting body 108.

Figure 21:
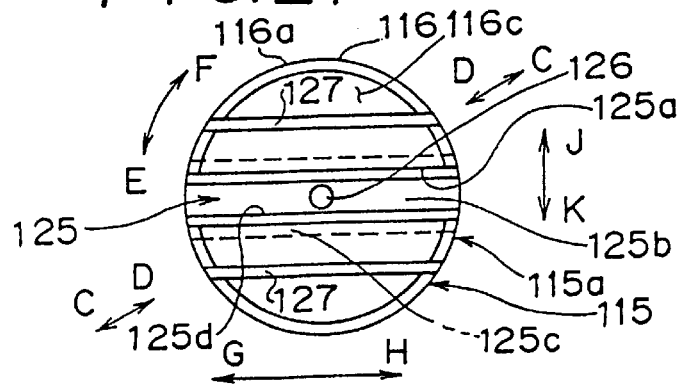
FIG. 21 is a view in the direction of the arrow III of FIG. 18.

An engagement groove 125 is provided for the direction as shown by the arrow A with the cylindrical portion 116, forming an opening portion 125a at an end face 116c of its arrow B side. The engagement groove 125 is a groove penetrating the cylindrical portion 116 in the directions as shown by the arrows G and H in the figure, perpendicular to the directions as shown by the arrows A and B, as shown in FIG. 21. The engagement groove 125 is basically comprised of an introducing portion 125b adjacent to the opening portion 125a and a holding portion 125c communicating with the arrow A side of the introducing portion 125b. Between the introducing portion 125b and the holding portion 125c, a constriction portion 125d is formed such that the space in the directions as shown by the arrows J and K of the figure perpendicular to the directions as shown by the arrows G and H is getting narrow from the both up and down sides in the center direction (in the present embodiment, the direction for the axis center XP1).

Deformation expediting grooves 127, 127 are provided with the cylindrical portion 116 on the arrows J and K sides of the engagement groove 125, extending from the end face 116c of the cylindrical portion 116 in the direction as shown by the arrow A. These deformation expediting grooves 127, 127 are also the grooves penetrating the cylindrical portion 116 in the directions as shown by the arrows G and H.

And, a medical liquid flow hole 126 formed extending in the directions as shown by the arrows A and B between the cylindrical portion 116 and the taper for hub 120 is provided with the main body 115a, communicating the outside of the top end side of the taper for hub 120 and the holding portion 125c of the engagement groove 125 with each other.

The main body 115a of the needle installing body 115 is comprised of the cylindrical portion 116, the cylindrical portion 119 and the taper for hub 120.

The needle installing unit 113 has the hub 121 excluding the needle installing body 115 above-mentioned. The hub 121 is formed in the shape of a cap covered by the taper for hub 120 of the main body 115a in water tight state, as shown in FIG. 17. On the arrow B side of the hub 121, a screw engagement portion 121a is provided, projecting in the shape of a flange. That is, in this state, the screw engagement portion 121a fits in the thread 119a of the tapped hole for hub 118 of the cylindrical portion 119. That is, the hub 121 is free to screw and install in the main body 115a through the screw engagement portion 121a and the thread 119a of the cylindrical portion 119. The needle 123, which is the liquid flow tube member, is connected with the top end side of the hub 121. The inside of the needle 123 (that is, the space where a medical liquid flows) communicates with an inside 121b of the hub 121, then communicates with the medical liquid flow hole 126 of the main body 115a through the inside 121b (In case where the needle such as the needle 123 is used as the liquid flow tube member, the syringe assembly of the present invention is one for injecting a medical liquid or for blood collection. However, a tube member for blood transfusion or intravenous drip excluding a needle can be also used as the liquid flow tube member. The example using a tube member 223 as the liquid flow tube member is shown by the two-dot chain line of FIG. 17).

On the other hand, the piston 139 is provided with the syringe assembly 101, as shown in FIG. 17 (FIG. 17 is a typical cross section of the syringe assembly 101, but the sides of a piston body 140, an outer press plate 142 and an inner press plate 143, described hereinafter, of the piston 139 not their sections, are shown for convenience.).

The piston 139 has the bar-shaped piston body 140 extending in the directions as shown by the arrows A and B, the piston body 140 is comprised such that two congruent plate portions 140a, each which is a plate shaped rectangle especially long in the directions as shown by the arrows A and B, are unitedly cross provided with each other such that the sections thereof form the shape of a cross. The width perpendicular to the directions as shown by the arrows A and B of the plate face of the plate portion 140a is almost equal to the inside diameter in the engagement rib 103b of the main cylindrical portion 103, and the piston body 140 is inserted into the main cylindrical portion 103 through the opening end 103a from the arrow A side of the piston body 140.

On each plate portion 140a of the piston body 140, notches 141 are formed from both side portions 140b, 140b of respective plate portions 140a, 140a in the direction of the axis center (that is, the axis center XP1) of the piston body 140 in the shape of a wedge near the direction as shown by the arrow A. Four notches 141 are provided at the positions adjusted one another in the directions as shown by the arrows A and B.

The outer press plate 142, which plate face is a circular plate perpendicular to the directions as shown by the arrows A and B, is provided at the end portion side of the arrow B side of the piston body 140, being united with the piston body 140, and coaxial with the piston body 140. The diameter of the outer press plate 142 is fully bigger than the inside diameter of the main cylindrical portion 103.

As shown in FIG. 17, the inner press plate 143, which plate face is a circular plate perpendicular to the directions as shown by the arrows A and B, is provided at the end portion side of the arrow A side of the piston body 140 being united with the piston body 140 and coaxial with the piston body 140 (Therefore, the inner press plate 143 is positioned inside the main cylindrical portion 103.). The diameter of the inner press plate 143 is almost equal to the inside diameter of the main cylindrical portion 103 (Therefore, the diameter of the inner press plate 143 is bigger than the inside diameter in the engagement rib 103b of the main cylindrical portion 103.).

As shown in FIG. 17, a packing support portion 145 projecting in the direction as shown by the arrow A is provided in an almost cylindrical shape with the inner press plate 143 on the arrow A side. A packing 146, formed in the shape of a ring, being comprised of flexible resin is engaged and installed on the packing support portion 145. That is, the inside of the syringe body 102 can be closed between the arrows A and B sides of the packing 146 in a water tight (air tight) state by the packing 146.

The hub engagement portion 147 is unitedly provided on the arrow A side of the packing support portion 145. The hub engagement portion 147 is comprised of the cylindrical portion 147a extending in the directions as shown by the arrows A and B and an insertion portion 147b provided on the arrow A side of the cylindrical portion 147a. The insertion portion 147b is semi-pherical shape which diameter is bigger than the cylindrical portion 147a, and a spherical face 147c side of the insertion portion 147b is located, facing the arrow A side. The diameter of the cylindrical portion 147a is almost equal to the space in the directions as shown by the arrows J and K of the figure in the chipped portion 125d of the engagement groove 125 provided with the main body 115a of the needle installing body 115. The diameter of the insertion portion 147b is smaller than the holding portion 125c of the engagement hole 125 in the directions as shown by the arrows J and K.

The syringe assembly 101 is comprised as mentioned before, and the assembly of the syringe assembly 101 is executed by the following steps.

That is, the syringe 200, the needle installing unit 113 and the piston 139 which are the components of the syringe assembly 101 are prepared. In this case, the needle installing unit 113 is set in such a state that the needle installing body 115 and the hub 121 are separated from each other. And, the needle 123 is connected with the hub 121 in advance.

Firstly, the piston 139 is installed on the syringe 200. Next, the needle installing body 115 is installed on the syringe 200. That is, the installation of the needle installing body 115 is executed in such a manner that the needle installing body 115 is inserted into the installation hole 104b from the introducing hole 107d side of the hub installation portion 104. That is, the arrow B side of the needle installing body 115, that is, the end face 116c side is pressed from the introducing hole 107b of the installation portion 104 to the opening top end face 107a, and in the afore-mentioned state, the needle installing body 115 is pushed to the syringe 200 in the direction as shown by the arrow B. On this occasion, as explained before, since the open top end face 107a is formed in the shape of a taper, the force pressing the open top end face 107a by the needle installing body 115 becomes to be the force enlarging the portion near the stopper portion 107 of the installation portion 104 in the centrifugal direction with respect to the axis center XP1, that is, in the direction as shown by the arrow C of the figure. In addition, since the arrow A side of the installation portion 104 is divided into the three installation portion pieces 104a by the three slits 109, as mentioned before, the arrow A side of the installation portion 104, that is, the portion near the stopper portion 107 is easily enlarged in the direction as shown by the arrow C by the pressing force from the needle installing body 115.

While the portion near the stopper portion 107 is enlarged by the pressing force from the needle installing body 115 in the direction as shown by the arrow C, the needle installing body 115 is further pressed to the syringe 200 in the direction as shown by the arrow B, thereby the groove for holding 110 of the needle installing body 115 is engaged with the rib for holding 111 of the installation hole 104b. By the engagement between the groove for holding 110 and the rib for holding 111, the needle installing body 115 and the installation hole 104 are engaged with each other, the abutting end face 116b of the needle installing body 115 is located, corresponding to and approaching the arrow B side of the stopper portion 107, and the three projecting portions 122 of the needle installing body 115 are respectively located between the three projecting bodies 108 of the stopper portion 107.

Since the apical portion 107c of the stopper portion 107 is formed in the shape of a face extending in the directions as shown by the arrows A and B, as mentioned before, it serves as a guide for inserting the needle installing body 115 in the direction as shown by the arrow B at the time of the installation of the needle installing body 115. In addition, the apical portion 107c is not sharp in the direction as shown by the arrow D, thereby the stopper portion 107 is reinforced. Then, when the needle installing body 115 and the stopper portion 107 are rubbed together at the time of installation, chipping a part of the stopper portion 107 off is effectively prevented. Then, at the time of assembly, inserting an extraneous substance into the inside space 102a of the syringe body 102 or the like is prevented, thereby high safety is exercised.

Subsequently, the hub 121 connecting the needle 123 therewith is covered on the taper for hub 120 of the needle installing body 115 and is screwed and installed on the tapped hole for hub 118 of the needle installing body 115 so as to install on and connect with the needle installing body 115, then the assembly of the syringe assembly 101 finishes. When the hub 121 is screwed and installed, the force for oscillating the needle installing body 115 with the axis center XP1 as its center to the syringe 200 in the directions as shown by the arrows E and F by the screwing movement of the hub 121 acts. However, the three projection portions 122 of the needle installing body 115 abuts on the abutting face in peripheral direction 107d of each projecting body 108 of the stopper portion 107 in the directions as shown by the arrows E and F, then by the abutting these projection portions 122 and the projecting body 108 on each other, the oscillation of the needle installing body 115 in the directions as shown by the arrows E and F is prevented. Then, the screwing and installing the hub 121 is easily executed. Besides, as explained before, almost all of the works in the assembly of the syringe assembly 101 is executed by pressing and installing, then the works are easy without complex work.

The syringe assembly 101 assembled as mentioned before is used, and after the use, disposal is executed by the following ways.

At first, the assembled syringe assembly 101 is filled with a liquid injection medium 159. The filling up of the injection medium 159 is executed in such a manner that the piston 139 is pulled out so as to act negative pressure on the inside space 102a of the syringe body 102, and the injection medium 159 is sucked from the top end side of the needle 123. The injection medium 159 flows into the inside space 102a of the syringe body 102 through the needle 123, the inside 121b of the hub 121, the medical liquid flow hole 126, and the engagement hole 125 so as to fill up.

Although the space XL7 is formed between the cylindrical portion 116 of the main body 115a of the needle installing body 115 and the installation hole 104b as a clearance, the groove for holding 110 of the needle installing body 115 and the rib for holding 111 of the installation hole 104b are engaged with each other. Then, by a predetermined contacting pressure acting between the needle installing body 115 and the installation hole 104b, between the groove for holding 110 and the rib for holding 111, that is, by the sealing pressure, the portion between the needle installing body 115 and the installation hole 104b is sealed, then there is no liquid leak. Since the engagement between the groove for holding 110 and the rib for holding 111 is executed by the line contact between the opening portion 110a and the contact portion 111b as mentioned before, high sealing efficiency is exercised in comparison with face contact, preferably.

After filling up of the injection medium 159, a medical liquid is injected into a patient, and thereafter the syringe assembly 101 is disposed of.

Figure 22:
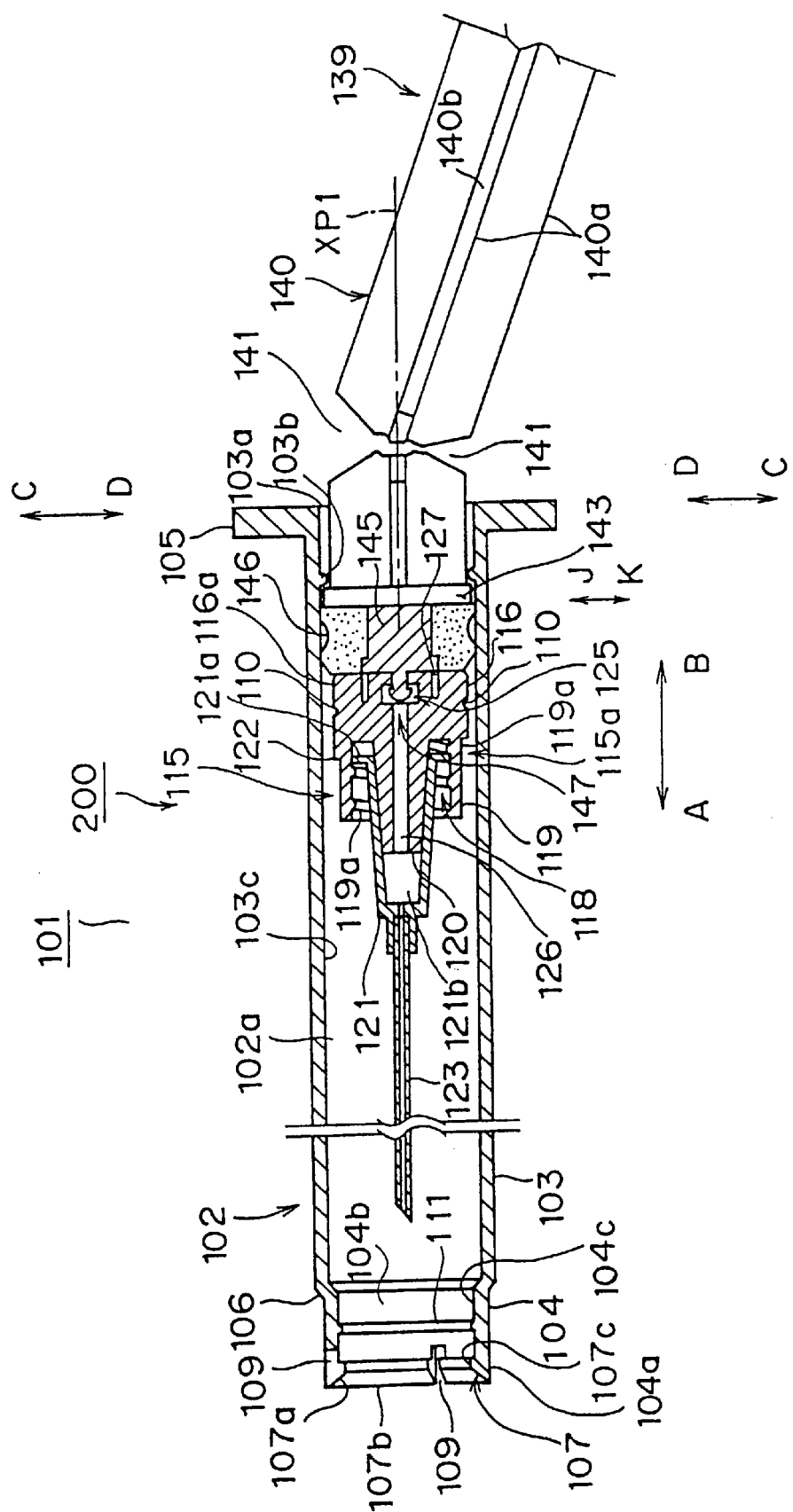
FIG. 22 is a view showing bending and taking of the piston in the syringe assembly as shown in FIG. 17.

Firstly, the piston 139 and the needle installing body 115 are engaged with each other. That is, the piston 139 is further pressed in the direction as shown by the arrow A. By this press, the insertion portion 147b of the hub engagement portion 147 of the piston 139 rushes into the introducing portion 125b of the engagement groove 125 of the needle installing body 115, as shown in FIG. 22. On this occasion, since the spherical face 147c is formed at the top end of the insertion portion 147b, the insertion portion 147b which rushed easily passes the chipped portion 125c, and reaches the holding portion 125c. The cylindrical portion 147a extending on the arrow B side of the insertion portion 147b exists penetrating the chipped portion 125c in the directions as shown by the arrows A and B. That is, the piston 139 and the needle installing body 115 are engaged with each other.

The pressing force in the direction as shown by the arrow A acts on the insertion portion 147b, thereby the pressing force in the direction as shown by the arrow A also acts on the needle installing body 115. However, the needle installing body 115 abuts on the stopper portion 107 in the direction as shown by the arrow A in the abutting end face 116b. As the result, it is supported by the stopper portion 107. Then, the needle installing body 115 hardly move in the direction as shown by the arrow A even if pressing force is received. Therefore, the needle installing body 115 does not get out the installation hole 104b to the outside in the direction as shown by the arrow A, then it is safe.

After the piston 139 and the hub 113 are engaged with each other, the piston 139 is pulled with respect to the syringe 200 in the direction as shown by the arrow B, thereby the needle installing body 115 engaged with the piston 139 through the hub engagement portion 147 and the engagement groove 125 is pulled with respect to the syringe 200 in the direction as shown by the arrow B together with the piston 139, as shown in FIG. 22. Then, the engagement between the needle installing body 115 and the installation hole 104b is released, the needle installing body 115, the hub 121 installed on and connected with the needle installing body 115 and the needle 123 are inserted into the inside space 102a of the syringe body 102. The piston 139 is further pulled to the position where the inner press plate 143 abuts on the engagement rib 103b of the main cylindrical portion 103 of the syringe body 102, as shown in FIG. 22, and then the piston 139 is stopped. On this occasion, the top end of the needle 123 is completely inserted into the inside space 102a.

The inner press plate 143 of the piston 139 is stopped by the engagement rib 103b, thereby springing a needle 136 installed on the hub 113 engaged with the piston 139 to the outside of the syringe body 102 by excessively pulling the piston 139 in error is prevented, and the accident such as secondary infection owing to the hurt of an arm with the needle 123 is prevented.

In such a state that the inner press plate 143 of the piston 139 is stopped by the engagement rib 103b, the position of the notch 141 formed at the piston body 140 of the piston 139 almost corresponds to the position of the opening end 103a of the syringe body 102 in the directions as shown by the arrows A and B, as shown in FIG. 22.

Subsequently, while the syringe body 102 is fixed with one hand, the piston 139 is gripped with the other hand, and as shown in FIG. 22, the force in the direction as shown by the arrow C is given on the piston 139. By adding the force in the direction as shown by the arrow C to the piston 139 with respect to the syringe body 102, bending stress is added on the piston body 140 such that the engagement rib 103b and the opening end 103a of the syringe body 102 are supporting points. Then, the piston body 140 is broken in the notch 141 which is relatively weakly formed in its structure with respect to bending stress in the piston body 140, and the piston body 140 is separated into the arrow A side portion and the arrow B side portion forming boundary by the notch 141. Subsequently, the portion of the syringe body 102 side and the portion of the outer press plate 142 of the piston 139 which are broken and taken are disposed of.

Figure 23:
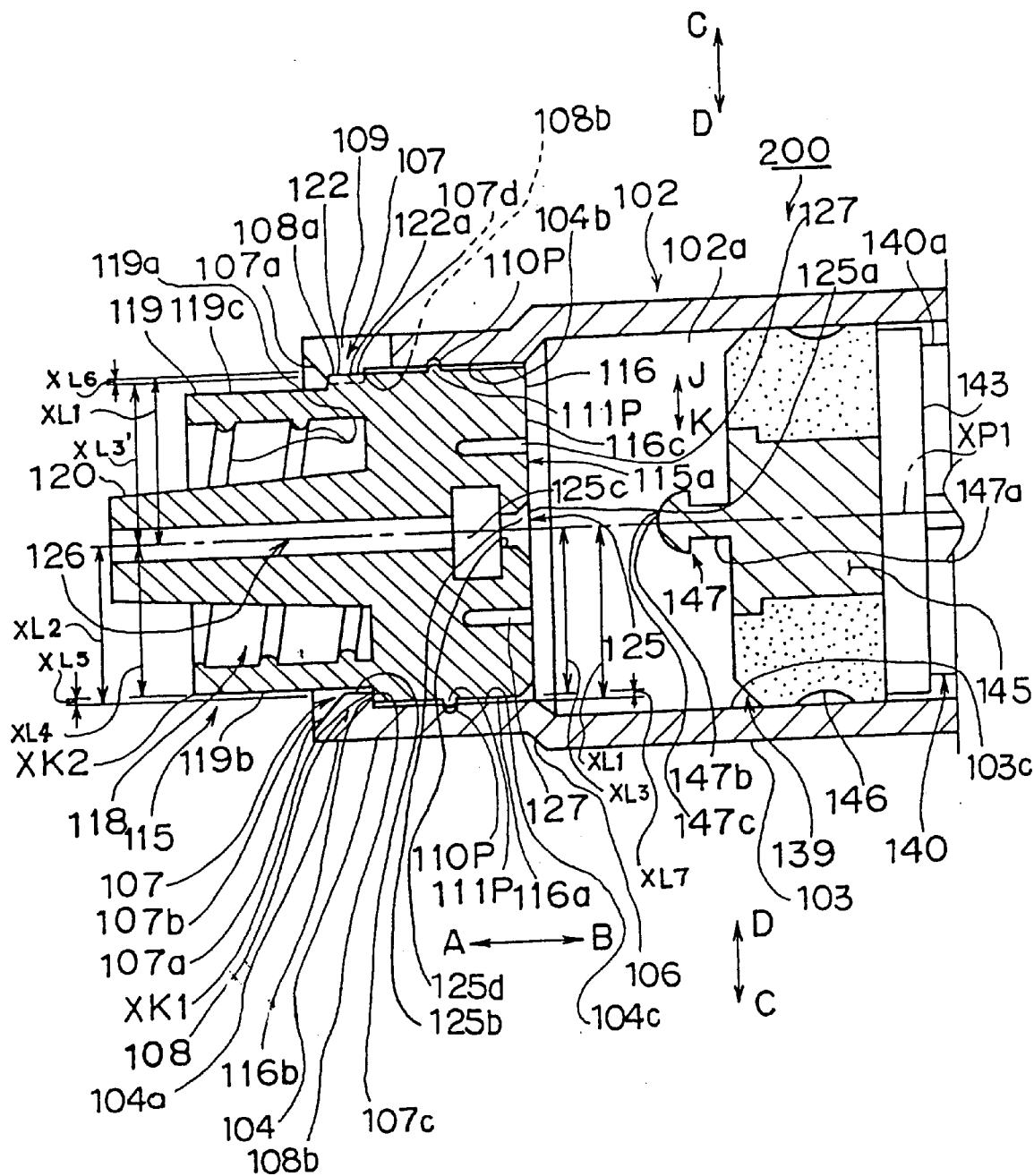
FIG. 23 is an another example of the syringe assembly according to the present invention and a sectional view near its installation hole.

In the above-mentioned embodiment, the groove for holding 110 and the rib for holding 111 which are a groove and a projection, comprising the sealing structure 165, are formed on the needle installing body 115 side and the installation hole 104b side, respectively. However, the groove and the projection comprising the sealing structure may be respectively formed on the installation hole 104b side and the needle installing body 115 side. For instance, as shown in FIG. 23, a groove for holding 110P and a rib for holding 111P, which are a groove and a projection comprising a sealing structure, may be respectively formed on the installation hole 104b side and on the needle installing body 115 side.

In the present embodiment, the slits 109 are three and the projecting bodies 108 are also three. However, any number of the Slits is available, and one or more than one projecting bodies of the stopper portion are available. For instance, four slits and four projecting bodies may be formed.

Figure 24:
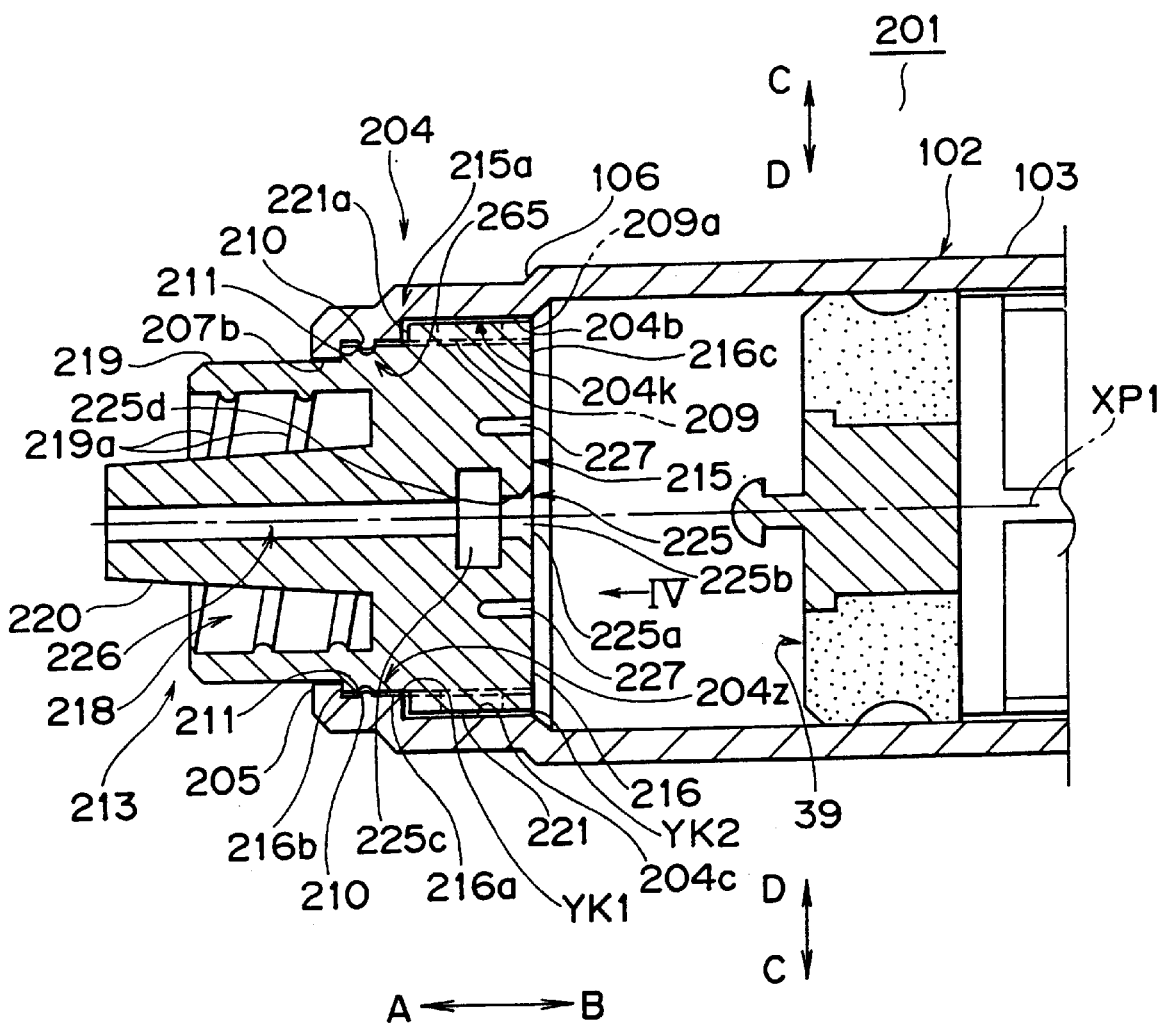
FIG. 24 is an another example of the syringe assembly according to the present invention and a sectional view near its installation hole.
Figure 25:
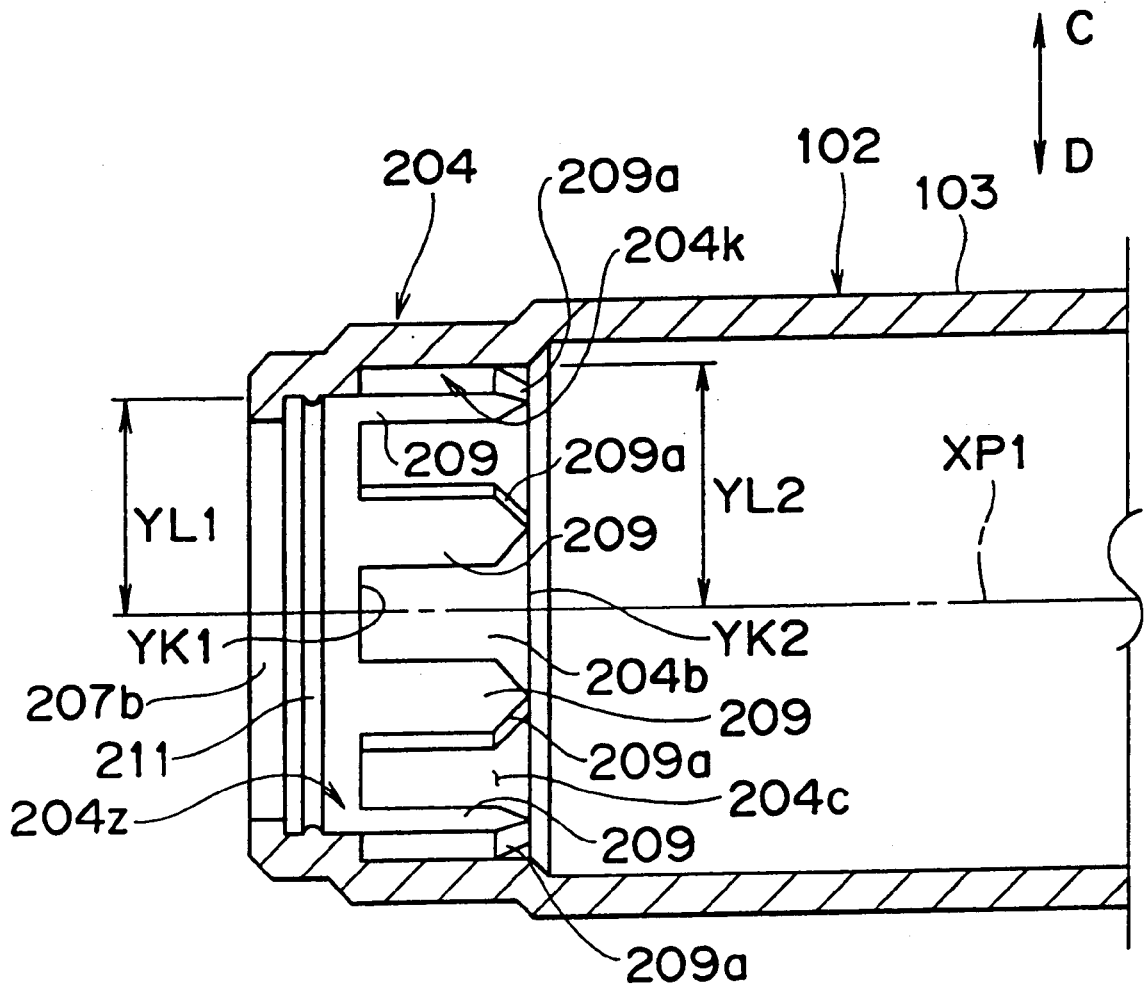
FIG. 25 is a sectional view showing only syringe body side of the syringe assembly as shown in FIG. 24.

In the present invention, a LUER lock type of a syringe assembly, such as the syringe assembly 101 beforementioned, is adopted. However, an another LUER lock type of a syringe assembly can be also adopted as the syringe assembly according to the present invention. For instance, a syringe assembly 201 as shown in FIGS. 24 through 27 is possible. The syringe assembly 201 is different from the above-mentioned syringe assembly 101 concerning its structure in the liquid flow tube holding memeber (the needle installing body 115 in the syringe assembly 101) and the holding member installing hole (the installation hole 104b in the syringe assembly 101) (The other portions are comprised in almost similar way.). That is, the main cylindrical portion 103 formed in the shape of a cylinder is provided with the syringe body 102 of the syringe assembly 201, in a similar way to the syringe assembly 101, as shown in FIG. 24. On the arrow A side of the main cylindrical portion 103, an installation portion 204 in the shape of a cylinder is formed, extending in the direction as shown by the arrow A, unitedly connecting, through the taper 106 in the shape of a funnel. As shown in FIG. 25, the installation portion 204 has an installation hole 204b in the shape of a cylinder, formed the inside thereof. At the top end of the arrow A side of the installation portion 204, an end wall portion 205 perpendicular to the directions as shown by the arrows A and B, is formed projecting in the axis center XP1 direction. An introducing hole 207b open in the almost circular shape penetrating the end wall portion 205 in the directions as shown by the arrows A and B is provided with this end wall portion 205, connecting the installation hole 204b and the outside of the syringe body 102 with each other in the directions as shown by the arrows A and B. At the position of the arrow B side of the end wall portion 205 on an inner peripheral face 204c side of the installation hole 204b, as shown in FIG. 25, the rib for holding 211 is formed in the shape of a circle of a stripe along the plane perpendicular to the directions as shown by the arrows A and B. Concerning the installation hole 204b, of the inner peripheral face 204c of the installation hole 204b, the A side portion from the position YK1 is a front installation portion 204z forming a boundary by the the position YK1 of the arrow B side rather than the rib for holding 211, and the portion from the position YK1 to the position YK2 bounding on the taper 106 is a back installation portion 204k. The basic distance YL1 from the inner peripheral face 204c of the installation hole 204b in the front installation portion 204z to the axis center XP1 (that is, the distance from the inner peripheral face 204c in the portion excluding the rib for holding 211 to the axis center XP1) is smaller than the basic distance YL2 from the inner peripheral face 204c of the installation hole 204b in the back installation portion 204k to the axis center XP1.

Figure 27:
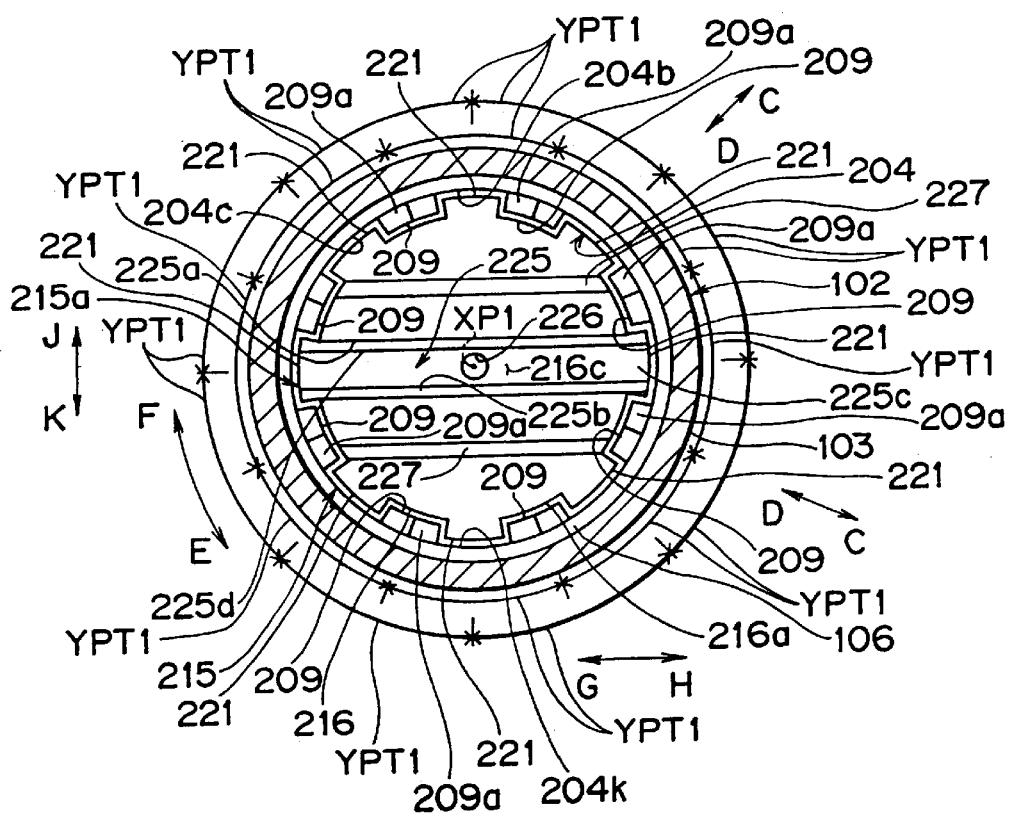
FIG. 27 is a view in the direction of the arrow IV of FIG. 24.

On the inner peripheral face 204c side of the installation hole 204b, at the back installation portion 204k, as shown FIG. 25 or 27, a plurality of stopper portions 209 comprised of projecting bodies are formed projecting for the axis center XP1. Each stopper portion 209 is formed in the shape of a stripe, extending in the directions as shown by the arrows A and B between the positions YK1 and YK2. These stopper portions 209 (eight in the present embodiment) are located at a predetermined pitch YPT1 (45 degrees pitch in the present embodiment) with the axis center XP1 as its center, as shown in FIG. 27. The distance from each stopper portion 209 to the axis center XP1 is equal to the basic distance YL1 from the inner peripheral face 204c of the installation hole 204b in the front installation portion 204z to the axis center XP1. That is, the arrow D side end of each stopper portion 209 and the inner peripheral face 204c of the installation hole 204b in the front installation portion 204z, or the inner peripheral face 204c near the postion YK1 smoothly connect with each other in the directions as shown by the arrows A and B. The end portion 209a of the arrow B side of each stopper portion 209 is in the shape of a wedge sharp in the direction as shown by the arrow B.

Figure 26:
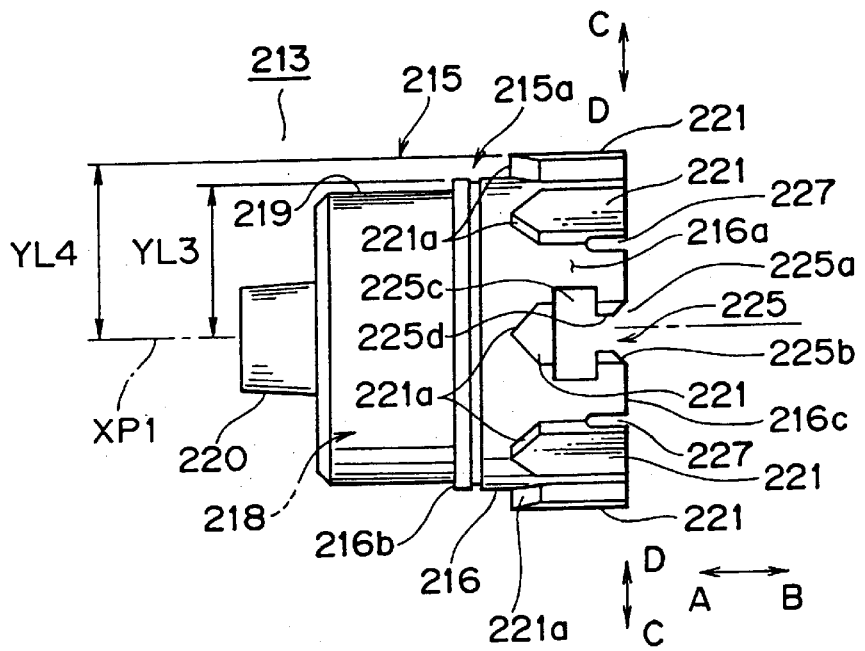
FIG. 26 is a side view showing only needle installation body of the syringe assembly as shown in FIG. 24.

On the other hand, as shown in FIG. 24, a needle installing unit 213 is installed in the installation hole 204b. The needle installing unit 213 has a needle installing body 215 in the state of being inserted and installed in the installation hole 204b. The needle installing body 215 has a main body 215a basically formed in the cylindrical shape, which can be linearly inserted into the installation hole 204b from the piston installation side in the direction as shown by the arrow A and can be linearly pulled out of the installation hole 204b into the syringe body 102 in the direction as shown by the arrow B, as shown in FIG. 24 or FIG. 26, and the main body 215a has a cylinder portion 216 in the shape of a cylinder. On an outer peripheral face 216a side of the cylinder portion 216, a groove for holding 210 formed in the shape of a stripe of a circle in the direction of the axis center of the cylinder portion 216, that is, in the direction of the axis center of the main body 215a (corresponds with the axis center XP1 in the case of the present embodiment), that is, along the plane perpendicular to the directions as shown by the arrows A and B in the figure, is formed along the outer peripheral face 216a. This groove for holding 210 is attachably and detachably contacted and enagaged with the rib for holding 211 of the installation hole 204b with a predetermined contact pressure, and by this engagement, the needle installing body 215 is attachably and detachably engaged and connected with the installation hole 204b.

The section of the plane including the axis center XP1 of the rib for holding 211 is almost semi-circular in a similar to the case of the rib for holding 111 of the syringe assembly 101 as shown in FIG. 19. Then, the closer to the top end portion of the rib for holding 211, the narrower the width in the directions as shown by the arrows A and B is, the farer from the top end portion, the wider the width is. In a similar way to the case of the syringe assembly 101, the maximum width of the rib for holding 211 in the directions as shown by the arrows A and B (the width near the bottom of the rib for holding 211) is broader than the width of the groove for holding 210 in the opening portion in the directions as shown by the arrows A and B, thereby the engagement between the rib for holding 211 and the groove for holding 210 is realized in such a manner that the a part of the top end portion side of the rib for holding 211 is inserted into the groove for holding 210. That is, the engagement between the rib for holding 211 and the groove for holding 210 is realized by annularly contacting a predetermined contact portion of the surface of the rib for holding 211 and the opening portion of the groove for holding 210 with each other with line along the plane perpendicular to the axis center XP1. The groove for holding 210 and the rib for holding 211 comprise a sealing structure 265 for engaging the needle installing body 215 with the installation hole 204b and for sealing the portion between the needle installing body 215 and the installation hole 204b.

As shown in FIG. 24 or 26, concerning the cylindrical portion 216, the basic distance YL3 from the axis center XP1 to the outer peripheral face 216a in the directions as shown by the arrows C and D is smaller than the distance YL1 from the axis center XP1 to the inner peripheral face 204c side in the directions as shown by the arrows C and D in the installation hole 204b. Then, in such a state that the main body 215a is engaged with the installation hole 204b, a space in the directions as shown by the arrows C and D is formed as a clearance between the inner peripheral face 104c excluding the rib for holding 211 in the front installation portion 204z of the installation hole 204b and the outer peripheral face 216a of the cylindrical portion 216 and between the arrow D side end portion of the stopper portion 209 in the back installation portion 204k of the installation hole 204b and the outer peripheral face 216a of the cylindrical portion 216.

At the portion corresponding to the back installation portion 204k of the outer peripheral face 216a of the cylindrical portion 216, as shown in FIG. 24, 26 or 27, a plurality of abutting portions in peripheral direction 221 are provided projecting in the directions as shown by the arrow C. Each abutting portion in peripheral direction 221 is formed in the shape of a stripe extending in the directions as shown by the arrows A and B. These abutting portions in peripheral direction 221 (eight in the present embodiment) are located at the pitch YPT1 the same as the predetermined pitch YPT1 (45 degrees pitch in the present embodiment) with the axis center XP1 as its center, as shown in FIG. 27. As shown in FIGS. 24 through 26, the distance YL4 from the arrow C side end of each abutting portion in peripheral direction 221 to the axis center XP1 is slightly smaller than the basic distance YL2 from the inner peripheral face 204c excluding the position of each stopper portion 209 of the installation hole 204b in the back installation portion 204k to the axis center XP1. In such a state that the needle installing unit 213 is installed in the installation hole 204b, as shown in FIG. 24 or 27, each abutting portion in peripheral direction 221 is located fitting between the stopper portions 209, 209 adjacent to the peripheral direction. An end portion 221a of the arrow A side of each abutting portion in peripheral direction 221 is in the shape of a wedge sharp in the direction as shown by the arrow A.

In order to install the needle installing body 215 of the needle installing unit 213 in the installation hole 204b, the needle installing body 215 is inserted into the syringe body 102 from the piston installation side so as to insert into the installation hole 204b in the direction as shown by the arrow A and to engage through the sealing structure 265. When the needle installing body 215 is inserted into the installation hole 204b, the engagement between the abutting portion in peripheral direction 221 and the stopper portion 209 is preferably smoothly executed since the end portion 221a of the arrow A side of each abutting portion in peripheral direction 221 is in the shape of a wedge sharp in the direction as shown by the arrow A and the end portion 209a of the arrow B side of each stopper portion 209 is in the shape of a wedge sharp in the direction as shown by the arrow B.

As explained heretofore, in such a state that the needle installing unit 213 is installed in the installation hole 204b, each stopper portion 209 and each abutting portion in peripheral direction 221 are free to engage with each other in the peripheral direction, thereby if the needle installing unit 213 tries to oscillate in the peripheral direction with respect to the syringe body 102, each stopper portion 209 and each abutting portion in peripheral portion 221 are abutted on each other in the peripheral direction, and the oscillation is prevented.

On the other hand, as shown in FIG. 24 or 26, on the arrow A side of the figure which is the top end side of the main body 215a, on the arrow A side of the cylinder portion 216, a cylindrical portion 219 in the shape of a cylinder is formed, extending in the direction as shown by the arrow A, being coaxial with the cylinder portion 216, unitedly connecting with the cylinder portion 216, open in the direction as shown by the arrow A. The cylindrical portion 219 extends in the direction as shown by the arrow A passing through the inside of the installation hole 204b and the introducing hole 207b. The outside diameter of the cylindrical portion 219 is smaller than the inside diameter in the portion excluding the rib for holding 211 in the front installation portion 204z of the installation hole 204b, and is slightly smaller than the inside diameter of the introducing hole 207b. The outside diameter of the portion corresponding to the front installation portion 204z of the cylindrical portion 216 is bigger than the outside diameter of the cylindrical portion 219 and the inside diameter of the introducing hole 207b. Therefore, at the end portion of the arrow A side of the cylindrical portion 216, an abutting portion 216b is annularly formed enclosing the cylindrical portion 219 by the difference of the diameter between the cylinder portion 216 and the cylindrical portion 219. In such a state that the needle installing unit 213 is installed in the installation hole 204b, as shown in FIG. 24, the abutting portion 216b is located at the immediate position to the arrow B side of the end wall portion 205 (or the position abutted), then the needle installing body 215 is free to abut on the end wall portion 205 in the direction as shown by the arrow A through the abutting portion 216b.

Inside the cylindrical portion 219, a tapped hole for hub 218 for installing the hub (not shown) similar to the hub 121 adopted in the above-mentioned syringe assembly 101 in the main body 215a by screwing is formed, forming a thread 219a on the inner peripheral face side of the cylindrical portion 219. Furthermore, on the arrow A side of the figure which is the top end side of the main body 215a, a taper for hub 220 in the shape of a cylinder is formed on the arrow A side of the cylinder portion 216, projecting and extending in the direction as shown by the arrow A, being coaxial and unitedly connecting with the cylinder portion 216. The taper for hub 220 is located in the center of the inside of the cylindrical portion 219.

As shown in FIG. 24, an engagement groove 225 is provided for the direction as shown by the arrow A with the cylinder portion 216, forming an opening portion 225a at an end face 216c of the arrow B side. The engagement groove 225 is a groove penetrating the cylinder portion 216 in the directions as shown by the arrows G and H of the figure perpendicular to the directions as shown by the arrows A and B as shown in FIG. 27. The engagement groove 225 is basically comprised of an introducing portion 225b adjacent to the opening portion 225a and a holding portion 225c communicating and connecting with the arrow A side of the introducing portion 225b. Between the introducing portion 225b and the holding portion 225c, a chipped portion 225d is formed such that the space in the directions as shown by the arrows J and K of the figure perpendicular to the directions as shown by the arrows G and H is narrower from the both up and down sides in the center direction (in the present embodiment, the direction for the axis center XP1).

Furthermore, deformation expediting grooves 227, 227 are provided with the cylinder portion 216 on the arrows J and K sides of the engagement groove 225, extending from the end face 216c of the cylinder portion 216 in the direction as shown by the arrow A. These deformation expediting grooves 227, 227 are also grooves penetrating the cylinder portion 216 in the directions as shown by the arrows G and H.

A medical liquid flow hole 226 extending from the cylinder portion 216 to the taper for hub 220 in the directions as shown by the arrows A and B is provided with the main body 215a, communicating and connecting the outside of the top end side of the taper for hub 220 and the holding portion 225c of the engagement groove 225 with each other.

The needle installing body 215 which is the liquid flow tube holding member and the installation hole 204b which is the holding member installation hole of the syringe assembly 201 are comprised as explained heretofore.

The present invention has been explained on the basis of the embodiments presented herein. However, the embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

I claim:

1. A syringe assembly, comprising:

a syringe body having a cylindrical holding member installing hole at a top end thereof, said holding member installing hole defining a penetrating hole and communicating between an inside and an outside of said syringe body;

a piston installed in said syringe body, the piston being slidable in an axis center direction defined by said syringe body; and a liquid flow tube holding member capable of connecting a liquid flow tube member therewith, attachably and detachably connected to the syringe body at said holding member installing hole through a predetermined sealing structure, said syringe assembly further comprising:

said liquid flow tube holding member having a member main body that is linearly insertable into said holding member installing hole in said axis center direction of said syringe body and capable of being linearly pulled out of said holding member installing hole into said syringe body in said axis center direction of said syringe body;

said sealing structure comprising one of a groove and a projection on an outer peripheral portion of said member main body and the other of said groove and said projection on an inner peripheral portion of said holding member installing hole, the groove and the projection being annularly formed along a plane perpendicular to said axis center direction of said member main body, said groove having a first width in said axis center direction of said syringe body and said projection having a second width broader than said first width in said axis center direction of said syringe body whereby said groove and said projection engage with a predetermined contact pressure to form said sealing structure when the main body is installed in said holding member installing hole;

said member main body having a holding member side engagement means capable of engaging with said piston.

2. The syringe assembly as set forth in claim 1, wherein a taper portion for connecting said liquid flow tube member is formed on a top end side of said member main body, projecting in said axis center direction of said member main body.

3. The syringe assembly as set forth in claim 2, wherein a liquid flow tube member engagement portion surrounding a periphery of said taper portion of said main member body is provided for connecting a liquid flow tube member.

4. The syringe assembly as set forth in claim 3, wherein said liquid flow tube member engagement portion comprises a tapped hole, open in said axis center direction of said member main body.

5. The syringe assembly as set forth in claim 3, wherein a stopper portion comprised of projecting bodies is formed at an inner peripheral portion of said holding member installing hole, and an abutting portion in a peripheral direction is provided at an outer peripheral portion of said member main body, projecting in a direction perpendicular to said axis center direction of said member main body such that when said member main body is installed in said holding member installing hole, an oscillation movement of said member main body in a peripheral direction with said axis center of said syringe body as its center can be prevented by the abutting in the peripheral direction between said abutting portion in the peripheral direction and said stopper portion.

6. The syringe assembly as set forth in claim 2, wherein a stopper portion comprised of projecting bodies is formed at an inner peripheral portion of said holding member installing hole, and an abutting portion in a peripheral direction is provided at an outer peripheral portion of said member main body, projecting in a direction perpendicular to said axis center direction of said member main body such that when said member main body is installed in said holding member installing hole, an oscillation movement of said member main body in a peripheral direction with said axis center of said syringe body as its center can be prevented by the abutting in the peripheral direction between said abutting portion in the peripheral direction and said stopper portion.

7. The syringe assembly as set forth in claim 1, wherein said piston comprises a piston body structured to be bent and broken between an operation portion and liquid medicine press portion of the piston.

8. The syringe assembly as set forth in claim 7, further comprising a piston stopper on said syringe body, located to prevent pulling of said liquid medicine press portion of said piston out of said syringe body upon retraction of the piston.

9. The syringe assembly as set forth in claim 8, wherein a notch for bending and breaking off an operation portion of said piston is located so as to be positioned at an open end portion of said syringe body when said piston abuts on said piston stopper.

10. The syringe assembly as set forth in claim 7, wherein a notch is formed in said piston body for bending and breaking at the notch.

11. The syringe assembly as set forth in claim 1, wherein said liquid flow tube holding member can be inserted into said holding member installing hole through said penetrating hole.

12. The syringe assembly as set forth in claim 11, wherein at least one slit is formed in the syringe body at a periphery of said penetrating hole and extending therein.

13. The syringe assembly as set forth in claim 12, wherein a taper portion for connecting said liquid flow tube member is formed on a top end side of said member main body, and projects in said axis center direction of said member main body.

14. The syringe assembly as set forth in claim 1, wherein a needle body is directly connected with said member main body.

15. The syringe assembly as set forth in claim 14, wherein said holding member side engagement means defines an opening communicating with an interior of said needle body.

16. The syringe assembly as set forth in claim 1, wherein the outside of a portion of the member main body adjacent to said one of said groove and said projection on said member main body is smaller than a corresponding portion of said holding member installing hole adjacent to the other of said groove and said projection.

17. The syringe assembly as set forth in claim 1, wherein said holding member side engagement means includes a groove penetrating said member main body in a direction perpendicular to said axis center direction of said member main body.

18. The syringe assembly as set forth in claim 1, wherein a deformation expediting groove is provided with said member main body adjacent to said holding member side engagement means at a direction perpendicular to said axis center direction of said member main body.

19. The syringe assembly as set forth in claim 1, wherein said piston comprises a piston side engagement means facing and capable of engaging with said holding member side engagement means of said liquid flow tube holding member.

* * * * *